US006583108B1

(12) United States Patent
Tamburini et al.

(10) Patent No.: US 6,583,108 B1
(45) Date of Patent: Jun. 24, 2003

(54) HUMAN BIKUNIN

(75) Inventors: Paul P. Tamburini, Kensington, CT (US); Gary Davis, Milford, CT (US); Katherine A. Delaria, West Haven, CT (US); Christopher W. Marlor, Bethany, CT (US); Daniel K. Muller, Orange, CT (US)

(73) Assignee: Bayer Corporation, West Haven, CT (US)

( * ) Notice: Subject to any disclaimer, the term of this patent is extended or adjusted under 35 U.S.C. 154(b) by 0 days.

(21) Appl. No.: 09/144,428

(22) Filed: Aug. 31, 1998

Related U.S. Application Data

(63) Continuation-in-part of application No. PCT/US97/03894, filed on Mar. 10, 1997, which is a continuation-in-part of application No. 08/725,251, filed on Oct. 4, 1996, now abandoned.
(60) Provisional application No. 60/019,793, filed on Jun. 14, 1996, and provisional application No. 60/013,106, filed on Mar. 11, 1996.

(51) Int. Cl.[7] .......................... A61K 38/57; C07K 14/81
(52) U.S. Cl. ................... 514/2; 514/12; 514/8; 530/350; 530/395; 530/324; 435/69.2; 536/23.5
(58) Field of Search ................... 530/350, 395, 530/324; 514/12, 8; 435/69.2; 536/23.5

(56) References Cited

U.S. PATENT DOCUMENTS

| | | | |
|---|---|---|---|
| 5,106,833 A | 4/1992 | Bronze, Jr. et al. | 514/12 |
| 5,223,482 A | 6/1993 | Schilling, Jr. et al. | 514/12 |
| 5,312,736 A | 5/1994 | Rasmussen et al. | 435/69.2 |
| 5,403,484 A | 4/1995 | Ladner et al. | 435/235.1 |
| 5,436,153 A | 7/1995 | Sprecher et al. | 435/252.33 |
| 5,441,931 A | 8/1995 | Sprecher et al. | 514/2 |
| 5,541,288 A | 7/1996 | Nakano et al. | 530/324 |
| 5,576,294 A | 11/1996 | Norris et al. | 514/12 |
| 5,663,143 A | 9/1997 | Ley et al. | 514/12 |
| 5,677,146 A | 10/1997 | Sprecher et al. | 435/69.1 |
| 5,728,674 A | 3/1998 | Sprecher et al. | 514/2 |
| 5,731,412 A | 3/1998 | Shimomura | 530/350 |
| 5,736,364 A | 4/1998 | Kelley et al. | 435/69.7 |
| 5,747,449 A | 5/1998 | Lasters et al. | 514/2 |
| 5,786,328 A | 7/1998 | Dennis et al. | 514/12 |
| 5,795,865 A | 8/1998 | Markland et al. | 514/12 |
| 5,834,244 A | 11/1998 | Dennis et al. | 435/69.2 |
| 5,854,396 A | 12/1998 | Shimomura et al. | 530/350 |

FOREIGN PATENT DOCUMENTS

| | | |
|---|---|---|
| EP | 0 563 389 A1 | 10/1993 |
| EP | 0 439 442 B1 | 3/1996 |
| WO | WO 92/15605 | 9/1992 |
| WO | WO 93/14120 | 7/1993 |
| WO | WO 95/18830 | 7/1995 |
| WO | WO 96/35788 | 11/1996 |
| WO | WO 96/03503 | 2/1997 |
| WO | WO 97/33996 | 9/1997 |
| WO | WO 98/33920 | 8/1998 |

OTHER PUBLICATIONS

Newton, B.B. ane Hall, R.L. Mucociliary clearance in the guinea–pig is increased by ouabain (i.v.) and by hypertonic saline (14.4%) aerosol. in *Cilia, Mucus and Mucociliary Interactions*. Ed. Baum, G.L., Priel, Z., Roth, Y., Liron, N., Ostfeld, E., Marcel Dekker. New York. 1998, pp. 285–294.

Wills, P.J., Garcia Suarez, M.J., Rutman, A., Wilson, R., and Cole, P.J. The ciliary transportability of sputum is slow on the mucus–depleted bovine trachea. *American Journal of Respiratory & Critical Care Medicine* 151(4):1255–1258, 1995.

Wills, P.J., Hall, R.L., Chan, W.M., and Cole, P.J. Sodium chloride increases the ciliary transportability of cystic fibrosis and bronchiectasis sputum on the mucus–depleted boving trachea. *Journal of Clinical Investigation* 97(11):9–13, 1997.

Mathews, L.W., Spector, S., Lemm, J., and Potter, J.L. Studies on Pulmonary secretions. I. The Overall Chemical Composition of Pulmonary Secretions from Patients with Cystic Fibrosis, Bronchiectasis, and Laryngectomy. *American Review of Respiratory Disease* 88:199–204, 1963.

Potter, J.L., Matthews, L.W., Spector, S., and Lemm, J. Studies on pulmonary secretions. II. Osmolality and the ionic environment of pulmonary secretions from patients with cystic fibrosis, bronchiectasis, and laryngectomy. *American Review of Respiratory Disease* 67(1):83–87, 1967.

Tomkiewicz, R.P., App, E.M., Zayas, J.G., Ramirez, O., Church, N., Boucher, R.C., Knowles, M.R., and King, M. Amiloride inhalation therapy in cystic fibrosis. Influence on ion content, hydration, and rheology of sputum. *American Review of Respiratory Disease* 148(4 Pt 1):1002–1007, 1993.

App, E.M., King, M., Helfesrieder, R., Kohler, D., and Matthys, H. (1990) Acute and long–term amiloride inhalation in cystic fibrosis lung disease. A rational approach to cystic fibrosis therapy. *American Review of Respiratory Disease* 141, 605–612.

Newton, B.B., Poll. C.T. and Hall, R.L. Inhalation of amiloride increases tracheal mucus velocity and decreases tracheal potential difference in the guinea–pig. *Pediatric Pulmonology* S17, Abs 364, 1998.

McAulay, A.E., Crossley, J., Place, G.A. and Poll, C.T. Effect of UTP on ion transport in tertiary cultures of human bronchial epithelial (HBE) cells. *Pediatric Pulmonology* S 17, Abs 141, 1998.

(List continued on next page.)

Primary Examiner—Christopher S. F. Low
Assistant Examiner—Gabriele E Bugaisky
(74) Attorney, Agent, or Firm—McDonnell Boehnen Hulbert & Berghoff

(57) ABSTRACT

The instant invention provides for proteins, polypeptides, nucleic acid sequences, constructs, expression vectors, host cells, pharmaceutical compositions of, and methods for using human placental bikunin, serine protease inhibitor domains, and fragments thereof.

9 Claims, 41 Drawing Sheets

OTHER PUBLICATIONS

Vallet, V., Chraibi, A., Gaeggeler, H.P., Horisberger, J.D., and Rossier, B.C. An epithelial serine protease activities the amiloride–sensitive sodium channel. *Nature* 389(6651):607–610, 1997.

Chraibi, A., Vallet, V., Firsov, D., Hess, S.K., and Horisberger, J.D. Protease modulation of the activity of the epithelial sodium channel expressed in xenopus oocytes. *Journal of General Physiology* 111(1):127–13 8, 1998.

Delaria, K.A., Muller, D.K., Marlor, C.W., Brown, J.E., Das, R.C., Roczniak, S.O. and Tamburini, P.P. Characterization of placental bikunin, a novel serine protease inhibitor. *Journal of Biological Chemistry* 272(18):12209–12214, 1997.

Marlor, C.W., Delaria, K.A., Davis, G., Muller, D.K., Greve, J.M., and Tamburini, P.P. Identification and cloning of human placental bikunin, a novel serine protease inhibitor containing two kunitz domains. *Journal of Biological Chemistry* 272(18):12202–12208, 1997.

O'Riordan, T.G., Otero, R., Mao, Y.M., Lauredo, I., and Abraham, W.M. Elastase contributes to antigen–induced mucociliary dysfunction in ovine airways. *American Journal of Respiratory & Critical Care Medicine* 97(5):1522–1528, 1997.

O'Riordan, T.G., Mao, Y.M., Otero, R., Lopez, J., Sabater, J.R., and Abraham, W.M. Budesonide affects allergic mucociliary dysfunction. *Journal of Applied Physiology* 85(3):1086–1091, 1998.

Lindberg, S., and Olsson, H., 1991 "Tissue Kallikrein Stimulates Mucociliary Activity in the Rabbit Maxillary Sinus," Acta Oto–Laryngologica, 111, (6) pp. 1126–1132.

Rasche, Von B., Marcic, I., and Ulmer, W. T., 1975 "Uber die Wirkung des Proteaseinhibitors Aprotinin auf die Lungenfunktion sowie die inhibitorische Aktivität des Sputums bei Patientin mit chronisch–obstruktiver Bronchitis" Arzneimittel–Forschung (Drug Res.) 25, Nr. (1) 110–116.

Schmidt, O.P., 1977, "Medikamentöse Therapie bronchosekretorischer Störungen" Medizinische Klinik. 72 (5), 145–160.

Robinson, et al., 1997. "Effect of increasing doses of hypertonic saline on mucociliary clearance in patients with cystic fibrosis," p. 900.

FIGURE 1

```
R35464  GGCCGGGTCG TTTCTCGCCT GGCTGGGATC GCTGCTCCTC TCTGGGGTCC   50
ORF          P  G  R  F  S  P  G  W  D  R  C  S  S  L  G  S   16

R35464  TGGCCGGCCG ACCGAGAACG CAGCATCCAC GACTTCTGCC TGGTGTCGAA  100
ORF       W  P  A  D  R  E  R  S  I  H  D  F  C  L  V  S  K   33

R35464  GGTGGTGGGC AGATTCCGGG CCTCCATGCC TAGGTGGTGG TACAATGTCA  150
ORF       V  V  G  R  E  R  A  S  M  P  R  W  W  Y  N  V  T   50

R35464  CTGACGGATC CTGCCAGCTG TTTGTGTATG GGGGCTGTGA CGGAAACAGC  200
ORF       D  G  S  C  Q  L  F  V  Y  G  G  C  D  G  N  S      66

R35464  AATAATTACC TGACCAAGGA GGAGTGCCTC AAGAAATGTG CCACTGTCAC  250
ORF       N  N  Y  L  T  K  E  E  C  L  K  K  C  A  T  V  T   83

R35464  AGAGAATGCC ACGGGTGACC TGGCCACCAG CAGGAATGCA GCGGATTCCT  300
ORF       E  N  A  T  G  D  L  A  T  S  R  N  A  A  D  S  S  100

R35464  CTGTCCCAAG TGCTCCCAGA AGGCAGGATT CTTGAAGACC ACTTCAGCGA  350
ORF       V  P  S  A  P  R  R  Q  D  S  *  R  P  L  Q  R     116

R35464  TATGTTTCAA NTATTGNAAG AATAATTGCA CCGNCAACGN ATT-------  393
ORF       Y  V  S  *  I  *  R  I  I  A  P  *  T  *           130

KEY
R35464 = Nucleic acid sequence of EST R35464 (SEQ ID NO: 12)
ORF   = EST R35464 Open Reading Frame Translation (SEQ ID NO: 13)
```

FIGURE 2

```
R74593  GCAATAATTA CCTGACCAAG GAGGAGTGCC TCAAGAAATG TGCCACTGTC   50
ORF        Q  *  L   P  D  Q  G   G  V  P    Q  E  M    C  H  C  H    17

R74593  ACAGAGAATG CCACGGGTGA CCTGGCCACC AGCAGGAATG CAGCGGATTC  100
ORF       R  E  C    H  G  *   P  G  H    Q  E  C    S  G  F      33

R74593  CTCTGTCCCA AGTCTCCCAG AAGGCAGGAT TCTGAAGACC ACTCCAGCGA  150
ORF       L  C  P    K  S  P    R  R  Q  D   S  E  D  H   S  S  D    50

R74593  TATGTTCAAC TATGAAGAAT ACTGCACCGC CAACGCAGTC ACTGGGCCTT  200
ORF       M  F  N    Y  E  E  Y    C  T  A    N  A  V    T  G  P  C   67

R74593  GCCGTGCATC CTTCCCACGC TGGTACTTTG ACGTGGAGAG GAACTCCTGC  250
ORF       R  A  S    F  P  R    W  Y  F  D    V  E  R    N  S  C     83

R74593  AATAACTTCA TCTATGGAGG CTGCCGGGGC AATAAGAACA GCTACCGCTC  300
ORF       N  N  F  I   Y  G  G    C  R  G    N  K  N    S  Y  R  S   100

R74593  TGAGGAGGCC TGCATGCTCC GCTGCTTCCG CCAGCAGGAG AATCCTCCCC  350
ORF       E  E  A    C  M  L    R  C  F  R    Q  Q  E    N  P  P  L  117

R74593  TGCCCCTTGG CTCAAAGGTG GTGGTTCTGG CCGGGGCTGT TTCGTGATGG  400
ORF       P  L  G    S  K  V    V  V  L    A  G  A  V    S  *  W    133

R74593  TGTTGATCCT TTTCCTGGGG AGCNTCCATG GTCTTACTGA TTCCGGGTGG  450
ORF       C  *  S  F   S  W  G    A  S  M    V  L  L  I    P  G  G   150

R74593  CAAGGAGGAA CCAGGAGCGT GCCCTGCGGA NCGTCTGGAG CTTCGGAGAT  500
ORF       K  E  E    P  G  A    C  P  A  X    R  L  E    L  R  R  *  167

R74593  GACAAGGGNT                                               510
ORF       Q  G                                                    169
```

KEY
R74593 = Nucleic acid sequence of EST R74593 (SEQ ID NO: 14)
ORF = EST R74593 Open Reading Frame Translation (SEQ ID NO: 15)

FIG. 3A-1

```
R35464        GGCCGGGTCGT TTCTCGCCTG GCTGGGA-TC GCTGCTCCTC TCTGGGGTCC  50
N39798                              TGGGANTC GCTGCTCCTC TCTGGGGTCC  28
H94519        GCNGCG-CGT TNNTCGCNT- GCTGGGA-TC GCTGCACCTC TCTGGGGTCG  47
R74593 corr.  ---------- ---------- ---------- ---------- ----------
Consensus     GGCCGGGTCGT TTCTCGCCTG GCTGGGA-TC GCTGCTCCTC TCTGGGGTCC  50
Translation    A  G  S   F  L  A  W   L  G   S   L  L  L    S  G  V   -3

R35464        TGGCCGGCCG ACCGAGAACG CAGCATCCAC GACTTCTGCC TGGTGTCGAA 100
N39798        TGG-CGGCCG ACCGAGAACG CAGCATCCAC GACTTCTGCC TGGTGTCGAA  77
H94519        NGG-CGGCCG ACCGAGAACG CAGCATCCAC GACTTCTGCC TGGTGTCGAA  96
R74593 corr.  ---------- ---------- ---------- ---------- ----------
Consensus     TGG-CGGCCG ACCGAGAAGG CAGCATCCAC GACTTCTGCC TGGTGTCGAA  99
Translation    L  A  A   R  E  R   S  I  H   D  E  C  L    V  S  K  15

R35464        GGTGGTGGGC AGATTCCGGG CCTCCATGCC TAGGTGGTGG TACAATGTCA 150
N39798        GGTGGTGGGC AGATGCCGGG CCTCCATGCC TAGGTGGTGG TACAATGTCA 127
H94519        GGTGGTGGGC AGATGCCGGG CCTCCATGCC TAGGTGGTGG TACAATGTCA 146
R74593 corr.  ---------- ---------- ---------- ---------- ----------
Consensus     GGTGGTGGGC AGATGCCGGG CCTCCATGCC TAGGTGGTGG TACAATGTCA 149
Translation    V  V  G   R  C  R   A  S  M  P    R  W  W    Y  N  V  T  32

R35464        CTGACGGATC CTGCCAGCTG TTTGTGTATG GGGGCTGTGA CGGAAACAGC 200
N39798        CTGACGGATC CTGCCAGCTG TTTGTGTATG GGGGCTGTGA CGGAAACAGC 177
H94519        CTGACGGATC CTGCCAGCTG TTTGTGTATG GGGGCTGTGA CGGAAACAGC 196
R74593 corr.  ---------- ---------- ---------- ---------- --------GC   2
Consensus     CTGACGGATC CTGCCAGCTG TTTGTGTATG GGGGCTGTGA CGGAAACAGC 199
Translation    D  G  S   C  Q  L   F  V  Y   G  C  D   G  N  S   48

R35464        AATAATTACC TGACCAAGGA GGAGTGCCTC AAGAAATGTG CCACTGTCAC 250
N39798        AATAATTACC TGACCAAGGA GGAGTGCCTC AAGAAATGTG CCACTGTCAC 227
H94519        AATAATTACC TGACCAAGGA GGAGTGCCTC AAGAAATGTG CCACTGTCAC 246
R74593 corr.  AATAATTACC TGACCAAGGA GGAGTGCCTC AAGAAATGTG CCACTGTCAC  52
Consensus     AATAATTACC TGACCAAGGA GGAGTGCCTC AAGAAATGTG CCACTGTCAC 249
Translation    N  N  Y   L  T  K   E  E  C   L  K  K   C  A  T  V   T  65

R35464        AGAGAATGCC ACGGGTGACC TGGCCACCAG CAGGAATGCA GCGGATTCCT 300
N39798        AGAGAATGCC ACGGGTGACC TGGCCACCAG CAGGAATGCA GCGGATTCCT 277
H94519        AGAGAATGCC ACGGGTGACC TGGCCACCAG CAGGAATGCA GCGGATTCCT 296
R74593 corr.  AGAGAATGCC ACGGGTGACC TGGCCACCAG CAGGAATGCA GCGGATTCCT 102
Consensus     AGAGAATGCC ACGGGTGACC TGGCCACCAG CAGGAATGCA GCGGATTCCT 299
Translation    E  N  A   T  G  D   L  A  T   S  R  N   A  D  S  S   82

R35464        CTGTCCCAAG TGCTCCAGA AGGCAGGATT CTTGAAGACC ACTTCAGCGA 350
N39798        CTGTCCCAAG TGCTCCCAGA AGGCAGGATT CT-GAAGACC ACTCCAGCGA 326
H94519        CTGTCCCAAG TGCTCCCAGA AGGCAGGATT CT-GAAGACC ACTCCAGCGA 345
R74593 corr.  CTGTCCCAAG TGCTCCCAGA AGGCAGGATT CT-GAAGACC ACTCCAGCGA 151
Consensus     CTGTCCCAAG TGCTCCCAGA AGGCAGGATT CT-GAAGACC ACTCCAGCGA 348
Translation    V  P  S    A  P  R    R  Q  D  S   E  D  H    S  S  D  98

R35464        TATGTTTCAA NTATTGNAAG AATAATTGCA CCGNCAACGN ATT------- 393
N39798        TATGTT-CAA CTA-TG-AAG AATACT-GCA CCGCCAACGC AGTCACTGGG 372
H94519        TATGTT-CAA CTA-TG-AAG AATACTGGCA CCGCCAACGC ATTCACTGGG 392
R74593 corr.  TATGTT-CAA CTA-TG-AAG AATACT-GCA CCGCCAACGC AGTCACTGGG 197
Consensus     TATGTT-CAA CTA-TG-AAG AATACT-GCA CCGCCAACGC AGTCACTGGG 394
Translation    M  F  N   Y  E  E   Y  C  T   A  N  A   V  T  G  113
```

FIG. 3A-2

```
R35464      ---------- ---------- ---------- ---------- ----------
N39798      CCTTGC-GTG GAATCCTTTC CCACGCTGGN AATTTNGACG TTGAGAAGGA 421
H94519      CCT-GC-GTG -CATCCTT-C CCACGCTGGT ACTTT-GNCG ----------  427
R74593 corr. CCTTGCCGTG -CATCCTT-C CCACGCTGGT ACTTT-GACG TGGAGA-GGA 243
Consensus   CCTTGCCGTG -CATCCTT-C CCACGCTGGT ACTTT-GACG TGGAGA-GGA 440
Translation   P  C  R  A    S  F    P  R  W  Y  F    D  V   E  R   N 129

R35464      ---------- ---------- ---------- ---------- ----------
N39798      AC-------- ---------- ---------- ---------- ----------  423
H94519      ---------- ---------- ---------- ---------- ----------
R74593 corr. ACTCCTGCAA TAACTTCATC TATGGAGGCT GCCGGGGCAA TAAGAACAGC 293
Consensus   ACTCCTGCAA TAACTTCATC TATGGAGGCT GCCGGGGCAA TAAGAACAGC 490
Translation    S  C  N   N  F  I   Y  G  G  C   R  G  N   K  N  S 145

R35464      ---------- ---------- ---------- ---------- ----------
N39798      ---------- ---------- ---------- ---------- ----------
H94519      ---------- ---------- ---------- ---------- ----------
R74593 corr. TACCGCTCTG AGGAGGCCTG CATGCTCCGC TGCTTCCGCC AGCAGGAGAA 343
Consensus   TACCGCTCTG AGGAGGCCTG CATGCTCCGC TGCTTCCGCC AGCAGGAGAA 540
Translation   Y  R  S  E    E  A  C   M  L  R   C  F  R   Q  Q  E  N 162

R35464      ---------- ---------- ---------- ---------- ----------
N39798      ---------- ---------- ---------- ---------- ----------
H94519      ---------- ---------- ---------- ---------- ----------
R74593 corr. TCCTCCCCTG CCCCTTGGCT CAAAGGTGGT GGTTCTGGCC GGGGCTGTTT 393
Consensus   TCCTCCCCTG CCCCTTGGCT CAAAGGTGGT GGTTCTGGCC GGGGCTGTTT 590
Translation    P  P  L   P  L  G  S   K  V  V   V  L  A   G  A  V  S 179

R35464      ---------- ---------- ---------- ---------- ----------
N39798      ---------- ---------- ---------- ---------- ----------
H94519      ---------- ---------- ---------- ---------- ----------
R74593 corr. CGTGATGGTG TTGATCCTTT TCCTGGGGAG CNTCCATGGT CTTACTGATT 443
Consensus   CGTGATGGTG TTGATCCTTT TCCTGGGGAG CNTCCATGGT CTTACTGATT 640
Translation    *  W  C   *  S  F   S  W  G  A   S  M  V   L  L  I  195

R35464      ---------- ---------- ---------- ---------- ----------
N39798      ---------- ---------- ---------- ---------- ----------
H94519      ---------- ---------- ---------- ---------- ----------
R74593 corr. CCGGGTGGCA AGGAGGAACC AGGAGCGTGC CCTGCGGANC GTCTGGAGCT 493
Consensus   CCGGGTGGCA AGGAGGAACC AGGAGCGTGC CCTGCGGANC GTCTGGAGCT 690
Translation   P  G  G  K    E  E  P   G  A  C   P  A  *   R  L  E  L 212

R35464      ---------- --------
N39798      ---------- --------
H94519      ---------- --------
R74593 corr. TCGGAGATGA CAAGGGNT                                          511
Consensus   TCGGAGATGA CAAGGGNT                                          708
Translation   R  R  *   Q  G                                               217
```

KEY
R35464 = Nucleic acid sequence of EST R35464 (SEQ ID NO.: 12)
N39798 = Nucleic acid sequence of EST N39798 (SEQ ID NO.: 17)
H94519 = Nucleic acid sequence of EST H94519 (SEQ ID NO.: 16)
R74593 corr. = Corrected version of (SEQ ID NO.: 14) G at b.p. 114
Consensus = Nucelic acid sequence for human bikunin (SEQ ID NO.: 9)
Translation = Amino acid Translation of Consensus (SEQ ID NO.: 10)

Schematic depicting the overlap of ESTs bearing homology to the cDNA sequence encoding placental bikunin

FIG. 4C-1

```
              1                                                      50
Bikunin   ......GCGA CCTCCGCGCG TTGGGAGGTG TAGCGCGGCT CTGAACGCGT
 N40851   ......GCGA CCTCCGCGCG TTGGGAGGTG TAGCGCGGCT CTGAACGCGT
 N39876   ......GCGA CCTCCGCGCG TTGGGAGGTG TAGCGCGGCT CTGAACGCGT
 R87894   .......... .......... .......... .......... ..........
 H16866   .....GGCGA CCTCCGCGCG TTGGGAGGTG TAGCGCG.CT CTGAACGGGN
 R34808   .......... .......... .......... .......... ..........
 T66058   .......... .......... .......... .......... ..........
 N57450   .......... .......... .........T TAGCGCGGCT CTGAACGCNA
 N57374   .......... .......... .......... .......... ..........
 R35464   .......... .......... .......... .......... ..........
 H94519   .......... .......... .......... .......... ..........
 N39798   .......... .......... .......... .......... ..........
 H87300   .......... .......... .......... .......... ..........
 R74593   .......... .......... .......... .......... ..........
 R31730   .......... .......... .......... .......... ..........
 R34701   .......... .......... .......... .......... ..........
 H02982   .......... .......... .......... .......... ..........
 R32676   .......... .......... .......... .......... ..........
 T47439   .......... .......... .......... .......... ..........
 R73968   .......... .......... .......... .......... ..........
 H39840   .......... .......... .......... .......... ..........
 H95233   .......... .......... .......... .......... ..........
 H39841   .......... .......... .......... .......... ..........
 N30199   .......... .......... .......... .......... ..........
 T52966   .......... .......... .......... .......... ..........
 N29508   .......... .......... .......... .......... ..........
 N26919   .......... .......... .......... .......... ..........
 N26910   .......... .......... .......... .......... ..........
 H16757   .......... .......... .......... .......... ..........
 N27732   .......... .......... .......... .......... ..........
```

FIG. 4C-2

```
            51                                                    100
Bikunin  GNA GGGCCG TTGAGTGTCG CAGGCGGCGA GGGCGCGAGT GAGGAGCAGA
N40851   NGAGNGGCCG TTGAGTGTCG CAGGCGGCGA GGGCGCGAGT GAGGAGCAGA
N39876   GCA.GGGCCG TTGAGTGTCG CAGGCGGCGA GGGCGCGAGT GAGGAGCAGA
R87894   .......... TTGAGTGTNG NAGGCGGCGA GGGCGCGAGT GAGGAGCAGA
H16866   ..ANGGGCCG TTGAGTGTCG CAGGCGGC.A GGGCN.GAGT GAGGAGCAGA
R34808   .......... .......... .......... ........G  GAGGAGCAGA
T66058   .......... .......... .......... .......... ..........
N57450   GAAGNGGCCG TTGAGTGTCG CAGGCGGCGA GGGCGCGAGT GAGGAGCAGA
N57374   .......... .......... .......... .......... .......AGA
R35464   .......... .......... .......... .......... ..........
H94519   .......... .......... .......... .......... ..........
N39798   .......... .......... .......... .......... ..........
H87300   .......... .......... .......... .......... ..........
R74593   .......... .......... .......... .......... ..........
R31730   .......... .......... .......... .......... ..........
R34701   .......... .......... .......... .......... ..........
H02982   .......... .......... .......... .......... ..........
R32676   .......... .......... .......... .......... ..........
T47439   .......... .......... .......... .......... ..........
R73968   .......... .......... .......... .......... ..........
H39840   .......... .......... .......... .......... ..........
H95233   .......... .......... .......... .......... ..........
H39841   .......... .......... .......... .......... ..........
N30199   .......... .......... .......... .......... ..........
T52966   .......... .......... .......... .......... ..........
N29508   .......... .......... .......... .......... ..........
N26919   .......... .......... .......... .......... ..........
N26910   .......... .......... .......... .......... ..........
H16757   .......... .......... .......... .......... ..........
N27732   .......... .......... .......... .......... ..........
```

FIG. 4C-3

```
              101                                                    150
Bikunin   CCCAGGCATC GCGCGCCGAG AAGNC GGGC GTCCCCACAC TGAAGGTCCG
  N40851  CCCAGGCATC GCGCGCCGAG AAGNC.GGGC GTCCCCACAC TGAAGGTCCG
  N39876  CCCAGGCATC GCGCGCCGAG AAGNC.GGGC NTCCCCACAC TGAAGGTCCG
  R87894  CCCAGGCATC GCGCGCCGAG AAGGCCGGGC GTCCCCACAC TGAAGGTCCG
  H16866  CCCAGGCATC GCGCGCCGAG AAGNC.GGGC GTCCCCACAC TGAAGGTCCG
  R34808  CCCAGGCATC GCGCGCCGAG AAGNC.GGGC GTCCCCACAC TGAAGGTCCG
  T66058  .......... .......... .......... .......... ..........
  N57450  CCCAGGCATC GCGCGCCGAG AAGNC.GGGC GTCCCCACAC TGAAGGTCCG
  N57374  CCCAGGCATC GCGCGCCGAG AAGNC.GGGC GTCCCCACAC TGAAGGTCCG
  R35464  .......... .......... .......... .......... ..........
  H94519  .......... .......... .......... .......... ..........
  N39798  .......... .......... .......... .......... ..........
  H87300  .......... .......... .......... .......... ..........
  R74593  .......... .......... .......... .......... ..........
  R31730  .......... .......... .......... .......... ..........
  R34701  .......... .......... .......... .......... ..........
  H02982  .......... .......... .......... .......... ..........
  R32676  .......... .......... .......... .......... ..........
  T47439  .......... .......... .......... .......... ..........
  R73968  .......... .......... .......... .......... ..........
  H39840  .......... .......... .......... .......... ..........
  H95233  .......... .......... .......... .......... ..........
  H39841  .......... .......... .......... .......... ..........
  N30199  .......... .......... .......... .......... ..........
  T52966  .......... .......... .......... .......... ..........
  N29508  .......... .......... .......... .......... ..........
  N26919  .......... .......... .......... .......... ..........
  N26910  .......... .......... .......... .......... ..........
  H16757  .......... .......... .......... .......... ..........
  N27732  .......... .......... .......... .......... ..........
```

FIG. 4C-4

```
            151                                                      200
Bikunin  GAAAGGCGAC TTCCGGGGGC TTTGGCACCT GGCGGACCCT CCCGGAGCGT
 N40851  GAAAGGCGAC TTCCGGGGGC TTTGGCACCT GGCGGACCCT CCCGGAGCGT
 N39876  GAAAGGCGAC TTCCGGGGGC TTTGGCACCT GGCGGACCCT CCCGGAGCGT
 R87894  GAAAGGCGAC TTCCGGGGGC TTTGGCACCT GGCGGACCCT CCCGGAGCGT
 H16866  GAAAGGCGAC TTCCGGGGGC TTTGGCACCT GGCGGACG.T CCCGGAGCN.
 R34808  GAAAGGCGAC TTCCGGGGGC TTTGGCACCT GGCGGACCCT CCCGGAGCGT
 T66058  .......... .......... .......... ...GGACCCT CCCGGAGCGT
 N57450  GAAAGGCGAC TTCCGGGGGC TTTGGCACCT GGCGGACCCT CCCGGAGCGT
 N57374  GAAAGGCGAC TTCCGGGGGC TTTGGCACCT GGCGGACCCT CCCGGAGCGT
 R35464  .......... .......... .......... .......... ..........
 H94519  .......... .......... .......... .......... ..........
 N39798  .......... .......... .......... .......... ..........
 H87300  .......... .......... .......... .......... ..........
 R74593  .......... .......... .......... .......... ..........
 R31730  .......... .......... .......... .......... ..........
 R34701  .......... .......... .......... .......... ..........
 H02982  .......... .......... .......... .......... ..........
 R32676  .......... .......... .......... .......... ..........
 T47439  .......... .......... .......... .......... ..........
 R73968  .......... .......... .......... .......... ..........
 H39840  .......... .......... .......... .......... ..........
 H95233  .......... .......... .......... .......... ..........
 H39841  .......... .......... .......... .......... ..........
 N30199  .......... .......... .......... .......... ..........
 T52966  .......... .......... .......... .......... ..........
 N29508  .......... .......... .......... .......... ..........
 N26919  .......... .......... .......... .......... ..........
 N26910  .......... .......... .......... .......... ..........
 H16757  .......... .......... .......... .......... ..........
 N27732  .......... .......... .......... .......... ..........
```

FIG. 4C-5

```
              201                                                    250
Bikunin   CGGCACCTGA ACGCGAGGCG CTCCATTGCG CGTGCGTTTG .AGGGGCTTC
  N40851  CGGCACCTGA ACGCGAGGCG CTCCATTGCG CGTGCGTNTG .AGGGGCTTC
  N39876  CGGCACCTGA ACGCGAGGCG CTCCATTGCG CGTGCGTTTG .AGGGGCTTC
  R87894  CGGCACCTGA ACGCGAGGCG CTCCATTGCG CGTGCGTTTG .AGGGGCTTC
  H16866  .GGCACCTGA ACGCGAGGCG CTCCATTGCG CGTGCGTTTG .AGGGGCTTC
  R34808  CGGCACCTGA ACGCGAGGCG CTCCATTGCG CGTGCGTNTG GAGGGGCTTC
  T66058  CGGCACCTGA ACGCGAGGC. CTCCATTGCG .GTGCGTGTG NAGGGGCTTC
  N57450  CGGCACCTGA ACGCGAGGCG CTCCATTGCG CGTGCGTTTG .AGGGGCTTC
  N57374  CGGCACCTGA ACGCGAGGC. CTCCATTGC. CGTGCGTTNG .AGGGGCTTC
  R35464  .......... .......... .......... .......... ..........
  H94519  .......... .......... .......... .......... ..........
  N39798  .......... .......... .......... .......... ..........
  H87300  .......... .......... .......... .......... ..........
  R74593  .......... .......... .......... .......... ..........
  R31730  .......... .......... .......... .......... ..........
  R34701  .......... .......... .......... .......... ..........
  H02982  .......... .......... .......... .......... ..........
  R32676  .......... .......... .......... .......... ..........
  T47439  .......... .......... .......... .......... ..........
  R73968  .......... .......... .......... .......... ..........
  H39840  .......... .......... .......... .......... ..........
  H95233  .......... .......... .......... .......... ..........
  H39841  .......... .......... .......... .......... ..........
  N30199  .......... .......... .......... .......... ..........
  T52966  .......... .......... .......... .......... ..........
  N29508  .......... .......... .......... .......... ..........
  N26919  .......... .......... .......... .......... ..........
  N26910  .......... .......... .......... .......... ..........
  H16757  .......... .......... .......... .......... ..........
  N27732  .......... .......... .......... .......... ..........
```

FIG. 4C-6

```
              251                                                      300
Bikunin   CCGCACCT G ATCGCGAGAC CCCAACGGCT GGTGG CGTC GC TG CGCG
 N40851   CCGCACCT.G ATCGCGAGAC CCCAACGGCT GGTGG.CGTC GCCTG.CGCG
 N39876   CCGCACCT.G ATCGCGAGAC CCCAACGGCT GGTGG.CGTC GCCTG.CGCG
 R87894   CCGCACCT.G ATCGCGAGAC CCCAACGGCT GGTNG.CGTC GC.TN.CGCG
 H16866   CCGCACCT.G ATCGCGAGAC CCCAACGGCT GGTNG.CGTC GC.TGGCGCG
 R34808   CCGCACCT.G ATCGCGAGAC CCCAACGGCT GGTGGGCGTC GC.TG.CGCG
 T66058   CCGCACCT.G ATCGCGAGAC CCCAACGGCT GGTGG.CGTC GC.TG.CGCG
 N57450   CCGCACCT.G ATCGCGAGAC CCCAACGGCT GGTGG.CGTC GCCTG.CGCG
 N57374   CCGGAACTTG ATCGCGAGAC CCCAACGGCT GGTGG.CGTC GC.TG.CGCG
 R35464   ..........  ..........  ..........  ..........  ..........
 H94519   ..........  ..........  ..........  ..........  ..........
 N39798   ..........  ..........  ..........  ..........  ..........
 H87300   ..........  ..........  ..........  ..........  ..........
 R74593   ..........  ..........  ..........  ..........  ..........
 R31730   ..........  ..........  ..........  ..........  ..........
 R34701   ..........  ..........  ..........  ..........  ..........
 H02982   ..........  ..........  ..........  ..........  ..........
 R32676   ..........  ..........  ..........  ..........  ..........
 T47439   ..........  ..........  ..........  ..........  ..........
 R73968   ..........  ..........  ..........  ..........  ..........
 H39840   ..........  ..........  ..........  ..........  ..........
 H95233   ..........  ..........  ..........  ..........  ..........
 H39841   ..........  ..........  ..........  ..........  ..........
 N30199   ..........  ..........  ..........  ..........  ..........
 T52966   ..........  ..........  ..........  ..........  ..........
 N29508   ..........  ..........  ..........  ..........  ..........
 N26919   ..........  ..........  ..........  ..........  ..........
 N26910   ..........  ..........  ..........  ..........  ..........
 H16757   ..........  ..........  ..........  ..........  ..........
 N27732   ..........  ..........  ..........  ..........  ..........
```

FIG. 4C-7

```
              301                                                          350
Bikunin   TC TCGGCTG AGCT GGCCA TGGCGCANT GTTGC GGGC T GAGGC GG
N40851    TC.TCGGCTG AGCT.GGNCA TGTCG
N39876    TC.TCGGCTG AGCT.GGCCA TGGCGCACT. G.TGCGGNGC T.GAGGC.G
R87894    TC.TCGGCTG AGCTTGGCCA TGGCGCANT. GTTNC.GGGC T.NAGGC.GG
H16866    TTCTCGGCTG AGCT.GGCCA TGGCGCANT. GTTGC.GNGC T.GAGGC.GG
R34808    TCTTCGGCTG AGCTGGGCCA TGGCGCANTT GTTGC.GGGC T.GAGGC.GG
T66058    TC.TCGGCTG AGCT.GGCCA TGGCGCANT. GTTGC.GNGC T.GAGGC.GG
N57450    TC.TCGGCTG AGCT.GGCCA TGGCGCANT. GGTGC.GGGC TTGAGGC.GG
N57374    TCCTCGGCTG AGCT.GGCCA TGGCGCANT. GGTGCCGNGC T.GAGGCCGG
R35464    .........  .........  .........  ........  ....GGCCGG
H94519    .........  .........  .........  ........  ..........
N39798    .........  .........  .........  ........  ..........
H87300    .........  .........  .........  ........  ..........
R74593    .........  .........  .........  ........  ..........
R31730    .........  .........  .........  ........  ..........
R34701    .........  .........  .........  ........  ..........
H02982    .........  .........  .........  ........  ..........
R32676    .........  .........  .........  ........  ..........
T47439    .........  .........  .........  ........  ..........
R73968    .........  .........  .........  ........  ..........
H39840    .........  .........  .........  ........  ..........
H95233    .........  .........  .........  ........  ..........
H39841    .........  .........  .........  ........  ..........
N30199    .........  .........  .........  ........  ..........
T52966    .........  .........  .........  ........  ..........
N29508    .........  .........  .........  ........  ..........
N26919    .........  .........  .........  ........  ..........
N26910    .........  .........  .........  ........  ..........
H16757    .........  .........  .........  ........  ..........
N27732    .........  .........  .........  ........  ..........
```

FIG. 4C-8

```
          351                                                    400
Bikunin  AC  GG CG     TTTCTCG  CC TGCTGGG A TCGCT GC T CCTCTCT
R87894   ACG.
H16866   AC..CGNCGT TTTTCTTCG. CCTTGCTGGG ATTCGCTTGC TTCCTNTCTG
R34808   ACGCGGNCG. .TTTTTTCGN CCTTGCTGGG ATTCG.TTG. TTNCTCTCTN
T66058   ...CGGNCG. .TTTTCTCG. CC.TGCTGGG A.TCGCT.GC T.CCTCTCT.
N57450   ANN.NGCCG. ..TTTCTCG. CC.TGCTGGG A.TCGCT.GC T.CCTCTCT.
N57374   AG..GGCCGG ..TTTCTCG. CCTTGCTGGG A.TCGCT.GC T.CCTCTCTG
R35464   .....GTCG. ...TTTCTCG. CCTGGCTGGG A.TCGCT.GC T.CCTCTCT.
H94519   .GCNGCGCG. ...TTNNTCG. CN.TGCTGGG A.TCGCT.GC A.CCTCTCT.
N39798   .......... .......... .....CTGGG ANTCGCT.GC T.CCTCTCT.
H87300   .......... .......... .......... .......... ..........
R74593   .......... .......... .......... .......... ..........
R31730   .......... .......... .......... .......... ..........
R34701   .......... .......... .......... .......... ..........
H02982   .......... .......... .......... .......... ..........
R32676   .......... .......... .......... .......... ..........
T47439   .......... .......... .......... .......... ..........
R73968   .......... .......... .......... .......... ..........
H39840   .......... .......... .......... .......... ..........
H95233   .......... .......... .......... .......... ..........
H39841   .......... .......... .......... .......... ..........
N30199   .......... .......... .......... .......... ..........
T52966   .......... .......... .......... .......... ..........
N29508   .......... .......... .......... .......... ..........
N26919   .......... .......... .......... .......... ..........
N26910   .......... .......... .......... .......... ..........
H16757   .......... .......... .......... .......... ..........
N27732   .......... .......... .......... .......... ..........
```

FIG. 4C-9

```
          401                                                    450
Bikunin  GGGG TCCTG G   CGGCCGA CCGA GAACG CA GCA TCC ACGACTT CT
H16866   GGGGTTCCTG GG.CGGCCGA CCGA.GAACG CA.GCA.TCC AAGAATTTTT
R34808   GGGGTTC.TG GGGNGGCCGA NCGA.GAACG CAAGCA.TTC ACGA.TTT
T66058   GGGG.TCCTG G..CGGCCGA CCGA.GAACG CA.GCA.TCC ACGANTT.CT
N57450   GGGG.TCCTG G..CGGCCGA CCGA.GAACG CA.GCA.TCC ACGACTT.CT
N57374   GGGG.TCCTG G..CGGCCGA NCGAAGAANG CA.GCAATCC ANGAATTNCT
R35464   GGGG.TCCTG G.CCGGCCGA CCGA.GAACG CA.GCA.TCC ACGACTT.CT
H94519   GGGG.TCGNG G..CGGCCGA CCGA.GAACG CA.GCA.TCC ACGACTT.CT
N39798   GGGG.TCCTG G..CGGCCGA CCGA.GAACG CA.GCA.TCC ACGACTT.CT
H87300   .......... .......... .......... .......... ..........
R74593   .......... .......... .......... .......... ..........
R31730   .......... .......... .......... .......... ..........
R34701   .......... .......... .......... .......... ..........
H02982   .......... .......... .......... .......... ..........
R32676   .......... .......... .......... .......... ..........
T47439   .......... .......... .......... .......... ..........
R73968   .......... .......... .......... .......... ..........
H39840   .......... .......... .......... .......... ..........
H95233   .......... .......... .......... .......... ..........
H39841   .......... .......... .......... .......... ..........
N30199   .......... .......... .......... .......... ..........
T52966   .......... .......... .......... .......... ..........
N29508   .......... .......... .......... .......... ..........
N26919   .......... .......... .......... .......... ..........
N26910   .......... .......... .......... .......... ..........
H16757   .......... .......... .......... .......... ..........
N27732   .......... .......... .......... .......... ..........
```

FIG. 4C-10

```
             451                                                              500
Bikunin   GCCTGGTGT   CGAAGGT GG   TGGGCAGATG   CCGGG CCTC   CATGCCTA G
H16866    GCC
T66058    TCCTGGTGTT  CGAAGG
N57450    GCCTGGTGT.  CGAAGGT.GG  TGGGCAG
N57374    GCCTGGTGTT  CGAAAGTTGG  TGGGCANATT  CCGGGGCCTT  CATGNCTAAG
R35464    GCCTGGTGT.  CGAAGGT.GG  TGGGCAGATT  CCGGG.CCTC  CATGCCTA.G
H94519    GCCTGGTGT.  CGAAGGT.GG  TGGGCAGATG  CCGGG.CCTC  CATGCCTA.G
N39798    GCCTGGTGT.  CGAAGGT.GG  TGGGCAGATG  CCGGG.CCTC  CATGCCTA.G
H87300    ..........  ..........  ..........  ..........  ..........
R74593    ..........  ..........  ..........  ..........  ..........
R31730    ..........  ..........  ..........  ..........  ..........
R34701    ..........  ..........  ..........  ..........  ..........
H02982    ..........  ..........  ..........  ..........  ..........
R32676    ..........  ..........  ..........  ..........  ..........
T47439    ..........  ..........  ..........  ..........  ..........
R73968    ..........  ..........  ..........  ..........  ..........
H39840    ..........  ..........  ..........  ..........  ..........
H95233    ..........  ..........  ..........  ..........  ..........
H39841    ..........  ..........  ..........  ..........  ..........
N30199    ..........  ..........  ..........  ..........  ..........
T52966    ..........  ..........  ..........  ..........  ..........
N29508    ..........  ..........  ..........  ..........  ..........
N26919    ..........  ..........  ..........  ..........  ..........
N26910    ..........  ..........  ..........  ..........  ..........
H16757    ..........  ..........  ..........  ..........  ..........
N27732    ..........  ..........  ..........  ..........  ..........
```

FIG. 4C-11

```
              501                                                          550
Bikunin     G TGGT GGT  ACAATGTCAC  TGACGGATCC  TGCCAGCTGT  TTGTGT ATG
N57374      GTTGGTTGGT  ANAATGTNAA  TTAANGATTC  TTGCAACTGT  TTGTGTNATT
R35464      G.TGGT.GGT  ACAATGTCAC  TGACGGATCC  TGCCAGCTGT  TTGTGT.ATG
H94519      G.TGGT.GGT  ACAATGTCAC  TGACGGATCC  TGCCAGCTGT  TTGTGT.ATG
N39798      G.TGGT.GGT  ACAATGTCAC  TGACGGATCC  TGCCAGCTGT  TTGTGT.ATG
H87300      ..........  ..........  ..........  ..........  ..........
R74593      ..........  ..........  ..........  ..........  ..........
R31730      ..........  ..........  ..........  ..........  ..........
R34701      ..........  ..........  ..........  ..........  ..........
H02982      ..........  ..........  ..........  ..........  ..........
R32676      ..........  ..........  ..........  ..........  ..........
T47439      ..........  ..........  ..........  ..........  ..........
R73968      ..........  ..........  ..........  ..........  ..........
H39840      ..........  ..........  ..........  ..........  ..........
H95233      ..........  ..........  ..........  ..........  ..........
H39841      ..........  ..........  ..........  ..........  ..........
N30199      ..........  ..........  ..........  ..........  ..........
T52966      ..........  ..........  ..........  ..........  ..........
N29508      ..........  ..........  ..........  ..........  ..........
N26919      ..........  ..........  ..........  ..........  ..........
N26910      ..........  ..........  ..........  ..........  ..........
H16757      ..........  ..........  ..........  ..........  ..........
N27732      ..........  ..........  ..........  ..........  ..........

551                                                          600
Bikunin     GGGGCTGTGA  CGGAAACA  GCAATAATTA  CCTGACCAAG  GA GGAGTGC
N57374      GGGGCTNTTA  AACGGAAANA  .CAATAATNA  CCTGACCAAA  GAAGNAAT..
R35464      GGGGCTGTGA  ..CGGAAACA  GCAATAATTA  CCTGACCAAG  GA.GGAGTGC
H94519      GGGGCTGTGA  ..CGGAAACA  GCAATAATTA  CCTGACCAAG  GA.GGAGTGC
N39798      GGGGCTGTGA  ..CGGAAACA  GCAATAATTA  CCTGACCAAG  GA.GGAGTGC
H87300      GATTCGGCAC  AGGGGAAACA  GCAATAATTA  CCTGACCAAG  GA.GGAGTNC
R74593      ..........  ..........  GCAATAATTA  CCTGACCAAG  GA.GGAGTGC
R31730      ..........  ..........  ..........  ..........  ..........
R34701      ..........  ..........  ..........  ..........  ..........
H02982      ..........  ..........  ..........  ..........  ..........
R32676      ..........  ..........  ..........  ..........  ..........
T47439      ..........  ..........  ..........  ..........  ..........
R73968      ..........  ..........  ..........  ..........  ..........
H39840      ..........  ..........  ..........  ..........  ..........
H95233      ..........  ..........  ..........  ..........  ..........
H39841      ..........  ..........  ..........  ..........  ..........
N30199      ..........  ..........  ..........  ..........  ..........
T52966      ..........  ..........  ..........  ..........  ..........
N29508      ..........  ..........  ..........  ..........  ..........
N26919      ..........  ..........  ..........  ..........  ..........
N26910      ..........  ..........  ..........  ..........  ..........
H16757      ..........  ..........  ..........  ..........  ..........
N27732      ..........  ..........  ..........  ..........  ..........
```

FIG. 4C-12

```
              601                                                          650
Bikunin   CTCAAGAAAT GTGCCACTGT CACAGAGAAT GCCACGGGTG ACCTGGCCAC
  R35464  CTCAAGAAAT GTGCCACTGT CACAGAGAAT GCCACGGGTG ACCTGGCCAC
  H94519  CTCAAGAAAT GTGCCACTGT CACAGAGAAT GCCACGGGTG ACCTGGCCAC
  N39798  CTCAAGAAAT GTGCCACTGT CACAGAGAAT GCCACGGGTG ACCTGGCCAC
  H87300  CTCAAGAAAT GTNCCACTGT CACAGAGAAT GCCACGGGTG ACCTGGCCAC
  R74593  CTCAAGAAAT GTGCCACTGT CACAGAGAAT GCCACGGGTG ACCTGGCCAC
  R31730  .......... .......... .......... .......... ..........
  R34701  .......... .......... .......... .......... ..........
  H02982  .......... .......... .......... .......... ..........
  R32676  .......... .......... .......... .......... ..........
  T47439  .......... .......... .......... .......... ..........
  R73968  .......... .......... .......... .......... ..........
  H39840  .......... .......... .......... .......... ..........
  H95233  .......... .......... .......... .......... ..........
  H39841  .......... .......... .......... .......... ..........
  N30199  .......... .......... .......... .......... ..........
  T52966  .......... .......... .......... .......... ..........
  N29508  .......... .......... .......... .......... ..........
  N26919  .......... .......... .......... .......... ..........
  N26910  .......... .......... .......... .......... ..........
  H16757  .......... .......... .......... .......... ..........
  N27732  .......... .......... .......... .......... ..........

651                                                          700
Bikunin   CAGCAGGAAT GCAGCGGATT CCTCTGTCCC AAGTGCTCCC AGAAGGCAGG
  R35464  CAGCAGGAAT GCAGCGGATT CCTCTGTCCC AAGTGCTCCC AGAAGGCAGG
  H94519  CAGCAGGAAT GCAGCGGATT CCTCTGTCCC AAGTGCTCCC AGAAGGCAGG
  N39798  CAGCAGGAAT GCAGCGGATT CCTCTGTCCC AAGTGCTCCC AGAAGGCAGG
  H87300  CAGCAGGAAT GCAGCGGATT CCTCTGTCCC AAGTGCTCCC AGAAGGCAGG
  R74593  CAGCAGGAAT GCAGCGGATT CCTCTGTCCC AAGT.CTCCC AGAAGGCAGG
  R31730  .......... .......... .......... .......... ..........
  R34701  .......... .......... .......... .......... ..........
  H02982  .......... .......... .......... .......... ..........
  R32676  .......... .......... .......... .......... ..........
  T47439  .......... .......... .......... .......... ..........
  R73968  .......... .......... .......... .......... ..........
  H39840  .......... .......... .......... .......... ..........
  H95233  .......... .......... .......... .......... ..........
  H39841  .......... .......... .......... .......... ..........
  N30199  .......... .......... .......... .......... ..........
  T52966  .......... .......... .......... .......... ..........
  N29508  .......... .......... .......... .......... ..........
  N26919  .......... .......... .......... .......... ..........
  N26910  .......... .......... .......... .......... ..........
  H16757  .......... .......... .......... .......... ..........
  N27732  .......... .......... .......... .......... ..........
```

FIG. 4C-13

```
           701                                                    750
Bikunin    ATTCT GAAG  ACCACTCCAG  CGATATGTT  CAACTAT   G  AAGAATACTG
R35464     ATTCTTGAAG  ACCACTTCAG  CGATATGTTT CAANTATTGN    AAGAATAATT
H94519     ATTCT.GAAG  ACCACTCCAG  CGATATGTT. CAACTAT..G    AAGAATACTG
N39798     ATTCT.GAAG  ACCACTCCAG  CGATATGTT. CAACTAT..G    AAGAATACTG
H87300     ATTCT.GAAG  ACCACTCCAG  CGATATGTT. CAACTAT..G    AAGAATACTG
R74593     ATTCT.GAAG  ACCACTCCAG  CGATATGTT. CAACTAT..G    AAGAATACTG
R31730     ..........  ..........  .........  ..........    ..........
R34701     ..........  ..........  .........  ..........    ..........
H02982     ..........  ..........  .........  ..........    ..........
R32676     ..........  ..........  .........  ..........    ..........
T47439     ..........  ..........  .........  ..........    ..........
R73968     ..........  ..........  .........  ..........    ..........
H39840     ..........  ..........  .........  ..........    ..........
H95233     ..........  ..........  .........  ..........    ..........
H39841     ..........  ..........  .........  ..........    ..........
N30199     ..........  ..........  .........  ..........    ..........
T52966     ..........  ..........  .........  ..........    ..........
N29508     ..........  ..........  .........  ..........    ..........
N26919     ..........  ..........  .........  ..........    ..........
N26910     ..........  ..........  .........  ..........    ..........
H16757     ..........  ..........  .........  ..........    ..........
N27732     ..........  ..........  .........  ..........    ..........

751                                                    800
Bikunin    CACCGCCAA  CGCAGT  CAC  TGGGCC  TTG  CCGTG  CAT  CCTT  CCCAC
R35464     GCACCGNCAA CGNATT
H94519     GCACCGCCAA CGCATT.CAC  TGGGCC..TG  C.GTG.CAT. CCTT.CCCAC
N39798     .CACCGCCAA CGCAGT.CAC  TGGGGCCTTG  C.GTGGAAT. CCTTTCCCAC
H87300     .CACCGCCAA CGCAGTNCAC  TGGGCC.TTG  C.GTGGCATN CCTT.CCCAC
R74593     .CACCGCCAA CGCAGT.CAC  TGGGCC.TTG  CCGTG.CAT. CCTT.CCCAC
R31730     ..........  ..........  ..........  ..........  ..........
R34701     ..........  ..........  ..........  ..........  ..........
H02982     ..........  ..........  ..........  ..........  ..........
R32676     ..........  ..........  ..........  ..........  ..........
T47439     ..........  ..........  ..........  ..........  ..........
R73968     ..........  ..........  ..........  ..........  ..........
H39840     ..........  ..........  ..........  ..........  ..........
H95233     ..........  ..........  ..........  ..........  ..........
H39841     ..........  ..........  ..........  ..........  ..........
N30199     ..........  ..........  ..........  ..........  ..........
T52966     ..........  ..........  ..........  ..........  ..........
N29508     ..........  ..........  ..........  ..........  ..........
N26919     ..........  ..........  ..........  ..........  ..........
N26910     ..........  ..........  ..........  ..........  ..........
H16757     ..........  ..........  ..........  ..........  ..........
N27732     ..........  ..........  ..........  ..........  ..........
```

FIG. 4C-14

```
            801                                                    850
Bikunin  GCTGGTACTT T GACGTGGA GA GGAACTC CTG CAATAA CTTCATCTAT
H94519   GCTGGTACTT T.GNCGT
N39798   GCTGGNAATT TNGACGTTGA GAAGGAAC
H87300   GCTNGTACTT T.GACGTGGA GA.GGAACTC CTGGCAATAA CTTCATCTAT
R74593   GCTGGTACTT T.GACGTGGA GA.GGAACTC CTG.CAATAA CTTCATCTAT
R31730   .......... .......... .......... .......... ..........
R34701   .......... .......... .......... .......... ..........
H02982   .......... ........GA GA.GGAACTC CTG.CAATAA CTTCATCTAT
R32676   .......... .......... .......... .........G ATTC..GGAA
T47439   .......... .......... .......... .......... ..........
R73968   .......... .......... .......... .......... ..........
H39840   .......... .......... .......... .......... ..........
H95233   .......... .......... .......... .......... ..........
H39841   .......... .......... .......... .......... ..........
N30199   .......... .......... .......... .......... ..........
T52966   .......... .......... .......... .......... ..........
N29508   .......... .......... .......... .......... ..........
N26919   .......... .......... .......... .......... ..........
N26910   .......... .......... .......... .......... ..........
H16757   .......... .......... .......... .......... ..........
N27732   .......... .......... .......... .......... ..........

851                                                    900
Bikunin  GGAGGCT GC CGGGGCAAT  AAGAACAG C TACCGCTC T GAGGAGGCCT
H87300   GGAGGCTTGC CGGGGCAATN AAGAACAGNT TACCGCTCTT TAGGAGGCCT
R74593   GGAGGCT.GC CGGGGCAAT. AAGAACAG.C TACCGCTC.T GAGGAGGCCT
R31730   .......... .......... .......G.C TACCGCTC.T GAGGAGGCCT
R34701   .......... .......... .......... .......... ..........
H02982   GGNGGCT.GC CGGGG.AAT. AAGAACA.NC TACCGCTC.T GAGGAGGCCT
R32676   CGAGGA..GC CGGGGCAAT. AAGAACAG.C TACCGCTC.T GAGGAGGCCT
T47439   .......... .......... .......... .......... ....NGGCCT
R73968   .......... .......... .......... .......... ..........
H39840   .......... .......... .......... .......... ..........
H95233   .......... .......... .......... .......... ..........
H39841   .......... .......... .......... .......... ..........
N30199   .......... .......... .......... .......... ..........
T52966   .......... .......... .......... .......... ..........
N29508   .......... .......... .......... .......... ..........
N26919   .......... .......... .......... .......... ..........
N26910   .......... .......... .......... .......... ..........
H16757   .......... .......... .......... .......... ..........
N27732   .......... .......... .......... .......... ..........
```

FIG. 4C-15

```
            901                                                       950
Bikunin   GCA TGCTC CGCTGCTTCC GC                         CA GCAGGA
H87300    .GCA.T.... .
R74593    .GCA.TGCTC CGCTGCTTCC GC........ .......... .CA.GCAGGA
R31730    .GCA.TGCTC CGCTGCTTCC GC........ .......... .CA.GCAGGA
R34701    .......... ......TTCC GC........ .......... .CAAGCAGGA
H02982    .GCG.TGCTC CGCTGCTTCC GCTGTGTGTT CTCTTCCAGG CCA.GCAGGA
R32676    .GCA.TGCTC CGCTGCTTCC GC........ .......... .CA.GCAGGA
T47439    TGCAGTGCTC CGCTGCTTCC GC........ .......... .CA.GCAGGA
R73968    .......... .......... .......... .......... ..........
H39840    .......... .......... .......... .......... ..........
H95233    .......... .......... .......... .......... ..........
H39841    .......... .......... .......... .......... ..........
N30199    .......... .......... .......... .......... ..........
T52966    .......... .......... .......... .......... ..........
N29508    .......... .......... .......... .......... ..........
N26919    .......... .......... .......... .......... ..........
N26910    .......... .......... .......... .......... ..........
H16757    .......... .......... .......... .......... ..........
N27732    .......... .......... .......... .......... ..........

951                                                      1000
Bikunin   GAA TCCTCC CCTGCCCCTT GGCTCAAAGG TGGTGGTTC TGG CGGGGC
R74593    GAA.TCCTCC CCTGCCCCTT GGCTCAAAGG TGGTGGTTC. TGGCCGGGGC
R31730    GAA.TCCTCC CCTGCCCCTT GGCTCAAAGG TGGTGGTTC. TGG.CGGGGC
R34701    AAANTCCTCC CCTCCCCCTT GGCTCAAAGG TGGTGGTTCC TGG.CGGGGC
H02982    GAA.TCCTCC CCTGCCCCTT GGCTCAAAGG TGGTGGTTC. TGG.CGGGGC
R32676    GAA.TCCTCC CCTGCCCCTT GGCTCAAAGG TGGTGGTTC. TGG.CGGGGC
T47439    GAA.TCCTCC CCTGCCCCTT GGCTCAAAGG TGGTGGTTC. TGG.CGGGGC
R73968    .......... .......... .......... .......... ....CGGGGC
H39840    .......... .......... .......... .......... ..........
H95233    .......... .......... .......... .......... ..........
H39841    .......... .......... .......... .......... ..........
N30199    .......... .......... .......... .......... ..........
T52966    .......... .......... .......... .......... ..........
N29508    .......... .......... .......... .......... ..........
N26919    .......... .......... .......... .......... ..........
N26910    .......... .......... .......... .......... ..........
H16757    .......... .......... .......... .......... ..........
N27732    .......... .......... .......... .......... ..........
```

FIG. 4C-16

```
            1001                                                          1050
Bikunin  TGTT CGTGA TGGTGTTGAT CC T CTTCC TGGG AGCCT CC ATGGTC
 R74593  TGTTTCGTGA TGGTGTTGAT CCTT..TTCC TGGGGAGCNT CC.ATGGTCT
 R31730  TGTT.CGTGA TGGTGTTGAT CC.T.CTTCC TGGGGAGCCT CC.ATGGTC.
 R34701  TGTT.CGTGA TGGTGTTGAT CCCTCCTTCC CGGG.AGCCT CCCATGGTCC
 H02982  TGTT.CGTGA TGGTGTTGAT CC.T.CTTCC TGGG.AGCCT CC.ATGGTN.
 R32676  TGTT.CGTGA TGGTGTTGAT CC.T.CTTCC TGGG.AGCCT CC.ATGGTC.
 T47439  TGTT.CGTGA TGGTGTTGAT CC.T.CTTCC TGGG.AGCCT CC.ATGGTC.
 R73968  TGTT.CGTGA TGGTGTTGAT CC.T.CTTCC TGGG.AGCCT CC.ATGGTC.
 H39840  .......... .......... .......... .......... ..........
 H95233  .......... .......... .......... .......... ..........
 H39841  .......... .......... .......... .......... ..........
 N30199  .......... .......... .......... .......... ..........
 T52966  .......... .......... .......... .......... ..........
 N29508  .......... .......... .......... .......... ..........
 N26919  .......... .......... .......... .......... ..........
 N26910  .......... .......... .......... .......... ..........
 H16757  .......... .......... .......... .......... ..........
 N27732  .......... .......... .......... .......... ..........

1051                                                          1100
Bikunin  TACC TGAT  CCGGGTGGCA CGGAGG AAC C AGG AGCG TGCCCTGCGC
 R74593  TAC..TGATT CCGGGTGGCA AGGAGG.AAC C.AGG.AGCG TGCCCTGCGG
 R31730  TACC.TGAT. CCGGGTGGCA CGGAGGGAAC C.AGGGAGCG TGCCCTGCGC
 R34701  TACCCTGAT. CCGGGTGGCA CGGAGG.AAC CCAGG.ANCG TGCCCTGCGC
 H02982  TACC.TGAT. CCGGGTNGCA CGGAGG.AAC C.AGGGAGCG TGCCCTGCGN
 R32676  TACC.TGAT. CCGGGTGGCA CGGAGG.AAC C.AGGGAGCG TGCCCTGCGC
 T47439  TACC.TGAT. CCGGGTNGCA CGGAGG.AAC C.AGG.AGCG TGCCCTGCGC
 R73968  TACC.TGAT. CCGGGTGGCA CGGAGG.AAC C.AGG.AGCG TGCCCTGCGC
 H39840  .......... .......... ...GGG.AAC C.AGG.AGCG TGCCCTGCGC
 H95233  .......... .......... .......... .......... ..........
 H39841  .......... .......... .......... .......... ..........
 N30199  .......... .......... ..GAGGAACC C.ANG.AGCT TCCCCTGCGC
 T52966  .......... .......... .......... .......... ..........
 N29508  .......... .......... .......... .......... ..........
 N26919  .......... .......... .......... .......... ..........
 N26910  .......... .......... .......... .......... ..........
 H16757  .......... .......... .......... .......... ..........
 N27732  .......... .......... .......... .......... ..........
```

FIG. 4C-17

```
         1101                                                    1150
Bikunin  ACCG TCT G  GAGCTCCGGA  GATGACAAGG   AGCAGCTGG   TGAAGAAC
R74593   ANCG.TCT.G  GAGCTTCGGA  GATGACAAGG  GNT
R31730   ACCG.TCTGG  GAGCTCCGGA  GATGACAAGG  GAGCAGCTGG  GTGAAGAAC.
R34701   ACCG.TCT.G  GAGCTCCGGA  GATGACAAGG  .AGCAGCTGG  .TGAAGAAC.
H02982   ACCG.TCTNG  GAGCTCCGGA  GATGACAAGG  .AGCAGCTGG  .TGAAGAAC.
R32676   ACCG.TCTGG  GAGCTCCGGA  GATGACAAGG  GAGCAGCTGG  .TGAAGAAC.
T47439   ACCG.TCT.G  GAGCTCCGGA  GATGACAAGG  .AGCAGCTGG  .TGAAGAAC.
R73968   ACCG.TCT.G  GAGCTCCGGA  GATGACAAGG  .AGCAGCTGG  .TGAAGAAC.
H39840   ACCGGTCT.G  GAGCTCCGGA  GATGACAAGG  .AGCAGCTGG  .TGAAGAAC.
H95233   ..........  ..........  ..........  ..........  ..........
H39841   ..........  ..........  ..........  ..........  ..........
N30199   ACCG.TCT.G  GAGCTCCGGA  GATNACAANG  .AGCAGCTGN  .TGAAGAACC
T52966   ..........  ..........  ..........  ..........  ..........
N29508   ..........  ..........  ..........  ..........  ..........
N26919   ..........  ..........  ..........  ..........  ..........
N26910   ..........  ..........  ..........  ..........  ..........
H16757   ..........  ..........  ..........  ..........  ..........
N27732   ..........  ..........  ..........  ..........  ..........

1151                                                    1200
Bikunin  ACATATGT C  CTGT GACCG  CCCTGT CGC  C AAGAGG A  CT GGGGAA
R31730   ACATATGTTC  CTGTTGACCG  NCCTGTTCGC  C.AAGAGG.A  TTGGGGGAA.
R34701   ACATATGT.C  CTGT.GACCG  CCCTGT.CGC  C.AAGAGG.A  CT.GGGGAA.
H02982   ACATATGT.C  CTGT.GACCG  NCCTGTTCGN  C.AAGAGG.A  CTNGGGGAAA
R32676   ACATATGTTC  CTGTTGACCG  CCCTGTTCGC  C.AAGAGGGA  NTGGGGGAA.
T47439   ACATATGT.C  CTGT.GACCG  CCCTGT.CGC  C.AAGAGG.A  CT.GGGGAA.
R73968   ACATATGT.C  CTGT.GACCG  CCCTGT.CGC  C.AAGAGG.A  CT.GGGGAA.
H39840   ACATATGT.C  CTGT.GACCG  CCCTGT.CGC  C.AAGAGG.A  CT.NGGGAA.
H95233   ..........  ..........  ..........  ..........  ..........
H39841   ..........  ........C.  CCCTGT.CGC  CCAAAAGG.A  CT.GGGGAA.
N30199   ACATATGT.C  CTGT.GACCG  CCCTNT.CGC  C.AAGAGG.A  CT.GGGNAAA
T52966   ..........  ..........  ..........  ..........  ..........
N29508   ..........  .......CC.  CCCTNT.CGC  C.AAGAGG.A  CT.GGG.AA.
N26919   ..........  ..........  ..........  ..........  ..........
N26910   ..........  ..........  ..........  ..........  ..........
H16757   ..........  ..........  ..........  ..........  ..........
N27732   ..........  ..........  ..........  ..........  ..........
```

FIG. 4C-18

```
          1201                                                    1250
Bikunin   GGGAGGGG   AGACTAT G   TGT GA GCT   TTTTTT     AA A TAGA    GG
R31730    .GGGAGGGGG  A
R34701    .GGGAGGGG.  AGACTAT.G.  TGT.GA.GCT   TTTTTT..AA  A.TA
H02982    GGGGAGGGG.  AGATTAT.G.  TGTTGA.GTT   TTTTTT..AA  ANTAG
R32676    GGGGAGGGGG  AGANTATTGT  TGTTGA.GNT   TTTTTTTAAA  ATTAGGAGGG
T47439    .GGGAGGGG.  AGACTAT.G.  TGT.GA.GCT   TTTTTT..AA  A.TAGA..GG
R73968    .GGGAGGGG.  AGACTAT.G.  TGT.GA.GCT   TTTTTT..AA  A.TAGA..GG
H39840    .GGGAGGGG.  AGACTAT.G.  TGT.GA.GCT   TTTTTT..AA  A.TAGA..GG
H95233    ..........  ..........  ..........   ..........  ..........
H39841    .GGGAGGGGA  AAACNAT.G.  TGT.GAACCT   TTTTTT.AAA  A.TAGA..GG
N30199    .GGGAGGNG.  AGACTAT.G.  TGT.AA.GCT   TTTTTT..AA  A.TAGA..GG
T52966    ..........  ..........  ..........   ..........  ..........
N29508    .GGGAGGGG.  AGACTA..G.  TGT.GA.GCT   TTTTTT..AA  A.TAGA..GG
N26919    ..........  ..........  ..........   ..........  ..........
N26910    ..........  ..........  ..........   ..........  ..........
H16757    ..........  ..........  ..........   ..........  ..........
N27732    ..........  ..........  ..........   ..........  ..........

1251                                                    1300
Bikunin   GATTGACTC   GGATTTG A   GT GATC A    TTAGGG  CT  GAGGTCTGTT
R32676    GNTTGANTTC  GGGNTTTTNA  GTTGATCCAT   TTAGGGGGNT  GAG
T47439    GATTGACTC.  .GGATTTG.A  GT.GATC.A.   TTAGGG..CT  GAGGTCTNTT
R73968    GATTGACTC.  .GGATTTG.A  GT.GATC.A.   TTAGGG..CT  GAGGTCTGTT
H39840    GATTGACTC.  .GGATTTG.A  GT.GATC.A.   TTAGGG..CT  GAGGTCTGTT
H95233    ..........  ..........  ........A.   TTAGGG..CT  GAGGTCTGTT
H39841    GATTGACTC.  .GGATTTG.A  GT.GATC.A.   TTAGGG..CT  GAGGTCTGTT
N30199    GATTGACTC.  .GGATTTGGA  GT.GATC.A.   TTAGGG..CT  GAGGTCTGTT
T52966    ..........  ..........  ..........   ..........  ..........
N29508    GATTGACTC.  .GGATTTG.A  GT.GATCNA.   TTAGGG..CT  GAGGTCTGTT
N26919    ..........  ..........  ..........   ..........  ..........
N26910    ..........  ..........  ..........   ..........  ..........
H16757    ..........  ..........  ..........   ..........  ..........
N27732    ..........  ..........  ..........   ..........  ..........

1301                                                    1350
Bikunin   TCTCTGGGAG  GTAGGACGGC  TGCTTCC TG   G TC TGGCA  GGGATGGG
T47439    TCTCTNGGAG  GTAGGACGA
R73968    TCTCTGGGAG  GTAGGACGGC  TGCTTCC.TG   GGTCTTGGCA  .GGGATGGGG
H39840    TCTCTGGGAG  GTAGGACGGC  TGCTTCC.TG   G.TC.TGGCA  .GGGATGGG.
H95233    NCTCTGGGAG  NTAGGACGGC  TGCCTTCCTG   G.TC.TGGCA  .GGGATGGG.
H39841    TCNCTGGGAG  GTAGGACGGC  TGCTCCCCTG   G.TC.TGGCA  .GGGATGGG.
N30199    TCTCTGGGAG  GTAGGACGGC  TGCTTCC.TG   G.TC.TGGCA  .GGGATGGG.
T52966    ..........  ..........  ..........   ..TC.TGGCA  .GGGATGGG.
N29508    TCTCTGGGAG  GTAGGACGGC  TGCTTCA.TG   G.TC.TGGCA  .GGGATGGG.
N26919    ..........  ..........  ..........   ..........  ..........
N26910    ..........  ..........  ..........   ..........  ..........
H16757    ..........  ..........  .........G   G.TC.TGGCA  .GGGATGGG.
N27732    ..........  ..........  .....CCCTG   GGTCCTGNCA  AGGNATGGGG
```

FIG. 4C-19

```
             1351                                                  1400
Bikunin   TTTG CTTTG  G AAATCCTC  T AGGAGGCT  CCTCCT CGC ATGG CC TG
R73968    TTTG.CTTTG  GGAAATCCTC  TTNGGAGGCT  CCTCCTTCGC ATGGGCCTTG
H39840    TTTG.CTTTG  GAGAATCCTC  T.ANGAGGCT  CCTCCT.CGC ATGG.CC.TG
H95233    TTTG.CTTTG  G.AAATCCTC  T.AGGAGGCT  CCTCCT.CGC ATGG.CC.TG
H39841    TTTG.CTTTG  G.AAANCCNC  T.AGGAGGCT  CCTCCT.CGC ATGG.CC.TG
N30199    TTTG.CTTTG  G.AAATCCTC  T.AGGAGGCT  CCTCCTTCGC ATGG.CC.TG
T52966    TTTG.CTTTG  G.AAATCCTC  T.AGGAGGCT  CCTCCT.CGC ATGG.CC.TG
N29508    TTTG.CTTTG  G.AAATCCTC  T.AGGAGGCT  CCTCCT.CGC ATGG.CC.TG
N26919    ..........  ..........  ....GAGGCT  CCTCCT.CGC ATGG.CC.TG
N26910    .....CTTTT  GNAAATCCTC  T.AGGAGGCT  CCTCCT.CGC ATGG.CC.TG
H16757    TTTGCCTTTG  G.AAANCCTC  T.AGGAGGCT  CCTCCT.CGC ATGG.CC.TG
N27732    TTTG.CTTTG  G.AAATCCTC  TTAGGAGGCT  CCTCCT.CGC ATGG.CC.TG 1401                                                  1450
Bikunin   CAGT CT GG  CAGCAG CCC  CGAGTTGTTT  CC TCGCTG ATC GATTTC
R73968    CAGT.CTNGG  CAGCANCCCC  CGAGTTTTTT  TCCTTCGCTG ATCCGATTTC
H39840    CAGT.CT.GG  CAGCAG.CCC  CGAGTTGTTT  .CC.TCGCTG ATC.GATTTC
H95233    CAGTTCT..G  CAGCAG.CCC  CGAGTTGTTT  .CC.TCGCTG ATC.GATTTC
H39841    CAGT.CT.GG  CAGCAG.CCC  CGAGTTGTTN  .CC.TCGCTG ATC.GATNTC
N30199    CAGT.CT.GG  CAGCAG.CCC  CGAGTTGTTT  .CC.TCGCTG ATC.GATTTC
T52966    CAGT.CT.GG  CAGCAG..CC  CGAGTTGTTT  .CC.TCGCTG ATC.GATTTC
N29508    CAGT.CT..G  CAGCAG.CCC  CGAGTTGTTT  .CC.TCGCTG ATC.GATTTC
N26919    CAGT.CTTGG  CAGCAG.CCC  CGAGTTGTTT  .CC.TCGCTG ANC.GATTTC
N26910    CAGT.CT..G  CAGCAG.CCC  CGAGTTGTTT  .CC.TCGCTG ATCGGATTTC
H16757    CAGTNCT.GG  CAGCAGACCC  CGAGTTGTTT  .CC.TCGCTG ATC.GATTTC
N27732    CAGT.CT.GG  CAGCAG.CCC  CGAGTTGTTT  .CC.TCGCTG ANC.GATTTC 1451                                                  1500
Bikunin   TTT CCTCCA  GGTAG  AGT  TTTC TTTG   CTTATGTTGA ATTCCATTGC
R73968    TTTTCCTCCA  GGTAAGAATT  TTTCTTTT
H39840    TTT.CCTCCA  GGTAG..AGT  TTTC.TTTG.  CTTATGTTGA ATTCCATTGC
H95233    TTT.CCTCCA  GGTAG..AGT  TTTC.TTTG.  CTTATGTTGA ATTCCATTGC
H39841    TTT.CCCCCA  GGTAG..AGT  TTTC.TTTG.  CTTATGTTGA ANTCCATTGC
N30199    TTT.CCTCCA  GGTAG..AGT  TTTC.TTTG.  CTTATGTTGA ATTCCATTGC
T52966    TTT.CCTCCA  GGTAG..AGT  TTTC.TTTG.  CTTATGTTGA ATTCCATTGC
N29508    TTT.CCTCCA  GGTAG..AGT  TTTC.TTTG.  CTTATGTTGA ATTCCATTGC
N26919    TTT.CCNCCA  GGTAG..AGT  TTTC.TTTG.  CTTATGTTGA ATTCCATTGC
N26910    TTT.CCTCCA  GGTAG..AGT  TTTC.TTTG.  CTTATGTTGA ATTCCATTGC
H16757    TTTACCCCCA  GGTAG..AGT  TTTCCTTTGN  CTTATGTTGA ATTCCATTGC
N27732    TTT.CCTCCA  GGTAG..AGT  TTTC.TTTG.  CTTATGTTGA ATTCCATTGC
```

FIG. 4C-20

```
          1501                                                    1550
Bikunin   CTCTTTT CT CATCACAGAA GTGATGTTGG AATCGTTTCT TTTGTTT GT
H39840    CTCTTTT.CT CATCACAGAA GTGATGTTGG AATCGTTTCT TTTGTTTTGT
H95233    CTCTTTT.CT CATCACAGAA GTGATGTTGG AATCGTTTCT TTTGTTT.GT
H39841    CTCTTTT.CT CATCACAGAA GTGATGTTGG AATCGTTTCT TTTGTTT.GT
N30199    CTCTTTT.CT CATCACAGAA GTGATGTTGG AATCGTTTCT TTTGTTT.GT
T52966    CTCTTTT.CT CATCACAGAA GTGATGTTGG AATCGTTTCT TTTGTTT.GT
N29508    CTCTTTT.CT CATCACAGAA GTGATGTTGG AATCGTTTCT TTTGTTT.GT
N26919    CTCTTTT.CN CATCACAGAA GTGATGTTGG AATCGTTTCT TTTGTTT.GT
N26910    CTCTTTT.CT CATCACAGAA GTGATGTTGG AATCGTTTCT TTTGTTT.GT
H16757    CTCTTTTACT CATCACAGAA GTGATGTTGG AATCGTTTCT TTTGTTT.GT
N27732    CTCTTTT.CT CATCACAGAA GTGATGTTGG AATCGTTTCT TTTGTTT.GT 1551                                                    1600
Bikunin   CTGATTTATG G   TTTTTTT AAGTATAAAC AAAAGTTTTT TATTAGCATT
H39840    CTGATTTATG GGTTTTTTTT AAGTAT
H95233    CTGATTTATG G..TTTTTTT AAGTATAAAC AAAAGTTTTT TATTAGCATT
H39841    CTGATTTATG G..TTTTTTT AAGTATAAAC AAAAGTTTTT TATTAGCATT
N30199    CTGATTTATG G..TTTTTTT AAGTATAAAC AAAAGTTTTT TATTAGCATT
T52966    CTGATTTATG G..TTTTTTT AAGTATAAAC AAAAGTTTTT TATTAGCATT
N29508    CTGATTTATG G..TTTTTTT AAGTATAAAC AAAAGTTTTT TATTAGCATT
N26919    CTGATTTATG G..TTTTTTT AAGTNTAAAC AAAAGTTTTT TATTAGCATT
N26910    CTGATTTATG G..TTTTTTT AAGTATAAAC AAAAGTTTTT TATTAGCATT
H16757    CTGATTTATG G..TTTTTTT AAGTATAAAC AAAAGTTTTT TATTAGCATT
N27732    CTGATTTATG G..TTTTTTT AAGTATAAAC AAAAGTTTTT TATTAGCATT 1601                                                    1650
Bikunin   CTGAAAGAAG GAAAGTAAAA TGTACAAGTT TAATAAAAAG GGGCCTTCCC
H95233    CTGAAAGAAG GAAAGTAAAA TGTACAAGTT TAATAAA
H39841    CTGAAAGAAG GAAAGTAAAN TGTACAAGTT TAATAAAAAG GGGCCTTCCC
N30199    CTGAAAGAAG GAAAGTAAAA TGTACAAGTT TAATAAAAAG GGGCCTTCCC
T52966    CTGAAAGAAG GAAAGTAAAA TGTACAAGTT TAATAAAAAG GGGCCTTCCC
N29508    CTGAAAGAAG GAAAGTAAAA TGTACAAGTT TAATAAAAAG GGGCCTTCCC
N26919    CTGAAAGAAG GAAAGTAAAA TGTACAAGTT TAATAAAAAG GGGCCTTCCC
N26910    CTGAAAGAAG GAAAGTAAAA TGTACAAGTT TAATAAAAAG GGGCCTTCCC
H16757    CTGAAAGAAG GAAAGTAAAA TGTACAAGTT TAATAAAAAG GGGCCTTCCC
N27732    CTGAAAGAAG GAAAGTAAAA TGTACAAGTT TAATAAAAAG GGGCCTTCCC 1651                              1689
Bikunin   CTTTAG AAT AAAAAAAAAA AAAAAAAAA AAAAAAAA
H39841    CTTTAA.
N30199    CTTTAG.AAT AAA
T52966    CTTTAGGAAT NAAAANAAAA AAGGGTG
N29508    CTTTAG.AAT AAATTTCAGC ATGTGCTTTC AA
N26919    CTTTAG.AAT AAAAAAAAAA AAAAAAAAA A
N26910    CTTTAG.AAT AAATTTCAGC ATGTGCTTTC AAAAAA
H16757    CTTTAG.AAT AAAAAAAAAA AAAAAAAAA AAAAA
N27732    CTTTAG.AAT AAAAAAAAAA AAAAAAAAA AAAAAAAA
```

FIG. 4D

```
EST consens  MLRAEADGVS RLLGSLLLSG VLAADRERSI HDFCLVSKVV GRCRASMPRW   50
EST consens  WYNVTDGSCQ LFVYGGCDGN SNNYLTKEEC LKKCATVTEN ATGDLATSRN  100
EST consens  AADSSVPSAP RRQDSEDHSS DMFNYEEYCT ANAVTGPCRA SFPRWYFDVE  150
EST consens  RNSCNNFIYG GCRGNKNSYR SEEACMLRCF RQQENPPLPL GSKVVVLAGL  200
EST consens  FVMVLILFLG ASMVYLIRVA RRNQERALRT VWSSGDDKEQ LVKNTYVL    248
```

FIG. 4E

```
cDNA                                                                           ACC     3
translation                                                                      T    -47 cDNA          TGATCGCGAG ACCCCAACGG CTGGTGGCGT CGCCTGCGCG TCTCGGCTGA             53
translation  .  S   R   D     P   N   G     W   W   R     R   L   R   V     S   A   E  -30 cDNA          GCTGGCCATG GCGCAGCTGT GCGGGCTGAG GCGGAGCCGG GCGTTTCTCG            103
translation   L   A   M     A   Q   L   C     G   L   R     R   S   R     A   F   L  -13 cDNA          CCCTGCTGGG ATCGCTGCTC CTCTCTGGGG TCCTGGCGGC CGACCGAGAA            153
translation   L   L   G     S   L   L     L   S   G   V     L   A   A     D   R   E    4 cDNA          CGCAGCATCC ACGACTTCTG CCTGGTGTCG AAGGTGGTGG GCAGATGCCG            203
translation  R   S   I     H   D   F   C     L   V   S     K   V   V   G     R   C   R     21 cDNA          GGCCTCCATG CCTAGGTGGT GGTACAATGT CACTGACGGA TCCTGCCAGC            253
translation  A   S   M     P   R   W   W     Y   N   V     T   D   G     S   C   Q   L     38 cDNA          TGTTTGTGTA TGGGGGCTGT GACGGAAACA GCAATAATTA CCTGACCAAG            303
translation    F   V   Y     G   G   C     D   G   N   S     N   N   Y     L   T   K     54 cDNA          GAGGAGTGCC TCAAGAAATG TGCCACTGTC ACAGAGAATG CCACGGGTGA            353
translation  E   E   C   L     K   K   C     A   T   V     T   E   N   A     T   G   D     71 cDNA          CCTGGCCACC AGCAGGAATG CAGCGGATTC CTCTGTCCCA AGTGCTCCCA            403
translation  L   A   T     S   R   N   A     A   D   S     S   V   P     S   A   P   R     88 cDNA          GAAGGCAGGA TTCTGAAGAC CACTCCAGCG ATATGTTCAA CTATGAAGAA            453
translation   R   Q   D     S   E   D     H   S   S   D     M   F   N     Y   E   E    104 cDNA          TACTGCACCG CCAACGCAGT CACTGGGCCT TGCCGTGCAT CCTTCCCACG            503
translation  Y   C   T     A   N   A   V     T   G   P     C   R   A   S     F   P   R    121 cDNA          CTGGTACTTT GACGTGGAGA GGAACTCCTG CAATAACTTC ATCTATGGAG            553
translation  W   Y   F     D   V   E   R     N   S   C     N   N   F     I   Y   G    138 cDNA          GCTGCCGGGG CAATAAGAAC AGCTACCGCT CTGAGGAGGC CTGCATGCTC            603
translation    C   R   G     N   K   N     S   Y   R   S     E   E   A     C   M   L    154 cDNA          CGCTGCTTCC GCCAGCAGGA GAATCCTCCC CTGCCCCTTG GCTCAAAGGT            653
translation  R   C   F   R     Q   Q   E     N   P   P     L   P   L   G     S   K   V    171 cDNA          GGTGGTTCTG GCGGGGCTGT TCGTGATGGT GTTGATCCTC TTCCTGGGAG            703
translation   V   V   L     A   G   L   F     V   M   V     L   I   L     F   L   G   A    188 cDNA          CCTCCATGGT CTACCTGATC CGGGTGGCAC GGAGGAACCA GGAGCGTGCC            753
translation   S   M   V     Y   L   I     R   V   A   R     R   N   Q     E   R   A    204 cDNA          CTGCGCACCG TCTGGAGCTT CGGAGATGA                                   782
translation  L   R   T     V   W   S   F     G   D                                      213
```

FIG. 4F-1

```
cDNA         GCACGAGTTG GGAGGTGTAG CGCGGCTCTG AACGCGCTGA GGGCCGTTGA   50
cDNA         GTGTCGCAGG CGGCGAGGGC GCGAGTGAGG AGCAGACCCA GGCATCGCGC  100
cDNA         GCCGAGAAGG CCGGCGTCC CCACACTGAA GGTCCGGAAA GGCGACTTCC  150
cDNA         GGGGGCTTTG GCACCTGGCG GACCCTCCCG GAGCGTCGGC ACCTGAACGC  200
cDNA         GAGGCGCTCC ATTGCGCGTG CGCGTTGAGG GGCTTCCCGC ACCTGATCGC  250
cDNA         GAGACCCCAA CGGCTGGTGG CGTCGCCTGC GCGTCTCGGC TGAGCTGGCC  300
cDNA         ATGGCGCAGC TGTGCGGGCT GAGGCGGAGC CGGGCGTTTC TCGCCCTGCT  350
translation  M  A  Q  L    C  G  L    R  R  S    R  A  F    L  A  L   -11 cDNA         GGGATCGCTG CTCCTCTCTG GGGTCCTGGC GGCCGACCGA GAACGCAGCA  400
translation  G  S  L    L  L  S    G  V  L    A  A  D  R    E  R  S  I   7 cDNA         TCCACGACTT CTGCCTGGTG TCGAAGGTGG TGGGCAGATG CCGGGCCTCC  450
translation  H  D  F    C  L  V    S  K  V  V    G  R  C    R  A  S   23 cDNA         ATGCCTAGGT GGTGGTACAA TGTCACTGAC GGATCCTGCC AGCTGTTTGT  500
translation  M  P  R  W    W  Y  N    V  T  D    G  S  C    Q  L  F  V   40 cDNA         GTATGGGGGC TGTGACGGAA ACAGCAATAA TTACCTGACC AAGGAGGAGT  550
translation  Y  G  G    C  D  G  N    S  N  N    Y  L  T    K  E  E  C   57 cDNA         GCCTCAAGAA ATGTGCCACT GTCACAGAGA ATGCCACGGG TGACCTGGCC  600
translation  L  K  K    C  A  T    V  T  E  N    A  T  G    D  L  A   73 cDNA         ACCAGCAGGA ATGCAGCGGA TTCCTCTGTC CCAAGTGCTC CCAGAAGGCA  650
translation  T  S  R  N    A  A  D    S  S  V    P  S  A  P    R  R  Q   90 cDNA         GGATTCTGAA GACCACTCCA GCGATATGTT CAACTATGAA GAATACTGCA  700
translation  D  S  E    D  H  S  S    D  M  F    N  Y  E    E  Y  C  T  107 cDNA         CCGCCAACGC AGTCACTGGG CCTTGCCGTG CATCCTTCCC ACGCTGGTAC  750
translation  A  N  A    V  T  G    P  C  R  A    S  F  P    R  W  Y  123 cDNA         TTTGACGTGG AGAGGAACTC CTGCAATAAC TTCATCTATG GAGGCTGCCG  800
translation  F  D  V  E    R  N  S    C  N  N    F  I  Y  G    G  C  R  140 cDNA         GGGCAATAAG AACAGCTACC GCTCTGAGGA GGCCTGCATG CTCCGCTGCT  850
translation  G  N  K    N  S  Y  R    S  E  E    A  C  M    L  R  C  F  157 cDNA         TCCGCCAGCA GGAGAATCCT CCCCTGCCCC TTGGCTCAAA GGTGGTGGTT  900
translation  R  Q  Q    E  N  P    P  L  P  L    G  S  K    V  V  V  173 cDNA         CTGGCGGGGC TGTTCGTGAT GGTGTTGATC CTCTTCCTGG GAGCCTCCAT  950
translation  L  A  G  L    F  V  M    V  L  I    L  F  L    G  A  S  M  190 cDNA         GGTCTACCTG ATCCGGGTGG CACGGAGGAA CCAGGAGCGT GCCCTGCGCA 1000
translation  V  Y  L    I    R  V  A    R  R  N    Q  E  R    A  L  R  T  207 cDNA         CCGTCTGGAG CTCCGGAGAT GACAAGGAGC AGCTGGTGAA GAACACATAT 1050
translation  V  W  S    S  G  D    D  K  E  Q    L  V  K    N  T  Y  223 cDNA         GTCCTGTGAC CGCCCTGTCG CCAAGAGGAC TGGGGAAGGG AGGGGAGACT 1100
translation  V  L  *                                                  225
```

FIG. 4F-2

```
cDNA        ATGTGTGAGC TTTTTTTAAA TAGAGGGATT GACTCGGATT TGAGTGATCA 1150
cDNA        TTAGGGCTGA GGTCTGTTTC TCTGGGAGGT AGGACGGCTG CTTCCTGGTC 1200
cDNA        TGGCAGGGAT GGGTTTGCTT TGGAAATCCT CTAGGAGGCT CCTCCTCGCA 1250
cDNA        TGGCCTGCAG TCTGGCAGCA GCCCCGAGTT GTTTCCTCGC TGATCGATTT 1300
cDNA        CTTTCCTCCA GGTAGAGTTT TCTTTGCTTA TGTTGAATTC CATTGCCTCC 1350
cDNA        TTTTCTCNAT CACAGAAGTG ATGTTGGAAT CGTTTCTTTT GTTTGTCTGA 1400
cDNA        TTTATGGTTT TTTTAAGTAT AAACAAAAGT TTTTTATTAG CATTCTGAAA 1450
cDNA        GAAGGAAAGT AAAATGTACA AGTTTAATAA AAAGGGGCCT TCCCCTTTAG 1500
cDNA        AATAAATTTC CAGCATGTTG CTTCAAAAA AAAAAAAAA AAAA
1550
```

FIG. 4G

```
EST consens                             MLR AEADGVSRLL GSLLLSGVLA  -1
PCR clone                        MAQLCGL RRSRAFLALL GSLLLSGVLA  -1
λcDNA clone                      MAQLCGL RRSRAFLALL GSLLLSGVLA  -1

EST consens ADRERSIHDF CLVSKVVGRC RASMPRWWYN VTDGSCQLFV YGGCDGNSNN  50
PCR clone   ADRERSIHDF CLVSKVVGRC RASMPRWWYN VTDGSCQLFV YGGCDGNSNN  50
λcDNA clone ADRERSIHDF CLVSKVVGRC RASMPRWWYN VTDGSCQLFV YGGCDGNSNN  50

EST consens YLTKEECLKK CATVTENATG DLATSRNAAD SSVPSAPRRQ DSEDHSSDMF 100
PCR clone   YLTKEECLKK CATVTENATG DLATSRNAAD SSVPSAPRRQ DSEDHSSDMF 100
λcDNA clone YLTKEECLKK CATVTENATG DLATSRNAAD SSVPSAPRRQ DSEDHSSDMF 100

EST consens NYEEYCTANA VTGPCRASFP RWYFDVERNS CNNFIYGGCR GNKNSYRSEE 150
PCR clone   NYEEYCTANA VTGPCRASFP RWYFDVERNS CNNFIYGGCR GNKNSYRSEE 150
λcDNA clone NYEEYCTANA VTGPCRASFP RWYFDVERNS CNNFIYGGCR GNKNSYRSEE 150

EST consens ACMLRCFRQQ ENPPLPLGSK VVVLAGLFVM VLILFLGASM VYLIRVARRN 200
PCR clone   ACMLRCFRQQ ENPPLPLGSK VVVLAGLFVM VLILFLGASM VYLIRVARRN 200
λcDNA clone ACMLRCFRQQ ENPPLPLGSK VVVLAGLFVM VLILFLGASM VYLIRVARRN 200

EST consens QERALRTVWS SGDDKEQLVK NTYVL                            225
PCR clone   QERALRTVWS FGD                                        213
λcDNA clone QERALRTVWS SGDDKEQLVK NTYVL                            225
```

Purification of Placental Bikunin using C18 Reverse-Phase Chromatography

```
                          SEQUENCE LISTING (1) GENERAL INFORMATION:

(iii) NUMBER OF SEQUENCES: 71

(2) INFORMATION FOR SEQ ID NO:1:

(i) SEQUENCE CHARACTERISTICS:
         (A) LENGTH: 179 amino acids
         (B) TYPE: amino acid
         (C) STRANDEDNESS: Not Relevant
         (D) TOPOLOGY: unknown (ii) MOLECULE TYPE: peptide (xi) SEQUENCE DESCRIPTION: SEQ ID NO:1:

Ala Asp Arg Glu Arg Ser Ile His Asp Phe Cys Leu Val Ser Lys Val
 1               5                  10                  15

Val Gly Arg Cys Arg Ala Ser Met Pro Arg Trp Trp Tyr Asn Val Thr
                20                  25                  30

Asp Gly Ser Cys Gln Leu Phe Val Tyr Gly Gly Cys Asp Gly Asn Ser
            35                  40                  45

Asn Asn Tyr Leu Thr Lys Glu Glu Cys Leu Lys Lys Cys Ala Thr Val
        50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
        115                 120                 125

Asn Ser Cys Asn Asn Phe Ile Tyr Gly Gly Cys Arg Gly Asn Lys Asn
    130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Val Leu Ala Gly
                165                 170                 175

Ala Val Ser (2) INFORMATION FOR SEQ ID NO:2:

(i) SEQUENCE CHARACTERISTICS:
         (A) LENGTH: 197 amino acids
         (B) TYPE: amino acid
         (C) STRANDEDNESS: Not Relevant
         (D) TOPOLOGY: unknown (ii) MOLECULE TYPE: peptide
```

(ix) FEATURE:
              (A) NAME/KEY: Region
              (B) LOCATION: 1..18
              (D) OTHER INFORMATION: /label= signalpeptide (xi) SEQUENCE DESCRIPTION: SEQ ID NO:2:

Ala Gly Ser Phe Leu Ala Trp Leu Gly Ser Leu Leu Ser Gly Val
1               5                   10                  15

Leu Ala Ala Asp Arg Glu Arg Ser Ile His Asp Phe Cys Leu Val Ser
            20                  25                  30

Lys Val Val Gly Arg Cys Arg Ala Ser Met Pro Arg Trp Trp Tyr Asn
                35                  40                  45

Val Thr Asp Gly Ser Cys Gln Leu Phe Val Tyr Gly Gly Cys Asp Gly
    50                  55                  60

Asn Ser Asn Asn Tyr Leu Thr Lys Glu Glu Cys Leu Lys Lys Cys Ala
65                  70                  75                  80

Thr Val Thr Glu Asn Ala Thr Gly Asp Leu Ala Thr Ser Arg Asn Ala
                85                  90                  95

Ala Asp Ser Ser Val Pro Ser Ala Pro Arg Arg Gln Asp Ser Glu Asp
                100                 105                 110

His Ser Ser Asp Met Phe Asn Tyr Glu Glu Tyr Cys Thr Ala Asn Ala
            115                 120                 125

Val Thr Gly Pro Cys Arg Ala Ser Phe Pro Arg Trp Tyr Phe Asp Val
    130                 135                 140

Glu Arg Asn Ser Cys Asn Asn Phe Ile Tyr Gly Gly Cys Arg Gly Asn
145                 150                 155                 160

Lys Asn Ser Tyr Arg Ser Glu Glu Ala Cys Met Leu Arg Cys Phe Arg
                165                 170                 175

Gln Gln Glu Asn Pro Pro Leu Pro Leu Gly Ser Lys Val Val Val Leu
            180                 185                 190

Ala Gly Ala Val Ser
            195

(2) INFORMATION FOR SEQ ID NO:3:

(i) SEQUENCE CHARACTERISTICS:
              (A) LENGTH: 153 amino acids
              (B) TYPE: amino acid
              (C) STRANDEDNESS: Not Relevant
              (D) TOPOLOGY: unknown (ii) MOLECULE TYPE: peptide (xi) SEQUENCE DESCRIPTION: SEQ ID NO:3:

Ile His Asp Phe Cys Leu Val Ser Lys Val Val Gly Arg Cys Arg Ala
1               5                   10                  15

Ser Met Pro Arg Trp Trp Tyr Asn Val Thr Asp Gly Ser Cys Gln Leu
            20                  25                  30

Phe Val Tyr Gly Gly Cys Asp Gly Asn Ser Asn Asn Tyr Leu Thr Lys
                35                  40                  45

Glu Glu Cys Leu Lys Lys Cys Ala Thr Val Thr Glu Asn Ala Thr Gly
    50                  55                  60

Asp Leu Ala Thr Ser Arg Asn Ala Ala Asp Ser Ser Val Pro Ser Ala
65                  70                  75                  80

Pro Arg Arg Gln Asp Ser Glu Asp His Ser Ser Asp Met Phe Asn Tyr
                85                  90                  95

Glu Glu Tyr Cys Thr Ala Asn Ala Val Thr Gly Pro Cys Arg Ala Ser

```
                      100                 105                 110
Phe Pro Arg Trp Tyr Phe Asp Val Glu Arg Asn Ser Cys Asn Asn Phe
            115                 120                 125
Ile Tyr Gly Gly Cys Arg Gly Asn Lys Asn Ser Tyr Arg Ser Glu Glu
            130                 135                 140
Ala Cys Met Leu Arg Cys Phe Arg Gln
145                 150
```

(2) INFORMATION FOR SEQ ID NO:4:

(i) SEQUENCE CHARACTERISTICS:
        (A) LENGTH: 58 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:4:

```
Ile His Asp Phe Cys Leu Val Ser Lys Val Val Gly Arg Cys Arg Ala
1               5                   10                  15
Ser Met Pro Arg Trp Trp Tyr Asn Val Thr Asp Gly Ser Cys Gln Leu
            20                  25                  30
Phe Val Tyr Gly Gly Cys Asp Gly Asn Ser Asn Asn Tyr Leu Thr Lys
            35                  40                  45
Glu Glu Cys Leu Lys Lys Cys Ala Thr Val
            50                  55
```

(2) INFORMATION FOR SEQ ID NO:5:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:5:

```
Cys Leu Val Ser Lys Val Val Gly Arg Cys Arg Ala Ser Met Pro Arg
1               5                   10                  15
Trp Trp Tyr Asn Val Thr Asp Gly Ser Cys Gln Leu Phe Val Tyr Gly
            20                  25                  30
Gly Cys Asp Gly Asn Ser Asn Asn Tyr Leu Thr Lys Glu Glu Cys Leu
            35                  40                  45
Lys Lys Cys
    50
```

(2) INFORMATION FOR SEQ ID NO:6:

(i) SEQUENCE CHARACTERISTICS:
        (A) LENGTH: 58 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:6:

```
Tyr Glu Glu Tyr Cys Thr Ala Asn Ala Val Thr Gly Pro Cys Arg Ala
1               5                   10                  15
Ser Phe Pro Arg Trp Tyr Phe Asp Val Glu Arg Asn Ser Cys Asn Asn
            20                  25                  30
```

```
Phe Ile Tyr Gly Gly Cys Arg Gly Asn Lys Asn Ser Tyr Arg Ser Glu
         35                  40                  45

Glu Ala Cys Met Leu Arg Cys Phe Arg Gln
 50                  55
```

(2) INFORMATION FOR SEQ ID NO:7:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:7:

```
Cys Thr Ala Asn Ala Val Thr Gly Pro Cys Arg Ala Ser Phe Pro Arg
 1               5                  10                  15

Trp Tyr Phe Asp Val Glu Arg Asn Ser Cys Asn Asn Phe Ile Tyr Gly
                 20                  25                  30

Gly Cys Arg Gly Asn Lys Asn Ser Tyr Arg Ser Glu Glu Ala Cys Met
         35                  40                  45

Leu Arg Cys
 50
```

(2) INFORMATION FOR SEQ ID NO:8:

(i) SEQUENCE CHARACTERISTICS:
        (A) LENGTH: 92 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:8:

```
Ala Asp Arg Glu Arg Ser Ile His Asp Phe Cys Leu Val Ser Lys Val
 1               5                  10                  15

Val Gly Arg Cys Arg Ala Ser Met Pro Arg Trp Trp Tyr Asn Val Thr
                 20                  25                  30

Asp Gly Ser Cys Gln Leu Phe Val Tyr Gly Gly Cys Asp Gly Asn Ser
         35                  40                  45

Asn Asn Tyr Leu Thr Lys Glu Glu Cys Leu Lys Lys Cys Ala Thr Val
 50                  55                  60

Thr Glu Asn Ala Thr Gly Asp Leu Ala Thr Ser Arg Asn Ala Ala Asp
 65                  70                  75                  80

Ser Ser Val Pro Ser Ala Pro Arg Arg Gln Asp Ser
                 85                  90
```

(2) INFORMATION FOR SEQ ID NO:9:

(i) SEQUENCE CHARACTERISTICS:
        (A) LENGTH: 708 base pairs
        (B) TYPE: nucleic acid
        (C) STRANDEDNESS: single
        (D) TOPOLOGY: Not Relevant (ii) MOLECULE TYPE: DNA (genomic)

(ix) FEATURE:
        (A) NAME/KEY: misc_feature
        (B) LOCATION: 679..708
        (D) OTHER INFORMATION: /note= "residues 679, 707 are any
            nucleic acid"

(xi) SEQUENCE DESCRIPTION: SEQ ID NO:9:

```
GGCCGGGTCG TTTCTCGCCT GGCTGGGATC GCTGCTCCTC TCTGGGGTCC TGGCGGCCGA    60
CCGAGAACGC AGCATCCACG ACTTCTGCCT GGTGTCGAAG GTGGTGGGCA GATGCCGGGC   120
CTCCATGCCT AGGTGGTGGT ACAATGTCAC TGACGGATCC TGCCAGCTGT TTGTGTATGG   180
GGGCTGTGAC GGAAACAGCA ATAATTACCT GACCAAGGAG GAGTGCCTCA AGAAATGTGC   240
CACTGTCACA GAGAATGCCA CGGGTGACCT GGCCACCAGC AGGAATGCAG CGGATTCCTC   300
TGTCCCAAGT GCTCCCAGAA GGCAGGATTC TGAAGACCAC TCCAGCGATA TGTTCAACTA   360
TGAAGAATAC TGCACCGCCA ACGCAGTCAC TGGGCCTTGC CGTGCATCCT TCCCACGCTG   420
GTACTTTGAC GTGGAGAGGA ACTCCTGCAA TAACTTCATC TATGGAGGCT GCCGGGGCAA   480
TAAGAACAGC TACCGCTCTG AGGAGGCCTG CATGCTCCGC TGCTTCCGCC AGCAGGAGAA   540
TCCTCCCCTG CCCCTTGGCT CAAAGGTGGT GGTTCTGGCC GGGGCTGTTT CGTGATGGTG   600
TTGATCCTTT TCCTGGGGAG CATCCATGGT CTTACTGATT CCGGGTGGCA AGGAGGAACC   660
AGGAGCGTGC CCTGCGGAAC GTCTGGAGCT TCGGAGATGA CAAGGGAT              708
```

(2) INFORMATION FOR SEQ ID NO:10:

(i) SEQUENCE CHARACTERISTICS:
        (A) LENGTH: 235 amino acids
        (B) TYPE: amino acid
        (C) STRANDEDNESS: Not Relevant
        (D) TOPOLOGY: unknown (ii) MOLECULE TYPE: peptide (ix) FEATURE:
        (A) NAME/KEY: Peptide
        (B) LOCATION: 1..235
        (D) OTHER INFORMATION: /note= "x is nonsense codon no
            amino acid, or stop codon"

(xi) SEQUENCE DESCRIPTION: SEQ ID NO:10:

```
Ala Gly Ser Phe Leu Ala Trp Leu Gly Ser Leu Leu Ser Gly Val
 1               5                  10                  15

Leu Ala Ala Asp Arg Glu Arg Ser Ile His Asp Phe Cys Leu Val Ser
                20                  25                  30

Lys Val Gly Arg Cys Arg Ala Ser Met Pro Arg Trp Trp Tyr Asn
                35                  40                  45

Val Thr Asp Gly Ser Cys Gln Leu Phe Val Tyr Gly Gly Cys Asp Gly
 50                  55                  60

Asn Ser Asn Asn Tyr Leu Thr Lys Glu Glu Cys Leu Lys Lys Cys Ala
65                   70                  75                  80

Thr Val Thr Glu Asn Ala Thr Gly Asp Leu Ala Thr Ser Arg Asn Ala
                85                  90                  95

Ala Asp Ser Ser Val Pro Ser Ala Pro Arg Arg Gln Asp Ser Glu Asp
               100                 105                 110

His Ser Ser Asp Met Phe Asn Tyr Glu Glu Tyr Cys Thr Ala Asn Ala
          115                 120                 125

Val Thr Gly Pro Cys Arg Ala Ser Phe Pro Arg Trp Tyr Phe Asp Val
          130                 135                 140

Glu Arg Asn Ser Cys Asn Asn Phe Ile Tyr Gly Gly Cys Arg Gly Asn
145                 150                 155                 160

Lys Asn Ser Tyr Arg Ser Glu Glu Ala Cys Met Leu Arg Cys Phe Arg
               165                 170                 175
```

```
Gln Gln Glu Asn Pro Pro Leu Pro Leu Gly Ser Lys Val Val Val Leu
            180                 185                 190

Ala Gly Ala Val Ser Xaa Trp Cys Xaa Ser Phe Ser Trp Gly Ala Ser
        195                 200                 205

Met Val Leu Leu Ile Pro Gly Gly Lys Glu Glu Pro Gly Ala Cys Pro
    210                 215                 220

Ala Xaa Arg Leu Glu Leu Arg Arg Xaa Gln Gly
225                 230                 235

(2) INFORMATION FOR SEQ ID NO:11:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: unknown (ii) MOLECULE TYPE: peptide (ix) FEATURE:
        (A) NAME/KEY: Peptide
        (B) LOCATION: 1..170
        (D) OTHER INFORMATION: /note= "z are substitued amino acid
            residues"

(xi) SEQUENCE DESCRIPTION: SEQ ID NO:11:

Ala Asp Arg Glu Arg Ser Ile Glx Asp Phe Cys Leu Val Ser Lys Val
1               5                   10                  15

Glx Gly Glx Cys Glx Glx Glx Glx Glx Trp Trp Tyr Asn Val Thr
            20                  25                  30

Asp Gly Ser Cys Gln Leu Phe Glx Tyr Glx Gly Cys Glx Glx Glx Ser
            35                  40                  45

Asn Asn Tyr Glx Thr Lys Glu Glu Cys Leu Lys Lys Cys Ala Thr Glx
50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glx Glu Tyr Cys Thr Ala Asn Ala Val Glx
            100                 105                 110

Gly Glx Cys Glx Glx Glx Glx Glx Glx Trp Tyr Phe Asp Val Glu Arg
        115                 120                 125

Asn Ser Cys Asn Asn Phe Glx Tyr Glx Gly Cys Glx Glx Glx Lys Asn
        130                 135                 140

Ser Tyr Glx Ser Glu Glu Ala Cys Met Leu Arg Cys Phe Arg Glx Gln
145                 150                 155                 160

Glu Asn Pro Pro Leu Pro Leu Gly Ser Lys
                165                 170

(2) INFORMATION FOR SEQ ID NO:12:

(i) SEQUENCE CHARACTERISTICS:
        (A) LENGTH: 393 base pairs
        (B) TYPE: nucleic acid
        (C) STRANDEDNESS: single
        (D) TOPOLOGY: Not Relevant (ii) MOLECULE TYPE: DNA (genomic)

(ix) FEATURE:
        (A) NAME/KEY: misc_feature
        (B) LOCATION: 390..391
        (D) OTHER INFORMATION: /note= "residue 390 is any nucleic
```

```
            (ix) FEATURE:
                  (A) NAME/KEY: misc_feature
                  (B) LOCATION: 384..385
                  (D) OTHER INFORMATION: /note= "residue 384 is any nucleic
                        acid"

(ix) FEATURE:
                  (A) NAME/KEY: misc_feature
                  (B) LOCATION: 367..368
                  (D) OTHER INFORMATION: /note= "residue 367 is any nucleic
                        acid"

(ix) FEATURE:
                  (A) NAME/KEY: misc_feature
                  (B) LOCATION: 361..362
                  (D) OTHER INFORMATION: /note= "residue 361 is any nucleic
                        acid"

(xi) SEQUENCE DESCRIPTION: SEQ ID NO:12:

GGCCGGGTCG TTTCTCGCCT GGCTGGGATC GCTGCTCCTC TCTGGGGTCC TGGCCGGCCG       60

ACCGAGAACG CAGCATCCAC GACTTCTGCC TGGTGTCGAA GGTGGTGGGC AGATTCCGGG      120

CCTCCATGCC TAGGTGGTGG TACAATGTCA CTGACGGATC CTGCCAGCTG TTTGTGTATG      180

GGGGCTGTGA CGGAAACAGC AATAATTACC TGACCAAGGA GGAGTGCCTC AAGAAATGTG      240

CCACTGTCAC AGAGAATGCC ACGGGTGACC TGGCCACCAG CAGGAATGCA GCGGATTCCT      300

CTGTCCCAAG TGCTCCCAGA AGGCAGGATT CTTGAAGACC ACTTCAGCGA TATGTTTCAA      360

ATATTGAAAG AATAATTGCA CCGACAACGA ATT                                   393

(2) INFORMATION FOR SEQ ID NO:13:

(i) SEQUENCE CHARACTERISTICS:
            (A) LENGTH: 130 amino acids
            (B) TYPE: amino acid
            (C) STRANDEDNESS: Not Relevant
            (D) TOPOLOGY: unknown (ii) MOLECULE TYPE: peptide (ix) FEATURE:
            (A) NAME/KEY: Region
            (B) LOCATION: 1..18
            (D) OTHER INFORMATION: /label= signalpeptide (ix) FEATURE:
            (A) NAME/KEY: Peptide
            (B) LOCATION: 111..130
            (D) OTHER INFORMATION: /note= "X=no amino acid as from
                  nonsense codon"

(xi) SEQUENCE DESCRIPTION: SEQ ID NO:13:

Pro Gly Arg Phe Ser Pro Gly Trp Asp Arg Cys Ser Ser Leu Gly Ser
1               5                   10                  15

Trp Pro Ala Asp Arg Glu Arg Ser Ile His Asp Phe Cys Leu Val Ser
            20                  25                  30

Lys Val Val Gly Arg Glu Arg Ala Ser Met Pro Arg Trp Trp Tyr Asn
        35                  40                  45

Val Thr Asp Gly Ser Cys Gln Leu Phe Val Tyr Gly Gly Cys Asp Gly
    50                  55                  60

Asn Ser Asn Asn Tyr Leu Thr Lys Glu Glu Cys Leu Lys Lys Cys Ala
65                  70                  75                  80

Thr Val Thr Glu Asn Ala Thr Gly Asp Leu Ala Thr Ser Arg Asn Ala
                85                  90                  95

Ala Asp Ser Ser Val Pro Ser Ala Pro Arg Arg Gln Asp Ser Xaa Arg
```

-continued

```
             100                 105                 110
Pro Leu Gln Arg Tyr Val Ser Xaa Ile Xaa Arg Ile Ile Ala Pro Xaa
            115                 120                 125
Thr Xaa
    130
```

(2) INFORMATION FOR SEQ ID NO:14:

(i) SEQUENCE CHARACTERISTICS:
        (A) LENGTH: 511 base pairs
        (B) TYPE: nucleic acid
        (C) STRANDEDNESS: single
        (D) TOPOLOGY: Not Relevant (ii) MOLECULE TYPE: DNA (genomic)

(ix) FEATURE:
        (A) NAME/KEY: misc_feature
        (B) LOCATION: 509..510
        (D) OTHER INFORMATION: /note= "residue 509 is any nucleic
            acid"

(ix) FEATURE:
        (A) NAME/KEY: misc_feature
        (B) LOCATION: 481..482
        (D) OTHER INFORMATION: /note= "residue 481 is any nucleic
            acid"

(ix) FEATURE:
        (A) NAME/KEY: misc_feature
        (B) LOCATION: 424..425
        (D) OTHER INFORMATION: /note= "residue 424 is any nucleic
            acid"

(xi) SEQUENCE DESCRIPTION: SEQ ID NO:14:

```
GCAATAATTA CCTGACCAAG GAGGAGTGCC TCAAGAAATG TGCCACTGTC ACAGAGAATG    60

CCACGGGTGA CCTGGCCACC AGCAGGAATG CAGCGGATTC CTCTGTCCCA AGTGCTCCCA   120

GAAGGCAGGA TTCTGAAGAC CACTCCAGCG ATATGTTCAA CTATGAAGAA TACTGCACCG   180

CCAACGCAGT CACTGGGCCT TGCCGTGCAT CCTTCCCACG CTGGTACTTT GACGTGGAGA   240

GGAACTCCTG CAATAACTTC ATCTATGGAG CTGCCGGGG CAATAAGAAC AGCTACCGCT    300

CTGAGGAGGC CTGCATGCTC CGCTGCTTCC GCCAGCAGGA GAATCCTCCC CTGCCCCTTG   360

GCTCAAAGGT GGTGGTTCTG GCCGGGGCTG TTTCGTGATG GTGTTGATCC TTTTCCTGGG   420

GAGCATCCAT GGTCTTACTG ATTCCGGGTG GCAAGGAGGA ACCAGGAGCG TGCCCTGCGG   480

AACGTCTGGA GCTTCGGAGA TGACAAGGGA T                                 511
```

(2) INFORMATION FOR SEQ ID NO:15:

(i) SEQUENCE CHARACTERISTICS:
        (A) LENGTH: 169 amino acids
        (B) TYPE: amino acid
        (C) STRANDEDNESS: Not Relevant
        (D) TOPOLOGY: unknown (ii) MOLECULE TYPE: peptide (ix) FEATURE:
        (A) NAME/KEY: Peptide
        (B) LOCATION: 1..169
        (D) OTHER INFORMATION: /note= "X=no amino acid as from
            nonsense codon or stop codon"

(xi) SEQUENCE DESCRIPTION: SEQ ID NO:15:

```
Gln Xaa Leu Pro Asp Gln Gly Gly Val Pro Gln Glu Met Cys His Cys
1               5                  10                  15
```

-continued

```
His Arg Glu Cys His Gly Xaa Pro Gly His Gln Gln Glu Cys Ser Gly
         20                  25                  30

Phe Leu Cys Pro Lys Ser Pro Arg Arg Gln Asp Ser Glu Asp His Ser
     35                  40                  45

Ser Asp Met Phe Asn Tyr Glu Glu Tyr Cys Thr Ala Asn Ala Val Thr
 50                  55                  60

Gly Pro Cys Arg Ala Ser Phe Pro Arg Trp Tyr Phe Asp Val Glu Arg
 65                  70                  75                  80

Asn Ser Cys Asn Asn Phe Ile Tyr Gly Gly Cys Arg Gly Asn Lys Asn
                 85                  90                  95

Ser Tyr Arg Ser Glu Glu Ala Cys Met Leu Arg Cys Phe Arg Gln Gln
             100                 105                 110

Glu Asn Pro Pro Leu Pro Leu Gly Ser Lys Val Val Val Leu Ala Gly
         115                 120                 125

Ala Val Ser Xaa Trp Cys Xaa Ser Phe Ser Trp Gly Ala Ser Met Val
     130                 135                 140

Leu Leu Ile Pro Gly Gly Lys Glu Glu Pro Gly Ala Cys Pro Ala Xaa
145                 150                 155                 160

Arg Leu Glu Leu Arg Arg Xaa Gln Gly
                 165
```

(2) INFORMATION FOR SEQ ID NO:16:

(i) SEQUENCE CHARACTERISTICS:
        (A) LENGTH: 428 base pairs
        (B) TYPE: nucleic acid
        (C) STRANDEDNESS: single
        (D) TOPOLOGY: Not Relevant (ii) MOLECULE TYPE: DNA (genomic)

(ix) FEATURE:
        (A) NAME/KEY: misc_feature
        (B) LOCATION: 426..430
        (D) OTHER INFORMATION: /note= "residue 426 is any nucleic
            acid"

(ix) FEATURE:
        (A) NAME/KEY: misc_feature
        (B) LOCATION: 1..50
        (D) OTHER INFORMATION: /note= "residues 3, 11, 12, 17, an
            48 are any nucleic acid"

(xi) SEQUENCE DESCRIPTION: SEQ ID NO:16:

```
GCAGCGCGTT AATCGCATGC TGGGATCGCT GCTCCTCTCT GGGGTCGAGG CGGCCGACCG      60

AGAACGCAGC ATCCACGACT TCTGCCTGGT GTCGAAGGTG GTGGGCAGAT GCCGGGCCTC     120

CATGCCTAGG TGGTGGTACA ATGTCACTGA CGGATCCTGC CAGCTGTTTG TGTATGGGGG     180

CTGTGACGGA AACAGCAATA ATTACCTGAC CAAGGAGGAG TGCCTCAAGA AATGTGCCAC     240

TGTCACAGAG AATGCCACGG GTGACCTGGC CACCAGCAGG AATGCAGCGG ATTCCTCTGT     300

CCCAAGTGCT CCCAGAAGGC AGGATTCTTG AAGACCACTT CAGCGATATG TTCAACTATG     360

AAGAATACTG GCACCGCCAA CGCATTCACT GGGCCTGCGT GCATCCTTCC CACGCTGGTA     420

CTTTGACG                                                             428
```

(2) INFORMATION FOR SEQ ID NO:17:

(i) SEQUENCE CHARACTERISTICS:
        (A) LENGTH: 424 base pairs
        (B) TYPE: nucleic acid
        (C) STRANDEDNESS: single
        (D) TOPOLOGY: Not Relevant (ii) MOLECULE TYPE: DNA (genomic)

(ix) FEATURE:
             (A) NAME/KEY: misc_feature
             (B) LOCATION: 429..430
             (D) OTHER INFORMATION: /note= "residue 429 is any nucleic
                 acid"

(ix) FEATURE:
             (A) NAME/KEY: misc_feature
             (B) LOCATION: 1..50
             (D) OTHER INFORMATION: /note= "residues 3, 11, 12, 17, an
                 48 are any nucleic acid"

(xi) SEQUENCE DESCRIPTION: SEQ ID NO:17:

TGGGAATCGC TGCTCCTCTC TGGGGTCCTG GCGGCCGACC GAGAACGCAG CATCCACGAC     60

TTCTGCCTGG TGTCGAAGGT GGTGGGCAGA TGCCGGGCCT CCATGCCTAG GTGGTGGTAC    120

AATGTCACTG ACGGATCCTG CCAGCTGTTT GTGTATGGGG GCTGTGACGG AAACAGCAAT    180

AATTACCTGA CCAAGGAGGA GTGCCTCAAG AAATGTGCCA CTGTCACAGA GAATGCCACG    240

GGTGACCTGG CCACCAGCAG GAATGCAGCG GATTCCTCTG TCCCAAGTGC TCCCAGAAGG    300

CAGGATTCTT GAAGACCACT TCAGCGATAT GTTCAACTAT GAAGAATACT GCACCGCCAA    360

CGCAGTCACT GGGCCTTGCG TGGAATCCTT TCCCACGCTG GAAATTTAGA CGTTGAGAAG    420

GAAC                                                                 424

(2) INFORMATION FOR SEQ ID NO:18:

(i) SEQUENCE CHARACTERISTICS:
            (A) LENGTH: 57 amino acids
            (B) TYPE: amino acid
            (C) STRANDEDNESS: Not Relevant
            (D) TOPOLOGY: unknown (ii) MOLECULE TYPE: peptide (xi) SEQUENCE DESCRIPTION: SEQ ID NO:18:

His Ser Phe Cys Ala Phe Lys Ala Asp Asp Gly Pro Cys Lys Ala Ile
1               5                   10                  15

Met Lys Arg Phe Phe Phe Asn Ile Phe Thr Arg Gln Cys Glu Glu Phe
            20                  25                  30

Ile Tyr Gly Gly Cys Glu Gly Asn Gln Asn Arg Phe Glu Ser Leu Glu
        35                  40                  45

Glu Cys Lys Lys Met Cys Thr Arg Asp
    50                  55

(2) INFORMATION FOR SEQ ID NO:19:

(i) SEQUENCE CHARACTERISTICS:
            (A) LENGTH: 57 amino acids
            (B) TYPE: amino acid
            (C) STRANDEDNESS: Not Relevant
            (D) TOPOLOGY: unknown (ii) MOLECULE TYPE: peptide (xi) SEQUENCE DESCRIPTION: SEQ ID NO:19:

Pro Asp Phe Cys Phe Leu Glu Glu Asp Pro Gly Ile Cys Arg Gly Tyr
1               5                   10                  15

Ile Thr Arg Tyr Phe Tyr Asn Asn Gln Thr Lys Gln Cys Glu Arg Phe
            20                  25                  30

Lys Tyr Gly Gly Cys Leu Gly Asn Met Asn Asn Phe Glu Thr Leu Glu
        35                  40                  45

```
Glu Cys Lys Asn Ile Cys Glu Asp Gly
    50                  55
```

(2) INFORMATION FOR SEQ ID NO:20:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:20:

```
Pro Ser Trp Cys Leu Thr Pro Ala Asp Arg Gly Leu Cys Arg Ala Asn
1               5                   10                  15

Glu Asn Arg Phe Tyr Tyr Asn Ser Val Ile Gly Lys Cys Arg Pro Phe
                20                  25                  30

Lys Tyr Ser Gly Cys Gly Gly Asn Glu Asn Asn Phe Thr Ser Lys Gln
                35                  40                  45

Glu Cys Leu Arg Ala Cys Lys Lys Gly
    50                  55
```

(2) INFORMATION FOR SEQ ID NO:21:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:21:

```
Ala Glu Ile Cys Leu Leu Pro Leu Asp Tyr Gly Pro Cys Arg Ala Leu
1               5                   10                  15

Leu Leu Arg Tyr Tyr Tyr Arg Tyr Arg Thr Gln Ser Cys Arg Gln Phe
                20                  25                  30

Leu Tyr Gly Gly Cys Glu Gly Asn Ala Asn Asn Phe Tyr Thr Trp Glu
                35                  40                  45

Ala Cys Asp Asp Ala Cys Trp Arg Ile
    50                  55
```

(2) INFORMATION FOR SEQ ID NO:22:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:22:

```
Pro Ser Phe Cys Tyr Ser Pro Lys Asp Glu Gly Leu Cys Ser Ala Asn
1               5                   10                  15

Val Thr Arg Tyr Tyr Phe Asn Pro Arg Tyr Arg Thr Cys Asp Ala Phe
                20                  25                  30

Thr Tyr Thr Gly Cys Gly Asn Asn Asp Asn Asn Phe Val Ser Arg Glu
                35                  40                  45

Asp Ser Lys Arg Ala Cys Ala Lys Ala
    50                  55
```

(2) INFORMATION FOR SEQ ID NO:23:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:23:

```
Lys Ala Val Cys Ser Gln Glu Ala Met Thr Gly Pro Cys Arg Ala Val
1               5                   10                  15

Met Pro Arg Thr Thr Phe Asp Leu Ser Lys Gly Lys Cys Val Arg Phe
            20                  25                  30

Ile Thr Gly Gly Cys Gly Gly Asn Arg Asn Asn Phe Glu Ser Glu Asp
            35                  40                  45

Tyr Cys Met Ala Val Cys Lys Ala Met
50                  55
```

(2) INFORMATION FOR SEQ ID NO:24:

(i) SEQUENCE CHARACTERISTICS:
        (A) LENGTH: 58 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:24:

```
Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
50                  55
```

(2) INFORMATION FOR SEQ ID NO:25:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:25:

```
Cys Gln Leu Gly Tyr Ser Ala Gly Pro Cys Met Gly Met Thr Ser Arg
1               5                   10                  15

Tyr Phe Tyr Asn Gly Thr Ser Met Ala Cys Glu Thr Phe Gln Tyr Gly
            20                  25                  30

Gly Cys Met Gly Asn Gly Asn Asn Phe Val Thr Glu Lys Glu Cys Leu
            35                  40                  45

Gln Thr Cys
50
```

(2) INFORMATION FOR SEQ ID NO:26:

(i) SEQUENCE CHARACTERISTICS:

(A) LENGTH: 57 amino acids
(B) TYPE: amino acid
(C) STRANDEDNESS: Not Relevant
(D) TOPOLOGY: unknown (ii) MOLECULE TYPE: peptide (xi) SEQUENCE DESCRIPTION: SEQ ID NO:26:

Val Ala Ala Cys Asn Leu Pro Ile Val Arg Gly Pro Cys Arg Ala Phe
1               5                   10                  15

Ile Gln Leu Trp Ala Phe Asp Ala Val Lys Gly Lys Cys Val Leu Phe
                20                  25                  30

Pro Tyr Gly Gly Cys Gln Gly Asn Gly Asn Lys Phe Tyr Ser Glu Lys
            35                  40                  45

Glu Cys Arg Glu Tyr Cys Gly Val Pro
50                  55

(2) INFORMATION FOR SEQ ID NO:27:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:27:

Glu Val Cys Cys Ser Glu Gln Ala Glu Thr Gly Pro Cys Arg Ala Met
1               5                   10                  15

Ile Ser Arg Trp Tyr Phe Asp Val Thr Glu Gly Lys Cys Ala Pro Phe
                20                  25                  30

Phe Tyr Gly Gly Cys Gly Gly Asn Arg Asn Asn Phe Asp Thr Glu Glu
            35                  40                  45

Tyr Cys Met Ala Val Cys Gly Ser Ala
50                  55

(2) INFORMATION FOR SEQ ID NO:28:

(i) SEQUENCE CHARACTERISTICS:
        (A) LENGTH: 51 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:28:

Cys Lys Leu Pro Lys Asp Glu Gly Thr Cys Arg Asp Phe Ile Leu Lys
1               5                   10                  15

Trp Tyr Tyr Asp Pro Asn Thr Lys Ser Cys Ala Arg Phe Trp Tyr Gly
                20                  25                  30

Gly Cys Gly Gly Asn Glu Asn Lys Phe Gly Ser Gln Lys Glu Cys Glu
            35                  40                  45

Lys Val Cys
    50

(2) INFORMATION FOR SEQ ID NO:29:

(i) SEQUENCE CHARACTERISTICS:
        (A) LENGTH: 57 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:29:

Pro Asn Val Cys Ala Phe Pro Met Glu Lys Gly Pro Cys Gln Thr Tyr
1               5                   10                  15

Met Thr Arg Trp Phe Phe Asn Phe Glu Thr Gly Glu Cys Glu Leu Phe
            20                  25                  30

Ala Tyr Gly Gly Cys Gly Gly Asn Ser Asn Asn Phe Leu Arg Lys Glu
        35                  40                  45

Lys Cys Glu Lys Phe Cys Lys Phe Thr
    50                  55

(2) INFORMATION FOR SEQ ID NO:30:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:30:

GCCAAGCTTG GATAAAAGAT ATGAAGAATA CTGCACCGCC AACGCA                46

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:31:

GGGGATCCTC ACTGCTGGCG GAAGCAGCGG AGCAT                             35

(2) INFORMATION FOR SEQ ID NO:32:

(i) SEQUENCE CHARACTERISTICS:
        (A) LENGTH: 206 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:32:

CCAAGCTTGG ATAAAAGATA TGAAGAATAC TGCACCGCCA ACGCAGTCAC TGGGCCTTGC    60

CGTGCATCCT TCCCACGCTG GTACTTTGAC GTGGAGAGGA ACTCCTGCAA TAACTTCATC   120

TATGGAGGCT GCCGGGGCAA TAAGAACAGC TACCGCTCTG AGGAGGCCTG CATGCTCCGC   180

TGCTTCCGCC AGCAGTGAGG ATCCCC                                        206

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:33:

CGAAGCTTCA TCTCCGAAGC TCCAGACG                                    28

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:34:

AGGATCTAGA CAATAATTAC CTGACCAAGG A                                31

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:35:

GGTCTAGAGG CCGGGTCCGT TTCTCGCCTG GCTGGGA                          37

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:36:

CACCTGATCG CGAGACCCC                                              19

(2) INFORMATION FOR SEQ ID NO:37:

(i) SEQUENCE CHARACTERISTICS:
        (A) LENGTH: 19 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:37:

GATTTAGGTG ACACTATAG                                              19

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:38:

TAATACGACT CACTATAGGG                                             20

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:39:

```
TTACCTGACC AAGGAGGAGT GC                                       22
```

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:40:

```
AATCCGCTGC ATTCCTGCTG GTG                                      23
```

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: unknown (ii) MOLECULE TYPE: cDNA (xi) SEQUENCE DESCRIPTION: SEQ ID NO:41:

```
CAGTCACTGG GCCTTGCCGT                                          20
```

(2) INFORMATION FOR SEQ ID NO:42:

(i) SEQUENCE CHARACTERISTICS:
        (A) LENGTH: 105 base pairs
        (B) TYPE: nucleic acid
        (C) STRANDEDNESS: Not Relevant
        (D) TOPOLOGY: Not Relevant (ii) MOLECULE TYPE: cDNA (xi) SEQUENCE DESCRIPTION: SEQ ID NO:42:

```
GAAGGGGTAA GCTTGGATAA AAGATATGAA GAATACTGCA CCGCCAACGC AGTCACTGGG    60
CCTTGCCGTG CATCCTTCCC ACGCTGGTAC TTTGACGTGG AGAGG                   105
```

(2) INFORMATION FOR SEQ ID NO:43:

(i) SEQUENCE CHARACTERISTICS:
        (A) LENGTH: 129 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:43:

```
CGCGGATCCC TACTGGCGGA AGCAGCGGAG CATGCAGGCC TCCTCAGAGC GGTAGCTGTT    60
CTTATTGCCC CGGCAGCCTC CATAGATGAA GTTATTGCAG GAGTTCCTCT CCACGTCAAA   120
```

```
GTACCAGCG                                                                  129
```

(2) INFORMATION FOR SEQ ID NO:44:

(i) SEQUENCE CHARACTERISTICS:
        (A) LENGTH: 207 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:44:

```
GAAGGGGTAA GCTTGGATAA AAGATATGAA GAATACTGCA CCGCCAACGC AGTCACTGGG    60

CCTTGCCGTG CATCCTTCCC ACGCTGGTAC TTTGACGTGG AGAGGAACTC CTGCAATAAC   120

TTCATCTATG GAGGCTGCCG GGGCAATAAG AACAGCTACC GCTCTGAGGA GGCCTGCATG   180

CTCCGCTGCT TCCGCCAGTA GGGATCC                                        207
```

(2) INFORMATION FOR SEQ ID NO:45:

(i) SEQUENCE CHARACTERISTICS:
        (A) LENGTH: 248 amino acids
        (B) TYPE: amino acid
        (C) STRANDEDNESS: Not Relevant
        (D) TOPOLOGY: unknown (ii) MOLECULE TYPE: peptide (ix) FEATURE:
        (A) NAME/KEY: Region
        (B) LOCATION: 1..18
        (D) OTHER INFORMATION: /label= signalpeptide (xi) SEQUENCE DESCRIPTION: SEQ ID NO:45:

```
Met Leu Arg Ala Glu Ala Asp Gly Val Ser Arg Leu Leu Gly Ser Leu
1               5                   10                  15

Leu Leu Ser Gly Val Leu Ala Ala Asp Arg Glu Arg Ser Ile His Asp
                20                  25                  30

Phe Cys Leu Val Ser Lys Val Val Gly Arg Cys Arg Ala Ser Met Pro
            35                  40                  45

Arg Trp Trp Tyr Asn Val Thr Asp Gly Ser Cys Gln Leu Phe Val Tyr
        50                  55                  60

Gly Gly Cys Asp Gly Asn Ser Asn Asn Tyr Leu Thr Lys Glu Glu Cys
65                  70                  75                  80

Leu Lys Lys Cys Ala Thr Val Thr Glu Asn Ala Thr Gly Asp Leu Ala
                85                  90                  95

Thr Ser Arg Asn Ala Ala Asp Ser Ser Val Pro Ser Ala Pro Arg Arg
            100                 105                 110

Gln Asp Ser Glu Asp His Ser Ser Asp Met Phe Asn Tyr Glu Glu Tyr
        115                 120                 125

Cys Thr Ala Asn Ala Val Thr Gly Pro Cys Arg Ala Ser Phe Pro Arg
130                 135                 140

Trp Tyr Phe Asp Val Glu Arg Asn Ser Cys Asn Asn Phe Ile Tyr Gly
145                 150                 155                 160

Gly Cys Arg Gly Asn Lys Asn Ser Tyr Arg Ser Glu Glu Ala Cys Met
                165                 170                 175

Leu Arg Cys Phe Arg Gln Gln Glu Asn Pro Pro Leu Pro Leu Gly Ser
            180                 185                 190

Lys Val Val Val Leu Ala Gly Leu Phe Val Met Val Leu Ile Leu Phe
        195                 200                 205
```

```
Leu Gly Ala Ser Met Val Tyr Leu Ile Arg Val Ala Arg Arg Asn Gln
    210                 215                 220

Glu Arg Ala Leu Arg Thr Val Trp Ser Ser Gly Asp Asp Lys Glu Gln
225                 230                 235                 240

Leu Val Lys Asn Thr Tyr Val Leu
                245
```

(2) INFORMATION FOR SEQ ID NO:46:

(i) SEQUENCE CHARACTERISTICS:
        (A) LENGTH: 213 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:46:

```
Ala Asp Arg Glu Arg Ser Ile His Asp Phe Cys Leu Val Ser Lys Val
1                   5                   10                  15

Val Gly Arg Cys Arg Ala Ser Met Pro Arg Trp Trp Tyr Asn Val Thr
                20                  25                  30

Asp Gly Ser Cys Gln Leu Phe Val Tyr Gly Gly Cys Asp Gly Asn Ser
            35                  40                  45

Asn Asn Tyr Leu Thr Lys Glu Glu Cys Leu Lys Lys Cys Ala Thr Val
50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
            115                 120                 125

Asn Ser Cys Asn Asn Phe Ile Tyr Gly Gly Cys Arg Gly Asn Lys Asn
                130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Leu Ala Gly
                165                 170                 175

Leu Phe Val Met Val Leu Ile Leu Phe Leu Gly Ala Ser Met Val Tyr
                180                 185                 190

Leu Ile Arg Val Ala Arg Arg Asn Gln Glu Arg Ala Leu Arg Thr Val
            195                 200                 205

Trp Ser Phe Gly Asp
    210
```

(2) INFORMATION FOR SEQ ID NO:47:

(i) SEQUENCE CHARACTERISTICS:
        (A) LENGTH: 240 amino acids
        (B) TYPE: amino acid
        (C) STRANDEDNESS: Not Relevant
        (D) TOPOLOGY: unknown (ii) MOLECULE TYPE: peptide (ix) FEATURE:
        (A) NAME/KEY: Region
        (B) LOCATION: 1..18

(D) OTHER INFORMATION: /label= signalpeptide (xi) SEQUENCE DESCRIPTION: SEQ ID NO:47:

```
Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala Ala Asp Arg Glu Arg
            20                  25                  30

Ser Ile His Asp Phe Cys Leu Val Ser Lys Val Val Gly Arg Cys Arg
        35                  40                  45

Ala Ser Met Pro Arg Trp Trp Tyr Asn Val Thr Asp Gly Ser Cys Gln
50                      55                  60

Leu Phe Val Tyr Gly Gly Cys Asp Gly Asn Ser Asn Asn Tyr Leu Thr
65                  70                  75                  80

Lys Glu Glu Cys Leu Lys Lys Cys Ala Thr Val Thr Glu Asn Ala Thr
                85                  90                  95

Gly Asp Leu Ala Thr Ser Arg Asn Ala Ala Asp Ser Ser Val Pro Ser
            100                 105                 110

Ala Pro Arg Arg Gln Asp Ser Glu Asp His Ser Ser Asp Met Phe Asn
        115                 120                 125

Tyr Glu Glu Tyr Cys Thr Ala Asn Ala Val Thr Gly Pro Cys Arg Ala
130                     135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Gln Glu Asn Pro Pro Leu
            180                 185                 190

Pro Leu Gly Ser Lys Val Val Val Leu Ala Gly Leu Phe Val Met Val
        195                 200                 205

Leu Ile Leu Phe Leu Gly Ala Ser Met Val Tyr Leu Ile Arg Val Ala
        210                 215                 220

Arg Arg Asn Gln Glu Arg Ala Leu Arg Thr Val Trp Ser Phe Gly Asp
225                 230                 235                 240
```

(2) INFORMATION FOR SEQ ID NO:48:

(i) SEQUENCE CHARACTERISTICS:
        (A) LENGTH: 225 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:48:

```
Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
        35                  40                  45

Asn Asn Tyr Leu Thr Lys Glu Glu Cys Leu Lys Lys Cys Ala Thr Val
50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95
```

```
Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
            115                 120                 125

Asn Ser Cys Asn Asn Phe Ile Tyr Gly Gly Cys Arg Gly Asn Lys Asn
            130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Leu Ala Gly
                165                 170                 175

Leu Phe Val Met Val Leu Ile Leu Phe Leu Gly Ala Ser Met Val Tyr
            180                 185                 190

Leu Ile Arg Val Ala Arg Arg Asn Gln Glu Arg Ala Leu Arg Thr Val
            195                 200                 205

Trp Ser Ser Gly Asp Asp Lys Glu Gln Leu Val Lys Asn Thr Tyr Val
    210                 215                 220

Leu
225

(2) INFORMATION FOR SEQ ID NO:49:

(i) SEQUENCE CHARACTERISTICS:
        (A) LENGTH: 252 amino acids
        (B) TYPE: amino acid
        (C) STRANDEDNESS: Not Relevant
        (D) TOPOLOGY: unknown (ii) MOLECULE TYPE: peptide (ix) FEATURE:
        (A) NAME/KEY: Region
        (B) LOCATION: 1..18
        (D) OTHER INFORMATION: /label= signalpeptide (xi) SEQUENCE DESCRIPTION: SEQ ID NO:49:

Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala Ala Asp Arg Glu Arg
            20                  25                  30

Ser Ile His Asp Phe Cys Leu Val Ser Lys Val Val Gly Arg Cys Arg
            35                  40                  45

Ala Ser Met Pro Arg Trp Trp Tyr Asn Val Thr Asp Gly Ser Cys Gln
    50                  55                  60

Leu Phe Val Tyr Gly Gly Cys Asp Gly Asn Ser Asn Asn Tyr Leu Thr
65                  70                  75                  80

Lys Glu Glu Cys Leu Lys Lys Cys Ala Thr Val Thr Glu Asn Ala Thr
            85                  90                  95

Gly Asp Leu Ala Thr Ser Arg Asn Ala Ala Asp Ser Ser Val Pro Ser
            100                 105                 110

Ala Pro Arg Arg Gln Asp Ser Glu Asp His Ser Ser Asp Met Phe Asn
            115                 120                 125

Tyr Glu Glu Tyr Cys Thr Ala Asn Ala Val Thr Gly Pro Cys Arg Ala
            130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
            165                 170                 175
```

```
Glu Ala Cys Met Leu Arg Cys Phe Arg Gln Gln Glu Asn Pro Pro Leu
            180                 185                 190

Pro Leu Gly Ser Lys Val Val Leu Ala Gly Leu Phe Val Met Val
            195                 200                 205

Leu Ile Leu Phe Leu Gly Ala Ser Met Val Tyr Leu Ile Arg Val Ala
        210                 215                 220

Arg Arg Asn Gln Glu Arg Ala Leu Arg Thr Val Trp Ser Ser Gly Asp
225                 230                 235                 240

Asp Lys Glu Gln Leu Val Lys Asn Thr Tyr Val Leu
                245                 250
```

(2) INFORMATION FOR SEQ ID NO:50:

(i) SEQUENCE CHARACTERISTICS:
        (A) LENGTH: 146 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:50:

```
Cys Leu Val Ser Lys Val Val Gly Arg Cys Arg Ala Ser Met Pro Arg
1               5                   10                  15

Trp Trp Tyr Asn Val Thr Asp Gly Ser Cys Gln Leu Phe Val Tyr Gly
            20                  25                  30

Gly Cys Asp Gly Asn Ser Asn Asn Tyr Leu Thr Lys Glu Glu Cys Leu
        35                  40                  45

Lys Lys Cys Ala Thr Val Thr Glu Asn Ala Thr Gly Asp Leu Ala Thr
50                  55                  60

Ser Arg Asn Ala Ala Asp Ser Ser Val Pro Ser Ala Pro Arg Arg Gln
65                  70                  75                  80

Asp Ser Glu Asp His Ser Ser Asp Met Phe Asn Tyr Glu Glu Tyr Cys
                85                  90                  95

Thr Ala Asn Ala Val Thr Gly Pro Cys Arg Ala Ser Phe Pro Arg Trp
                100                 105                 110

Tyr Phe Asp Val Glu Arg Asn Ser Cys Asn Asn Phe Ile Tyr Gly Gly
            115                 120                 125

Cys Arg Gly Asn Lys Asn Ser Tyr Arg Ser Glu Glu Ala Cys Met Leu
130                 135                 140

Arg Cys
145
```

(2) INFORMATION FOR SEQ ID NO:51:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:51:

```
Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
        35                  40                  45
```

```
Asn Asn Tyr Leu Thr Lys Glu Glu Cys Leu Lys Lys Cys Ala Thr Val
    50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
               100                 105                 110

Gly Pro Cys Arg Ala Ser Phe Pro Arg Trp Tyr Phe Asp Val Glu Arg
           115                 120                 125

Asn Ser Cys Asn Asn Phe Ile Tyr Gly Gly Cys Arg Gly Asn Lys Asn
        130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys
                165                 170
```

(2) INFORMATION FOR SEQ ID NO:52:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:52:

```
Ala Asp Arg Glu Arg Ser Ile His Asp Phe Cys Leu Val Ser Lys Val
1               5                  10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
        35                  40                  45

Asn Asn Tyr Leu Thr Lys Glu Glu Cys Leu Lys Lys Cys Ala Thr Val
    50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
               100                 105                 110

Gly Pro Cys Arg Ala Ser Phe Pro Arg Trp Tyr Phe Asp Val Glu Arg
           115                 120                 125

Asn Ser Cys Asn Asn Phe Ile Tyr Gly Gly Cys Arg Gly Asn Lys Asn
        130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys
                165                 170
```

(2) INFORMATION FOR SEQ ID NO:53:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:53:

Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala
            20                  25

(2) INFORMATION FOR SEQ ID NO:54:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:54:

Met Leu Arg Ala Glu Ala Asp Gly Asx Ser Arg Leu Leu Gly Ser Leu
1               5                   10                  15

Leu Leu Ser Gly Val Leu Ala
            20

(2) INFORMATION FOR SEQ ID NO:55:

(i) SEQUENCE CHARACTERISTICS:
        (A) LENGTH: 102 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:55:

GAAGGGGTAA GCTTGGATAA AAGAGAAGAA TACTGTACTG CTAATGCTGT TACTGGTCCA         60

TGTAGAGCTT CTTTTCCAAG ATGGTACTTT GATGTTGAAA GA                           102

(2) INFORMATION FOR SEQ ID NO:56:

(i) SEQUENCE CHARACTERISTICS:
        (A) LENGTH: 129 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:56:

ACTGGATCCT CATTGGCGAA AACATCTCAA CATACAGGCT TCTTCAGATC TGTAAGAATT         60

TTTATTACCT CTACAACCAC CGTAAATAAA ATTATTACAA GAATTTCTTT CAACATCAAA        120

GTACCATCT                                                                129

(2) INFORMATION FOR SEQ ID NO:57:

(i) SEQUENCE CHARACTERISTICS:
        (A) LENGTH: 108 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:57:

```
GAAGGGGTAA GCTTGGATAA AAGAAATTAC GAAGAATACT GTACTGCTAA TGCTGTTACT        60

GGTCCATGTA GAGCTTCTTT TCCAAGATGG TACTTTGATG TTGAAAGA                    108
```

(2) INFORMATION FOR SEQ ID NO:58:

(i) SEQUENCE CHARACTERISTICS:
        (A) LENGTH: 117 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:58:

```
GAAGGGGTAA GCTTGGATAA AAGAGATATG TTTAATTACG AAGAATACTG TACTGCTAAT        60

GCTGTTACTG GTCCATGTAG AGCTTCTTTT CCAAGATGGT ACTTTGATGT TGAAAGA          117
```

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:59:

```
CACCTGATCG CGAAGACCCC                                                    20
```

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:60:

```
CTGGCGGAAG CAGCGGAGCA TGC                                                23
```

(2) INFORMATION FOR SEQ ID NO:61:

(i) SEQUENCE CHARACTERISTICS:
        (A) LENGTH: 45 base pairs
        (B) TYPE: nucleic acid
        (C) STRANDEDNESS: unknown
        (D) TOPOLOGY: Not Relevant (ii) MOLECULE TYPE: DNA (genomic)

(xi) SEQUENCE DESCRIPTION: SEQ ID NO:61:

```
CGCGTCTCGG CTGACCTGGC CCTGCAGATG GCGCACGTGT GCGGG                        45
```

(2) INFORMATION FOR SEQ ID NO:62:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:62:

```
CTGCCCCTTG GCTCAAAGTA GGAAGATCTT CCCCCCGGGG GGGTGGTTCT GGCGGGGCTG        60
```

(2) INFORMATION FOR SEQ ID NO:63:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:63:

```
Leu Arg Cys Phe Arg Gln Gln Glu Asn Pro Pro Pro Leu Gly
1               5                   10
```

(2) INFORMATION FOR SEQ ID NO:64:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:64:

```
Ala Asp Arg Glu Arg Ser Ile His Asp Phe Cys Leu Val Ser Lys Val
1               5                   10                  15

Val Gly Arg Cys
            20
```

(2) INFORMATION FOR SEQ ID NO:65:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:65:

```
Phe Asn Tyr Glu Glu Tyr Cys Thr Ala Asn Ala Val Thr Gly Pro Cys
1               5                   10                  15

Arg Ala Ser Phe
            20
```

(2) INFORMATION FOR SEQ ID NO:66:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:66:

```
Pro Arg Tyr Val Asp Gly Ser Gln Phe Tyr Gly
1               5                   10
```

(2) INFORMATION FOR SEQ ID NO:67:

(i) SEQUENCE CHARACTERISTICS:
        (A) LENGTH: 55 amino acids
        (B) TYPE: amino acid
        (C) STRANDEDNESS: Not Relevant (D) TOPOLOGY: unknown (ii) MOLECULE TYPE: peptide (xi) SEQUENCE DESCRIPTION: SEQ ID NO:67:

Val Val Val Leu Ala Gly Leu Phe Val Met Val Leu Ile Leu Phe Leu
1               5                   10                  15

Gly Ala Ser Met Val Tyr Leu Ile Arg Val Ala Arg Arg Asn Gln Glu
            20                  25                  30

Arg Ala Leu Arg Thr Val Trp Ser Ser Gly Asp Asp Lys Glu Gln Leu
        35                  40                  45

Val Lys Asn Thr Tyr Val Leu
    50                  55

(2) INFORMATION FOR SEQ ID NO:68:

(i) SEQUENCE CHARACTERISTICS:
        (A) LENGTH: 43 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:68:

Val Val Val Leu Ala Gly Leu Phe Val Met Val Leu Ile Leu Phe Leu
1               5                   10                  15

Gly Ala Ser Met Val Tyr Leu Ile Arg Val Ala Arg Arg Asn Gln Glu
            20                  25                  30

Arg Ala Leu Arg Thr Val Trp Ser Phe Gly Asp
        35                  40

(2) INFORMATION FOR SEQ ID NO:69:

(i) SEQUENCE CHARACTERISTICS:
        (A) LENGTH: 55 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:69:

Val Val Val Leu Ala Gly Leu Phe Val Met Val Leu Ile Leu Phe Leu
1               5                   10                  15

Gly Ala Ser Met Val Tyr Leu Ile Arg Val Ala Arg Arg Asn Gln Glu
            20                  25                  30

Arg Ala Leu Arg Thr Val Trp Ser Ser Gly Asp Asp Lys Glu Gln Leu
        35                  40                  45

Val Lys Asn Thr Tyr Val Leu
    50                  55

(2) INFORMATION FOR SEQ ID NO:70:

(i) SEQUENCE CHARACTERISTICS:
        (A) LENGTH: 213 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:70:

Ala Asp Arg Glu Arg Ser Ile His Asp Phe Cys Leu Val Ser Lys Val

```
1               5                   10                  15
Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
            35                  40                  45

Asn Asn Tyr Leu Thr Lys Glu Glu Cys Leu Lys Lys Cys Ala Thr Val
        50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
            115                 120                 125

Asn Ser Cys Asn Asn Phe Ile Tyr Gly Gly Cys Arg Gly Asn Lys Asn
            130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Leu Ala Gly
                165                 170                 175

Leu Phe Val Met Val Leu Ile Leu Phe Leu Gly Ala Ser Met Val Tyr
            180                 185                 190

Leu Ile Arg Val Ala Arg Arg Asn Gln Glu Arg Ala Leu Arg Thr Val
            195                 200                 205

Trp Ser Phe Gly Asp
    210

(2) INFORMATION FOR SEQ ID NO:71:

(i) SEQUENCE CHARACTERISTICS:
        (A) LENGTH: 225 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:71:

Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
            35                  40                  45

Asn Asn Tyr Leu Thr Lys Glu Glu Cys Leu Lys Lys Cys Ala Thr Val
        50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
            115                 120                 125

Asn Ser Cys Asn Asn Phe Ile Tyr Gly Gly Cys Arg Gly Asn Lys Asn
```

```
            130              135               140
Ser Tyr Arg Ser Glu Glu Ala Cys Met Leu Arg Cys Phe Arg Gln Gln
145             150                 155              160

Glu Asn Pro Pro Leu Pro Leu Gly Ser Lys Val Val Val Leu Ala Gly
            165                 170              175

Leu Phe Val Met Val Leu Ile Leu Phe Leu Gly Ala Ser Met Val Tyr
            180                 185              190

Leu Ile Arg Val Ala Arg Arg Asn Gln Glu Arg Ala Leu Arg Thr Val
        195             200              205

Trp Ser Ser Gly Asp Asp Lys Glu Gln Leu Val Lys Asn Thr Tyr Val
        210             215              220

Leu
225
```

HUMAN BIKUNIN

This application is a continuation-in-part of International Application for Patent PCT/US97/03894 filed Mar. 10, 1997, which is a continuation-in-part from U.S. patent application Ser. No. 08/725,251 filed Oct. 4, 1996, now abandoned, which was a continuation-in-part from co-pending U.S. Provisional application patent Ser. No. 60/019,793 filed Jun. 14, 1996, which was a continuation-in-part from co-pending U.S. patent application Ser. No. 60/013,106 filed Mar. 11, 1996, the contents of all of which are incorporated by reference in their entirety.

FIELD OF THE INVENTION

The compositions of the invention relate to the field of proteins which inhibit serine protease activity. The invention also relates to the field of nucleic acid constructs, vectors and host cells for producing serine protease inhibiting proteins, pharmaceutical compositions containing the protein, and methods for their use.

BACKGROUND OF THE INVENTION

Problem Addressed

Blood loss is a serious complication of major surgeries such as open heart surgery and other complicated procedures. Cardiac surgery patients account for a significant proportion of transfused donor blood. Blood transfusion carries risks of disease transmission and adverse reactions. In addition, donor blood is expensive and demands often exceed supply. Pharmacological methods for reducing blood loss and the resultant need for transfusion have been described (reviewed by Scott et al., Ann. Thorac. Surg. 50: 843–851, 1990).

Protein Serine Protease Inhibitor

Aprotinin, a bovine serine protease inhibitor of the Kunitz family is the active substance in the medicament Trasylol®. Aprotinin (Trasylol®) has been reported as being effective in reducing perioperative blood loss (Royston et al., Lancet ii: 1289–1291, 1987; Dietrich et al., Thorac. Cardiovasc. Surg. 37: 92–98, 1989; Fraedrich et al., Thorac. Cardiovasc. Surg. 37: 89–91, 1989); W. van Oeveren et al. (1987), Ann Thorac. Surg. 44, pp 640–645; Bistrup et al., (1988) Lancet I, 366–367), but adverse effects, including hypotension and flushing (Bohrer et al., Anesthesia 45: 853–854, 1990) and allergic reactions (Dietrich et al., Supra) have been reported. Use of aprotinin in patients previously exposed to it is not recommended (Dietrich et al., Supra). Trasylol® has also been used for the treatment of hyperfibrinolytic hemorrhages and traumatic hemorrhagic shock.

Aprotinin is known to inhibit several serine proteases including trypsin, chymotrypsin, plasmin and kallikrein, and is used therapeutically in the treatment of acute pancreatitis, various states of shock syndrome, hyperfibrinolytic hemorrhage and myocardial infarction (Trapnell et al., (1974) Brit J. Surg. 61: 177; J. McMichan et al., (1982) Circulatory Shock 9: 107; Auer et al., (1979)Acta Neurochir. 49: 207; Sher (1977) Am J. Obstet. Gynecol. 129: 164; Schneider (1976), Artzneim.-Firsch. 26: 1606). It is generally thought that Trasylol® reduces blood loss in vivo through inhibition of kallikrein and plasmin. It has been found that aprotinin (3–58, Arg15, Ala17, Ser42) exhibits improved plasma kallikrein inhibitory potency as compared to native aprotinin itself (WO 89/10374).

Problems With Aprotinin

Because aprotinin is of bovine origin, there is a finite risk of inducing anaphylaxis in human patients upon re-exposure to the drug. Thus, a human functional equivalent to aprotinin, by virtue of a lower risk of anaphylaxis, would be most useful and desirable to have.

Aprotinin is also nephrotoxic in rodents and dogs when administered repeatedly at high dose (Bayer, Trasylol®, Inhibitor of proteinase; Glasser et al., in "Verhandlungen der Deutschen Gesellschaft fur Innere Medizin, 78. Kongress", Bergmann, Munchen, 1972 pp. 1612–1614). One hypothesis ascribes this effect to the accumulation of aprotinin in the negatively charged proximal tubules of the kidney, due to its high net positive charge (WO 93/14120).

Accordingly, an object of the present invention is to identify human proteins with functional activity similar to aprotinin. It was also an object of the instant invention to identify human proteins, that would be less charged, yet exhibit the same, highly similar, or improved protease specificities as found for aprotinin, especially with respect to the potency of plasmin and kallikrein inhibition. Such inhibitors could then be used repeatedly as medicaments in human patients with reduced risk of adverse immune response and reduced nephrotoxicity.

BRIEF SUMMARY OF THE INVENTION

The instant invention provides for a purified human serine protease inhibitor which can specifically inhibit kallikrein, that has been isolated from human placental tissue via affinity chromatography.

The instant invention provides a newly identified human protein herein called human placental bikunin that contains two serine protease inhibitor domains of the Kunitz class. In one particular embodiment, the instant invention embodies a protein having the amino acid sequence:

```
ADRERSIHDF CLVSKVVGRC RASMPRWWYN VTDGSCQLFV YGGCDGNSNN  50   (SEQ ID NO:1)

YLTKEECLKK CATVTENATG DLATSRNAAD SSVPSAPRRQ DSEDHSSDMF 100

NYEEYCTANA VTGPCRASFP RWYFDVERNS CNNFIYGGCR GNKNSYRSEE 150

ACMLRCFRQQ ENPPLPLGSK VVVLAGAVS                        179
```

In a prefered embodiment the instant invention provides for native human placental bikunin protein having the amino acid sequence:

```
ADRERSIHDF CLVSKVVGRC RASMPRWWYN VTDGSCQLFV YGGCDGNSNN  50   (SEQ ID NO:52)

YLTKEECLKK CATVTENATG DLATSRNAAD SSVPSAPRRQ DSEDHSSDMF 100

NYEEYCTANA VTGPCRASFP RWYFDVERNS CNNFIYGGCR GNKNSYRSEE 150

ACMLRCFRQQ ENPPLPLGSK                                  170
```

In one aspect, the biological activity of the protein of the instant invention is that it can bind to and substantially inhibit the biological activity of trypsin, human plasma and tissue kallikreins, human plasmin and Factor XIIa. In a preferred embodiment, the present invention provides for a native human placental bikunin protein, in glycosylated form. In a further embodiment the instant invention encompasses native human bikunin protein which has been formed such that it contains at least one cysteine-cysteine disulfide bond. In a preferred embodiment, the protein contains at least one intra-chain cysteine-cysteine disulfide bond formed between a pair of cysteines selected from the group consisting of CYS11-CYS61, CYS20-CYS44, CYS36-CYS57, CYS106-CYS156, CYS115-CYS139, and CYS131-CYS152, wherein the cysteines are numbered according to the amino acid sequence of native human placental bikunin. One of ordinary skill will recognize that the protein of the instant invention may fold into the proper three-dimensional conformation, such that the biological activity of native human bikunin is maintained, where none, one or more, or all of the native intra-chain cysteine-cysteine disulfide bonds are present. In a most preferred embodiment, the protein of the instant invention is properly folded and is formed with all of the proper native cysteine-cysteine disulfide bonds.

Active protein of the instant invention can be obtained by purification from human tissue, such as placenta, or via synthetic protein chemistry techniques, as illustrated by the Examples below. It is also understood that the protein of the instant invention may be obtained using molecular biology techniques, where self-replicating vectors are capable of expressing the protein of the instant invention from transformed cells. Such protein can be made as non-secreted, or secreted forms from transformed cells. In order to facilitate secretion from transformed cells, to enhance the functional stability of the translated protein, or to aid folding of the bikunin protein, certain signal peptide sequences may be added to the NH2-terminal portion of the native human bikunin protein.

In one embodiment, the instant invention thus provides for the native human bikunin protein with at least a portion of the native signal peptide sequence intact. Thus one embodiment of the invention provides for native human bikunin with at least part of the signal peptide, having the amino acid sequence:

```
AGSFLAWLGSLLLSGVLA                                  -1   (SEQ ID NO:2)

ADRERSIHDFCLVSKVVGRCRASMPRWWYNVTDGSCQLFVYGGCDGNSNN   50

YLTKEECLKKCATVTENATGDLATSRNAADSSVPSAPRRQDSEDHSSDMF  100

NYEEYCTANAVTGPCRASFPRWYFDVERNSCNNFIYGGCRGNKNSYRSEE  150

ACMLRCFRQQENPPLPLGSKVVVLAGAVS                       179
```

In a prefered embodiment the instant invention provides for a native human placental bikunin protein with part of the leader sequence intact, having the amino acid sequence of SEQ ID NO: 52 with an intact leader segment having the amino acid sequence:

MAQLCGL RRSRAFLALL GSLLLSGVLA-1 (SEQ ID NO: 53)

In another embodiment, the instant invention provides for bikunin protein with part of the leader sequence intact, having the amino acid sequence of SEQ ID NO: 52 with the intact leader segment having the amino acid sequence:

MLR AEADGVSRLL GSLLLSGVLA-1 (SEQ ID NO: 54)

In a preferred numbering system used herein the amino acid numbered+1 is assigned to the NH2-terminus of the amino acid sequence for native human placental bikunin. One will readily recognize that functional protein fragments can be derived from native human placental bikunin, which will maintain at least part of the biological activity of native human placental bikunin, and act as serine protease inhibitors.

In one embodiment, the protein of the instant invention comprises a fragment of native human placental bikunin, which contains at least one functional Kunitz-like domain, having the amino acid sequence of native human placental bikunin amino acids 7–159, hereinafter called "bikunin (7–159)". Thus the instant invention embodies a protein having the amino acid sequence:

```
IHDFCLVSKVVGRCRASMPRWWYNVTDGSCQLFVYGGCDGNSNN        50   (SEQ ID NO:3)

YLTKEECLKKCATVTENATGDLATSRNAADSSVPSAPRRQDSEDHSSDMF  100

NYEEYCTANAVTGPCRASFPRWYFDVERNSCNNFIYGGCRGNKNSYRSEE  150

ACMLRCFRQ                                           159
``` where the amino acid numbering corresponds to that of the amino acid sequence of native human placental bikunin. Another functional variant of this embodiment can be the fragment of native human placental bikunin, which contains at least one functional Kunitz-like domain, having the amino acid sequence of native human placental bikunin amino acids 11–156, bikunin (11–156)

```
CLVSKVVGRCRASMPRWWYNVTDGSCQLFVYGGCDGNSNN          50   (SEQ ID NO:50).

YLTKEECLKKCATVTENATGDLATSRNAADSSVPSAPRRQDSEDHSSDMF 100

NYEEYCTANAVTGPCRASFPRWYFDVERNSCNNFIYGGCRGNKNSYRSEE 150

ACMLRC                                           156
```

One can recognize that the individual Kunitz-like domains are also fragments of the native placental bikunin. In particular, the instant invention provides for a protein having the amino acid sequence of a first Kunitz-like domain consisting of the amino acid sequence of native human placental bikunin amino acids 7–64, hereinafter called "bikunin (7–64)". Thus in one embodiment the instant invention encompasses a protein which contains at least one Kunitz-like domain having the amino acid sequence:

Thus one of ordinary skill will recognize that fragments of the native human bikunin protein can be made which will retain at least some of the native protein biological activity. Such fragments can also be combined in different orientations or multiple combinations to provide for alternative proteins which retain some of, the same, or more biological activity of the native human bikunin protein.

```
IHDFCLVSKVVGRCRASMPRWWYNVTDGSCQLFVYGGCDGNSNN 50  (SEQ ID NO:4)

YLTKEECLKKCATV                               64
``` where the amino acid numbering corresponds to that of the amino acid sequence of native human placental bikunin. Another form of the protein of the instant invention can be a first Kunitz-like domain consisting of the amino acid sequence of native human placental bikunin amino acids 11–61, "bikunin (11–61)" having the amino acid sequence:

```
                                         (SEQ ID NO:5)
CLVSKVVGRCRASMPRWWYNVTDGSCQLFVYGGCDGNSNN  50

YLTKEECLKKC                               61
```

The instant invention also provides for a protein having the amino acid sequence of a Kunitz-like domain consisting of the amino acid sequence of native human placental bikunin amino acids 102–159, hereinafter called "bikunin (102–159)". Thus one embodiment the instant invention encompasses a protein which contains at least one Kunitz-like domain having the amino acid sequence:

One will readily recognize that biologically active protein of the instant invention may comprise one or more of the instant Kunitz-like domains in combination with additional Kunitz-like domains from other sources. Biologically active protein of the instant invention may comprise one or more of the instant Kunitz-like domains in combination with additional protein domains from other sources with a variety of biological activities. The biological activity of the protein of the instant invention can be combined with that of other known protein or proteins to provide for multifunctional fusion proteins having predictable biological activity. Thus, in one embodiment, the instant invention encompasses a protein which contains at least one amino acid sequence segment the same as, or functionally equivalent to the amino acid sequence of either SEQ ID NO: 5 or SEQ ID NO: 7.

```
YEEYCTANAVTGPCRASFPRWYFDVERNSCNNFIYGGCRGNKNSYRSEE 150  (SEQ ID NO:6)

ACMLRCFRQ                                        159
``` where the amino acid numbering corresponds to that of the amino acid sequence of native human placental bikunin. Another form of this domain can be a Kunitz-like domain consisting of the amino acid sequence of native human placental bikunin amino acids 106–156, "bikunin (106–156)" having the amino acid sequence:

An open reading frame which terminates at an early stop codon can still code for a functional protein. The instant invention encompasses such alternative termination, and in one embodiment provides for a protein of the amino acid sequence:

```
CTANAVTGPCRASFPRWYFDVERNSCNNFIYGGCRGNKNSYRSEE 150  (SEQ ID NO:7)

ACMLRC                                        156
```

```
ADRERSIHDFCLVSKVVGRCRASMPRWWYNVTDGSCQLFVYGGCDGNSNN  50  (SEQ ID NO:8)

YLTKEECLKKCATVTENATGDLATSRNAADSSVPSAPRRQDS          92
```

In one embodiment, the instant invention provides for substantially purified, or recombinantly produced native human bikunin protein with an intact segment of the leader sequence, and at least a portion of the native transmembrane region intact. Thus one embodiment of the invention provides for native human bikunin, with an intact leader sequence, and with at least part of the transmembrane domain (underlined), having an amino acid sequence selected from:

```
1) EST                  MLR AEADGVSRLL GSLLLSGVLA    -1
2) PCR                  MAQLCGL RRSRAFLALL GSLLLSGVLA -1
3) λcDNA                MAQLCGL RRSRAFLALL GSLLLSGVLA -1

1) ADRERSIHDF CLVSKVVGRC RASMPRWWYN VTDGSCQLFV YGGCDGNSNN 50
2) ADRERSIHDF CLVSKVVGRC RASMPRWWYN VTDGSCQLFV YGGCDGNSNN 50
3) ADRERSIHDF CLVSKVVGRC RASMPRWWYN VTDGSCQLFV YGGCDGNSNN 50

1) YLTKEECLKK CATVTENATG DLATSRNAAD SSVPSAPRRQ DSEDHSSDMF 100
2) YLTKEECLKK CATVTENATG DLATSRNAAD SSVPSAPRRQ DSEDHSSDMF 100
3) YLTKEECLKK CATVTENATG DLATSRNAAD SSVPSAPRRQ DSEDHSSDMF 100

1) NYEEYCTANA VTGPCRASFP RWYFDVERNS CNNFIYGGCR GKNSYRSEE 150
2) NYEEYCTANA VTGPCRASFP RWYFDVERNS CNNFIYGGCR GKNSYRSEE 150
3) NYEEYCTANA VTGPCRASFP RWYFDVERNS CNNFIYGGCR GKNSYRSEE 150

1) ACMLRCFRQQ ENPPLPLGSK VVVLAGLFVM VLILFLGASM VYLIRVARRN 200
2) ACMLRCFRQQ ENPPLPLGSK VVVLAGLFVM VLILFLGASM VYLIRVARRN 200
3) ACMLRCFRQQ ENPPLPLGSK VVVLAGLFVM VLILFLGASM VYLIRVARRN 200

1) QERALRTVWS SGDDKEQLVK NTYVL                      225
2) QERALRTVWS FGD                                   213
3) QERALRTVWS SGDDKEQLVK NTYVL                      225
``` where sequence 1) is EST derived consensus SEQ ID NO: 45, 2) is PCR clone SEQ ID NO:47, and 3) is lambda cDNA clone SEQ ID NO:49. In a preferred embodiment a protein of the instant invention comprises one of the amino acid sequence of SEQ ID NO: 45, 47 or 49 wherein the protein has been cleaved in the region between the end of the last Kunitz domain and the transmembrane region.

The instant invention also embodies the protein wherein the signal peptide is deleted. Thus the instant invention provides for a protein having the amino acid sequence of SEQ ID NO: 52 continuous with a transmembrane amino acid sequence:

```
                                        (SEQ ID NO:69)
EST  VVVLAGLFVM VLILFLGASM VYLIRVARRN      200

EST  QERALRTVWS SGDDKEQLVK NTYVL            225
``` a transmembrane amino acid sequence:

```
                                        (SEQ ID NO:68)
PCR  VVVLAGLFVM VLILFLGASM VYLIRVARRN      200

PCR  QERALRTVWS FGD                         213
``` or a transmembrane amino acid sequence:

```
                                        (SEQ ID NO:67)
λcDNA  VVVLAGLFVM VLILFLGASM VYLIRVARRN    200

λcDNA  QERALRTVWS SGDDKEQLVK NTYVL          225
```

The protein amino acid sequences of the instant invention clearly teach one of the art the appropriate nucleic acid sequences which can be used in molecular biology techniques to produce the proteins of the instant invention. Thus, one embodiment of the instant invention provides for a nucleic acid sequence which encodes for a human bikunin having the consensus DNA sequence of FIG. 3 (SEQ ID NO: 9), which translates into the amino acid sequence for native human placental bikunin sequence of FIG. 3 (SEQ ID NO: 10). In another embodiment, the instant invention provides for a consensus nucleic acid sequence of FIG. 4C (SEQ ID NO: 51) which encodes for an amino acid sequence of FIG. 4D (SEQ ID NO: 45).

In a preferred embodiment, the instant invention provides for a nucleic acid sequence which encodes for native human placental bikunin having the DNA sequence of FIG. 4F (SEQ ID NO: 48) which encodes for the protein sequence of SEQ ID NO: 49. In an another embodiment, the instant invention provides for a nucleic acid sequence of FIG. 4E (SEQ ID NO: 46) which encodes for a protein sequence of SEQ ID NO: 47.

One can easily recognize that certain allelic mutations, and conservative substitutions made in the nucleic acid sequence can be made which will still result in a protein amino acid sequence encompassed by the instant invention. One of skill in the art can recognize that certain natural allelic mutations of the protein of the instant invention, and conservative substitutions of amino acids in the protein of the instant invention will not significantly alter the biological activity of the protein, and are encompassed by the instant invention.

The instant invention also provides for pharmaceutical compositions containing human placental bikunin and fragments thereof that are useful for the reduction of perioperative blood loss in a patient undergoing surgery.

The present invention also provides methods for reducing perioperative blood loss in a patient undergoing surgery, wherein an effective amount of the disclosed human serine protease inhibitors of the present invention in a biologically compatible vehicle is administered to the patient.

The present invention also provides for variants of placental bikunin, and the specific Kunitz domains described above, that contain amino acid substitutions that alter the protease specificity. Preferred sites of substitution are indicated below as positions $Xaa^1$ through $Xaa^{32}$ in the amino acid sequence for native placental bikunin. Substitutions at $Xaa^1$ through $Xaa^{16}$ are also preferred for variants of bikunin (7–64), while substitutions at $Xaa^{17}$ through $Xaa^{32}$ are preferred for variants of bikunin (102–159).

Thus the present invention embodies protein having an amino acid sequence:

```
Ala Asp Arg Glu Arg Ser Ile Xaa¹ Asp Phe              10 (SEQ ID NO: 11)

Cys Leu Val Ser Lys Val Xaa² Gly Xaa³ Cys             20

Xaa⁴ Xaa⁵ Xaa⁶ Xaa⁷ Xaa⁸ Xaa⁹ Trp Trp Tyr Asn         30

Val Thr Asp Gly Ser Cys Gln Leu Phe Xaa¹⁰            40

Tyr Xaa¹¹ Gly Cys Xaa¹² Xaa¹³ Xaa¹⁴ Ser Asn Asn      50

Tyr Xaa¹⁵ Thr Lys Glu Glu Cys Leu Lys Lys            60

Cys Ala Thr Xaa¹⁶ Thr Glu Asn Ala Thr Gly            70

Asp Leu Ser Thr Ser Arg Asn Ala Ala Asp              80

Ser Ser Val Pro Ser Ala Pro Arg Arg Gln              90

Asp Ser Glu His Asp Ser Ser Asp Met Phe              100

Asn Tyr Xaa¹⁷ Glu Tyr Cys Thr Ala Asn Ala            110

Val Xaa¹⁸ Gly Xaa¹⁹ Cys Xaa²⁰ Xaa²¹ Xaa²² Xaa²³ Xaa²⁴ 120

Xaa²⁵ Trp Tyr Phe Asp Val Glu Arg Asn Ser            130

Cys Asn Asn Phe Xaa²⁶ Tyr Xaa²⁷ Gly Cys Xaa²⁸        140

Xaa²⁹ Xaa³⁰ Lys Asn Ser Tyr Xaa³¹ Ser Glu Glu        150

Ala Cys Met Leu Arg Cys Phe Arg Xaa³² Gln            160

Glu Asn Pro Pro Leu Pro Leu Gly Ser Lys             170

Val Val Val Leu Ala Gly Ala Val Ser.                179
``` where $Xaa^1$–$Xaa^{32}$ each independently represents a naturally occurring amino acid residue except Cys, with the proviso that at least one of the amino acid residues $Xaa^1$–$Xaa^{32}$ is different from the corresponding amino acid residue of the native sequence.

In the present context, the term "naturally occurring amino acid residue" is intended to indicate any one of the 20 commonly occurring amino acids, i.e., Ala, Arg, Asn, Asp, Cys, Gln, Glu, Gly, His, Ile, Leu, Lys, Met, Phe, Pro, Ser, Thr, Trp, Tyr and Val.

By substituting one or more amino acids in one or more of the positions indicated above, it may be possible to change the inhibitor specificity profile of native placental bikunin or that of the individual Kunitz-like domains, bikunin(7–64) or bikunin (102–159) so that it preferentially inhibits other serine proteases such as, but not limited to, the enzymes of the complement cascade, TF/FVIIa, FXa, thrombin, neutrophil elastase, cathepsin G or proteinase-3.

Examples of preferred variants of placental bikunin include those wherein $Xaa^1$ is an amino acid residue selected from the group consisting of His, Glu, Pro, Ala, Val or Lys, in particular wherein $Xaa^1$ is His or Pro; or wherein $Xaa^2$ is an amino acid residue selected from the group consisting of Val, Thr, Asp, Pro, Arg, Tyr, Glu, Ala, Lys, in particular wherein $Xaa^2$ is Val or Thr; or wherein $Xaa^3$ is an amino acid residue selected from the group consisting of Arg, Pro, Ile, Leu, Thr, in particular wherein $Xaa^3$ is Arg or Pro; or wherein $Xaa^4$ is an amino acid residue selected from the group consisting of Arg, Lys and Ser, Gln, in particular wherein $Xaa^4$ is Arg or Lys; or wherein $Xaa^5$ is an amino acid residue selected from the group consisting of Ala, Gly, Asp, Thr, in particular wherein $Xaa^5$ is Ala; or wherein $Xaa^6$ is an amino acid residue selected from the group consisting of Ser, Ile, Tyr, Asn, Leu, Val, Arg, Phe, in particular wherein $Xaa^6$ is Ser or Arg; or wherein $Xaa^7$ is an amino acid residue selected from the group consisting of Met, Phe, Ile, Glu, Leu, Thr and Val, in particular wherein $Xaa^7$ is Met or Ile; or wherein $Xaa^8$ is an amino acid residue selected from the group consisting of Pro, Lys, Thr, Gln, Asn, Leu, Ser or Ile, in particular wherein $Xaa^8$ is Pro or Ile; or wherein $Xaa^9$ is an amino acid residue selected from the group consisting of Arg, Lys or Leu, in particular wherein $Xaa^9$ is Arg: or wherein $Xaa^{10}$ is an amino acid residue selected from the group consisting of Val, Ile, Lys, Ala, Pro, Phe, Trp, Gln, Leu and Thr, in particular wherein $Xaa^{10}$ is Val; or wherein $Xaa^{11}$ is an amino acid residue selected from the group consisting of Gly, Ser and Thr, in particular wherein $Xaa^{11}$ is Gly; or wherein $Xaa^{12}$ is an amino acid residue selected from the group consisting of Asp, Arg, Glu, Leu, Gln, Gly, in particular wherein $Xaa^{12}$ is Asp or Arg; or wherein $Xaa^{13}$ is an amino acid residue selected from the group consisting of Gly and Ala; or wherein Xaa$^{14}$ is an amino acid residue selected from the group consisting of Asn or Lys; or wherein Xaa$^{15}$ is an amino acid residue selected from the group consisting of Gly, Asp, Leu, Arg, Glu, Thr, Tyr, Val, and Lys, in particular wherein Xaa$^{15}$ is Leu or Lys; or wherein Xaa$^{16}$ is an amino acid residue selected from the group consisting of Val, Gln, Asp, Gly, Ile, Ala, Met, and Val, in particular wherein Xaa$^{16}$ is Val or Ala; or wherein Xaa$^{17}$ is an amino acid residue selected from the group consisting of His, Glu, Pro, Ala, Lys and Val, in particular wherein Xaa$^{17}$ is Glu or Pro; or wherein Xaa$^{18}$ is an amino acid residue selected from the group consisting of Val, Thr, Asp, Pro, Arg, Tyr, Glu, Ala or Lys, in particular wherein Xaa$^{18}$ is Thr; or wherein Xaa$^{19}$ is an amino acid residue selected from the group consisting of Arg, Pro, Ile, Leu or Thr, in particular wherein Xaa$^{19}$ is Pro; or wherein Xaa$^{20}$ is an amino acid residue selected from the group consisting of Arg, Lys, Gln and Ser, in particular wherein Xaa$^{20}$ is Arg or Lys; or wherein Xaa$^{21}$ is an amino acid residue selected from the group consisting of Ala, Asp, Thr or Gly; in particular wherein Xaa$^{21}$ is Ala; or wherein Xaa$^{22}$ is an amino acid residue selected from the group consisting of Ser, Ile, Tyr, Asn, Leu, Val, Arg or Phe, in particular wherein Xaa$^{22}$ is Ser or Arg; or wherein Xaa$^{23}$ is an amino acid residue selected from the group consisting of Met, Phe, Ile, Glu, Leu, Thr and Val, in particular wherein Xaa$^{23}$ is Phe or Ile; or wherein Xaa$^{24}$ is an amino acid residue selected from the group consisting of Pro, Lys, Thr, Asn, Leu, Gln, Ser or Ile, in particular wherein Xaa$^{24}$ is Pro or Ile; or wherein Xaa25 is an amino acid residue selected from the group consisting of Arg, Lys or Leu, in particular wherein Xaa$^{25}$ is Arg: or wherein Xaa$^{26}$ is an amino acid residue selected from the group consisting of Val, Ile, Lys, Leu, Ala, Pro, Phe, Gln, Trp and Thr, in particular wherein Xaa$^{26}$ is Val or Ile; or wherein Xaa$^{27}$ is an amino acid residue selected from the group consisting of Gly, Ser and Thr, in particular wherein Xaa$^{27}$ is Gly; or wherein Xaa$^{28}$ is an amino acid residue selected from the group consisting of Asp, Arg, Glu, Leu, Gly or Gln, in particular wherein Xaa$^{28}$ is Arg; or wherein Xaa$^{29}$ is an amino acid residue selected from the group consisting of Gly and Ala; or wherein Xaa$^{30}$ is an amino acid residue selected from the group consisting of Asn or Lys; or wherein Xaa$^{31}$ is an amino acid residue selected from the group consisting of Gly, Asp, Leu, Arg, Glu, Thr, Tyr, Val, and Lys, in particular wherein Xaa$^{31}$ is Arg or Lys; or wherein Xaa$^{32}$ is an amino acid residue selected from the group consisting of Val, Gln, Asp, Gly, Ile, Ala, Met, and Thr, in particular wherein Xaa$^{32}$ is Gln or Ala.

DESCRIPTION OF THE DRAWINGS

The invention will be better understood from a consideration of the following detailed description and claims, taken in conjunction with the drawings, in which:

FIG. 1 depicts the nucleotide sequence of EST R35464 (SEQ ID NO: 12) and the translation of this DNA sequence (SEQ ID NO: 13) which yielded an open reading frame with some sequence similarity to aprotinin. The translation product contains 5 of the 6 cysteines in the correct spacing that is characteristic for Kunitz-like inhibitor domains (indicated in bold). The position normally occupied by the remaining cysteine (at codon 38) contained instead a phenylalanine (indicated by an asterisk).

FIG. 2 depicts the nucleotide sequence of EST R74593 (SEQ ID NO: 14), and the translation of this DNA sequence (SEQ ID NO: 15) which yielded an open reading frame with homology to the Kunitz class of serine protease inhibitor domains. The translation product contained 6 cysteines in the correct spacing that is characteristic for Kunitz-like inhibitor domains (indicated in bold). However, this reading frame sequence includes stop codons at codon 3 and 23.

FIGS. 3A–1 and 3A–2 depict a deduced nucleic acid sequence of human placental bikunin (SEQ ID NO: 9) labeled "consensus" and matched with the translated protein amino acid sequence labeled "translated" (SEQ ID NO: 10). Also as comparison are shown the nucleic acid sequence for ESTs H94519 (SEQ ID NO: 16), N39798 (SEQ ID NO: 17), R74593 (SEQ ID NO: 14) and R35464 (SEQ ID NO: 12). The underlined nucleotides in the consensus sequence correspond to the site of PCR primers described in the Examples. Underlined amino acids in the translated consensus sequence are residues whose identity have been confirmed by amino acid sequencing of purified native human placental bikunin. Nucleotide and amino acid code are standard single letter code, "N" in the nucleic acid code indicates an unassigned nucleic acid, and "*" indicates a stop codon in the amino acid sequence.

FIG. 4A depicts the original overlay of a series of ESTs with some nucleic acid sequence homology to ESTs encoding human placental bikunin, or portions thereof. Shown for reference are the relative positions of bikunin (7–64) and bikunin (102–159), labeled KID1 and KID2 respectively.

FIGS. 4C–1 through 4C–20 depict the corresponding alignment of the oligonucleotide sequences of each of the overlapping ESTs shown schematically in FIG. 4B. The upper sequence (SEQ ID NO: 51) labeled bikunin represents the consensus oligonucleotide sequence derived from the overlapping nucleotides at each position. The numbers refer to base-pair position within the EST map. The oligonucleotides in EST R74593 that are bold underlined (at map positions 994 and 1005) are base insertions observed in R74593 that were consistently absent in each of the other overlapping ESTs.

FIG. 4D depicts the amino acid translation of the consensus oligonucleotide sequence for bikunin depicted in FIG. 4C (SEQ ID NO: 45).

FIG. 4E depicts the nucleotide sequence (SEQ ID NO: 46) and corresponding amino acid translation (SEQ ID NO: 47) of a placental bikunin encoding sequence that was derived from a human placental cDNA library by PCR-based amplification.

FIGS. 4F–1 and 4F–2 depict the nucleotide sequence (SEQ ID NO: 48) and corresponding amino acid translation (SEQ ID NO: 49) of a native human placental bikunin encoding clone that was isolated from a human placental lambda cDNA library by colony hybridization.

FIG. 4G compares the alignment of the amino acid translated oligonucleotide sequences for placental bikunin obtained by EST overlay (SEQ ID NO: 45), PCR based cloning (SEQ ID NO: 47), and conventional lambda colony hybridization (SEQ ID NO: 49).

FIG. 5 shows a graph of purification of human placental bikunin from placental tissue after Superdex 75 Gel-Filtration. The plot is an overlay of the protein elution profile as measured by OD 280 nm (solid line), activity of eluted protein in a trypsin inhibition assay (% inhibition shown by circles), and activity of eluted protein in a kallikrein inhibition assay (% inhibition shown by squares).

FIG. 6 shows a graph which plots the purification of human placental bikunin from placental tissue using C18 Reverse-Phase Chromatography. The plot is an overlay of the protein elution profile as measured by OD 215 nm (solid line), activity of eluted protein in a trypsin inhibition assay (% inhibition shown by circles), and activity of eluted protein in a kallikrein inhibition assay (% inhibition shown by squares).

FIG. 7 depicts a silver stained SDS-PAGE gel of highly purified placental bikunin (lane 2), and a series of molecular size marker proteins (lane 1) of the indicated sizes in kilodaltons. Migration was from top to bottom.

FIGS. 9A and 9B show a silver stained SDS-PAGE (9A) and a Western blot with anti-placental bikunin (102–159) pAb (9B) of cell-free fermentation broth from the growth of yeast strain SC101 (recombinants 2.4 and 2.5) that was stably transformed with a plasmid directing the expression of either bovine aprotinin, or placental bikunin (102–159). Migration was from top to bottom.

FIG. 10 is a photograph which shows a silver stained SDS-PAGE of highly purified placental bikunin (102–159) (lane 2) and a series of molecular size marker proteins (lane 1) of the indicated sizes in Kilodaltons. Migration was from top to bottom.

FIGS. 11A and 11B are a photograph which shows the results of Northern blots of mRNA from various human tissues that was hybridized to a 32P labeled cDNA probe encoding either placental bikunin (102–159) (panel 11A) or encoding placental bikunin (1–213) (panel 11B). Migration was from top to bottom. The numbers to the right of each blot refer to the size in kilobases of the adjacent RNA markers. The organs from which mRNA was derived is described under each lane of the blot.

FIGS. 12A and 12B depict an immunoblot of placental derived placental bikunin with rabbit antiserum raised against either synthetic reduced placental bikunin (7–64) (panel A) or 102–159 (panel B). For each panel, contents were: molecular size markers (lanes 1); native placental bikunin isolated from human placenta (lanes 2); synthetic placental bikunin (7–64) (lanes 3) and synthetic placental bikunin (102–159) (lanes 4). Tricine 10–20% SDS-PAGE gels were blotted and developed with protein A-purified primary polyclonal antibody (8 ug IgG in 20 ml 0.1% BSA/Tris-buffered saline (pH 7.5), followed by alkaline phosphatase-conjugated goat anti-rabbit secondary antibody. Migration was from top to bottom.

FIG. 13 depicts a Coomassie Blue stained 10–20% Tricine SDS-PAGE gel of 3 micrograms of highly purified placental bikunin (1–170) derived from a baculovirus/Sf9 expression system (lane 2). Lane 1 contains molecular size markers. Migration was from top to bottom.

FIG. 14 depicts a comparison of the effect of increasing concentrations of either Sf9-derived human placental bikunin (1–170) (filled circles), synthetic placental bikunin (102–159) (open circles), or aprotinin (open squares) on the activated partial thromboplastin time of human plasma. Clotting was initiated with $CaCl_2$. The concentration of proteins are plotted versus the -fold prolongation in clotting time. The uninhibited clotting time was 30.8 seconds.

DETAILED DESCRIPTION OF THE INVENTION

Figure 4:
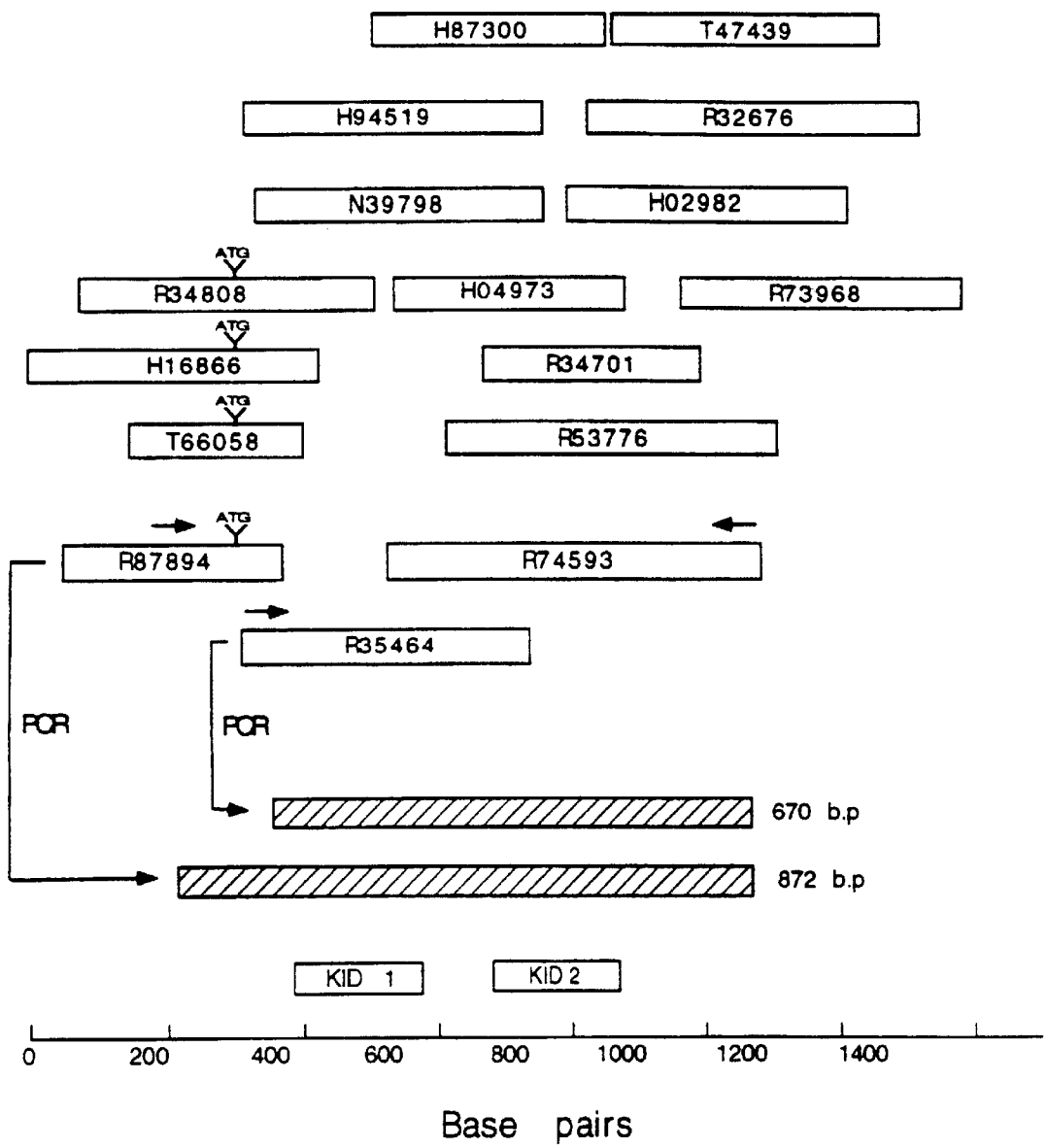

The present invention encompasses a newly identified human protein herein called human placental bikunin that contains two serine protease inhibitor domains of the Kunitz class. The instant invention also encompasses pharmaceutical compositions containing placental bikunin and fragments thereof that are useful for the reduction of perioperative blood loss in a patient undergoing surgery, or with major trauma.

The present invention also provides methods for reducing perioperative blood loss in a patient undergoing surgery or due to major trauma, wherein an effective amount of the disclosed human serine protease inhibitors of the present invention, in a biologically compatible vehicle, is administered to the patient.

A preferred application for placental bikunin, isolated domains, and other variants is for the reduction of blood loss resulting from trauma or surgery that has the potential for loss of large volumes of blood. These methods and compositions reduce or eliminate the need for whole donor blood or blood products, thereby reducing the risk of infection and other adverse side effects, as well as the cost of surgery. The methods are thus useful in reducing blood loss in normal patients, i.e., those not suffering from inborn or other preoperative deficiencies in coagulation factors. The reduction in blood loss is seen as a reduction in blood loss during surgery, as reduced post surgical drainage or both. Preferred surgical applications include but are not limited to use in thoracic and abdominal surgery, total and partial hip replacement surgeries and surgeries to treat a patient having an epithelial lesion of the eye. Preferred thoracic surgical procedures include but are not limited to aortocoronary bypass, excision of cardiac and aortic aneurysms, and surgery for esophageal varices, and coronary artery bypass surgery. Preferred abdominal surgeries include but are not limited to liver transplants, radical prostatectomy, surgery for diverticulitis of colon, tumor debulking, surgery on the abdominal aorta and surgery for duodenal ulcers, and repair of liver or spleen trauma. Preferred use for the treatment of trauma include but are not limited to the use in stabilization of severely injured patients at accident sites suffering from e.g., limb loss or major thoracic/abdominal wounds. In case of use for the reduction of blood loss resulting from surgery it is preferred to administer the placental bikunin, isolated domains, or other variant prior to and during surgery, whereas in case of use in trauma settings the placental bikunin variant, isolated domain or other variant is to be administered as rapidly as possible following injury, and should be contained on emergency vehicles traveling to the accident sites.

Factor XII (also known as Hageman Factor) is a serine protease that is found in the circulation in a zymogen form (80 kD) at approximately 29–40 µg/ml (see Pixley, et al. (1993) *Meth. in Enz.*, 222, 51–64) and is activated by tissue and plasma kallikrein. Once activated, it participates in the intrinsic pathway of blood coagulation which is activated when blood or plasma contacts a "foreign" or anionic surface. Once activated, Factor XIIa can then cleave and activate a number of other plasma proteases including Factor XI, prekallikrein, and C1 of the complement system. Thus Factor XII may be involved in causing hypotensive reactions since activated kallikrein can cleave kininogen releasing bradykinin (see Colman, (1984) *J. Clin. Invest.*, 73, 1249).

Sepsis is a disease that results from bacterial infection due to bacterial endotoxin or lipopolysaccharide (LPS). Exposure of Factor XII to LPS results in the activation of Factor XII. Patients with sepsis frequently have symptoms of intravascular coagulation which may also be due to activation of Factor XII by LPS. Septic shock can result from bacterial infection and is associated with fever, low systemic vascular resistance, and low arterial pressure. It is a common cause of death in intensive care units in the United States, where seventy five percent of the patients that die from septic shock have a persistent hypotension (see Parillo, et al. (1989) Ann Rev. Med., 40, 469485).

Adult respiratory distress syndrome is characterized by pulmonary edema, hypoxemia, and decreased pulmonary compliance. The pathogenesis of the disease is currently unknown although the proteolytic pathways of coagulation and fibrinolysis are believed to play a role (see Carvalho, et al. (1988) J. Lab Clin. Med., 112: 270–277).

The proteins of the instant invention are also a novel human Kunitz type inhibitor of kallikrein, an activator of Factor XII. Thus another object of the current invention is to present a method for the prophylactic or therapeutic treatment of systemic inflammatory reactions such as septic shock, adult respiratory distress syndrome (ARDS), preeclampsia, multiple organ failure and disseminated intravascular coagulation (DIC). The therapeutic or prophylactic administration of the peptides of the instant invention would result in the modulation of these inflammatory conditions and be beneficial to the patient.

Plasmin plays an important role in extracellular matrix degradation and the activation of matrix-metallo protease (MMP) cascades. Collectively these proteases mediate migration of and tissue invasion by both endothelial cells during angiogenesis/neovascularization, and cancer cells during metastasis. Neovascularization is essential to support tumor growth and metastasis is a process which mediates the spreading of tumors and which is associated with extremely poor patient prognosis.

Several preclinical studies suggest that Kunitz like serine protease inhibitors with a protease specificity similar to aprotinin are useful as medicaments for cancer. For example, aprotinin reduced tumor growth and invasion, with increased tumor necrosis when administered to hamsters bearing a highly invasive fibrosarcoma or to mice bearing a similarly malignant mammary carcinoma (Latner et al., (1974), Br. J. Cancer 30: 60–67; Latner and Turner, (1976), Br. J. Cancer 33: 535–538). Furthermore, administration of 200,000 KIU of aprotinin i.p. to C57B1/6 Cr male mice on days 1 to 14 post-inoculation with Lewis lung carcinoma cells, reduced pulmonary metastases by 50% although had no effect on primary tumor mass (Giraldi et al., (1977) Eur. J. Cancer, 13: 1321–1323). Similarly, administration of 10,000 KIU i.p. on each of days 13–16 post-inoculation of C57BL/6J mice with Lewis tumor cells inhibited pulmonary metastases by 90% without affecting the primary tumor growth (Uetsuji et al., (1992), Jpn. J. Surg. 22: 429–442). In this same study, administration of plasmin or kallikrein with the same dosing schedule was argued to increase the number of pulmonary metastases. These results prompted the authors to suggest that perioperative administration of aprotinin to cancer patients may reduce the likelihood of metastases. Black and Steger (1976, Eur. J. Pharmacol., 38: 313–319) found that aprotinin inhibited the growth of the transplanted rodent Murphy-Strum lymphosarcoma in rats and suggested that the effect involved the inhibition of the kinin-forming enzyme system. Twice daily i.p. injection of female ddY mice with 10,000 KIU of aprotinin for 7 weeks to mice each bearing a single autochtonous squamous cell carcinoma resulting from 3-methylcholanthrene treatment reduced the growth rate of the primary tumors by 90%. In some animals tumor regression was observed. While all vehicle treated animals had died within the seven weeks, all of the aprotinin treatment group remained alive. Reduced tumor growth was associated with hyperkeratosis (Ohkoshi, Gann (1980), 71: 246–250).

Clinically, a surgically cured group of 26 patients who received aprotinin i.v. exhibited a 70% survival two years post surgery with no recurrence of tumors whereas a placebo group of 26 patients at the same time exhibited only a 38% survival with a significant rate of tumor recurrence (Freeman et al. Br. Soc. Gastroenterol. (1980) supplement A: 902). In a case study (Guthrie et al., Br. J. Clin. Pract (1981) 35: 330–332), administration of bromocriptine plus aprotinin to a patient with advanced cancer of the cervix caused remission. Aprotinin was administerd both as a 500,000 KIU i.p. bolus every eight hours concurrently with a continuous i.v. infusion of aprotinin at a rate of 200,000 KIU per 6 hr for a total of seven days once a month. Treatment was ended at the end of the fourth month due to the development of an allergic reaction to aprotinin. More recent evidence has further underscored a role of plasmin as a target for these effects of aprotinin on metastases.

The mechanism for these events could be related to the fact that aprotinin blocks the invasive potential of cancer cell lines (Liu G., et al., Int J. Cancer (1995), 60: 501–506). Furthermore, since the proteins of the instant invention are also potent inhibitors of plasmin and kallikrien, they are contemplated for use as anti-cancer agents. For example they are contemplated for use in blocking primary tumor growth by restricting neovascularization, primary tumor invasion and in blocking metastasis through inhibition of tissue infiltration. The compounds may be administered locally to tumors or systemically. In a preferred mode of treatment, the protein would be administered perioperatively during tumor debulking to minimize the risk of metastasis. In such a regime, the blood sparing properties of the compound would be additionally advantageous in providing a clearer surgical field of view. Another preferred mode of administration would be as a combination therapy with either MMP inhibitors or chemotherapy. An additional preferred mode of administration would be as a locally administered gene therapy designed to achieve selective expression of placental bikunin within the tumor cells, or their associated stroma and vascular beds.

Preferred types of cancers targeted for therapy would be vasular-dependent solid tumors such as breast, colon, lung, prostate and ovarian carcinomas which exhibit a high metastatic potential, and those for which local delivery of a high concentration of the protein is feasible such as lung cancers through pulmonary delivery, colon carcinomas through hepatic delivery to liver metastasis, or skin cancers such as head and neck carcinomas or melanomas through subcutaneous delivery. Since the proteins of the present invention are of human origin they would be less likely to be associated with allergic or anaphylactic reactions of the kind observed by Guthrie et al., supra, upon reuse.

Additionally, the proteins of the present invention are contemplated for use in the reduction of thromboembolic complications associated with activation of the intrinsic pathway of coagulation, This would include prevention of pulmonary embolism in late stage cancer patients, a frequent cause of death (Donati M B., (1994), Haemostasis 24:128–131).

Edema of the brain and spinal cord is a complication resulting from traumatic brain or spinal cord injury, stroke, cerebral ischemia, cerebral and sub-arachnoid hemhorrhage, surgery (including open heart surgery), infectious diseases such as encephalitis and meningitis, granulomatous diseases such as Sarcoid and focal or diffuse carcinomas, and is a contributor to the high level of morbidity and death following these events. Bradykinin is known to disrupt the blood brain barrier experimentally (Greenwood J., (1991), Neuroradiology, 33: 95–100; Whittle et al., (1992), Acta Neurochir., 115: 53–59), and infusion of bradykinin into the internal carotid artery induced brain edema in spontaneously hypertensive rats (SHR) subjected to common carotid artery occlusion (Kamiya, (1990), Nippon Ika Daigaku Zasshi. 57: 180–191). Elevated levels of bradykinin are found in extracellular fluids following trauma in a model involving traumatized rat spinal chord (Xu et al., (1991), J. Neurochem, 57: 975–980), and in plasma and tissue from rats with brain edema resulting from cerebral ischaemia (Kamiya et al., (1993), Stroke, 24: 571–575). Bradykinin is released from high molecular weight kininogen by serine proteases including kallikrein (Coleman (1984) J. Clin Invest., 73: 1249), and the serine protease inhibitor aprotinin was found to block the magnitude of brain edema resulting from cerebralschemia in SHR rats (Kamiya, (1990), Nippon Ika Daigaku Zasshi. 57: 180–191; Kamiya et al., (1993), Stroke, 24: 571–575) and rabbits subjected to a cold lesion of the brain (Unterberg et al., (1986), J. Neurosurgery, 64: 269–276).

These observations indicate that brain edema results from local proteolytic release of kinins such as bradykinin from high molecular weight kininogen, followed by bradykinin-induced increases in blood brain barrier permeability. Accordingly, placental bikunin and fragments thereof are contemplated as medicaments for the prevention of edema in patients at risk for this condition, particularly those of high risk of mortality or brain injury. This would include head and spinal trauma patients, polytrauma patients, patients undergoing surgery of the brain or spinal cord and their associated vessels or other generalsurgeries including open-heart surgery, patients who have suffered from a stroke, cerebral or sub-arachnoid hemorrhage, infectious diseases of the brain, granulomatous disease of the brain or diffuse or focal carcinomas and tumors of the brain or any conditions such as multiple sclerosis involving breakdown of the blood brain barrier or patients suffering from any other inflammatory processes of the brain or spinal cord. Patients would receive an administration of placental bikunin either as an infusion or bolus injection, intravenously or intracranially. Additional doses of placental bikunin could be administered intermittently over the following one to three weeks. Dose levels would be designed to attain circulating concentrations in excess of those required to neutralize elevations in plasma levels or bradykinin and other vasoactive peptides formed through the action of serine proteases, and sufficient to reduce edema. Since the protein is of human origin, repeated administration in this course of therapy would not lead to development of an immune reaction to the protein. Placental bikunin and fragments thereof would be contemplated for monotherapy or prophylacsis as well as for use in combination with other medicaments such as neurotherapeutics and neuroprotectants.

Recent evidence (Dela Cadena R. A. at al., (1995), FASEB J. 9: 446–452) has indicated that the contact activation pathway may contribute to the pathogenesis of arthritis and anemia, and that kallikrein inhibitors may be of therapeutic benefit. Accordingly, protease inhibitors of the present invention are contemplated according to their capacity to inhibit human kallikrein, as medicaments for the treatment of arthritis and anemia in humans.

Treatment of male non-insulin diabetic (NIDDM) patients with aprotinin significantly improved total glucose uptake and decreased the metabolic clearance rate of insulin (Laurenti et al., (1996), Diabetic Medicine 13: 642–645). Accordingly, the human proteins of the present invention are contemplated for chronic use as medicaments for the treatment of NIDDM.

Daily treatment of patients at risk of preterm delivery with urinary trypsin inhibitor for two weeks significantly reduced recurrent uterine contractions (Kanayama et al., (1996), Eur J. Obstet. Gynecol. & Reprod. Biol. 67: 133–138). Accordingly, the human proteins of the present invention are contemplated for use in the prevention of preterm delivery.

Aprotinin has been shown to stimulate differentiation of mouse myoblasts in culture (Wells and Strickland, Development, (1994), 120: 3639–3647)), a process that is inhibited by TGFb. TGFb exists as an inactive propolypeptide which is activated by limited proteolysis. The mechanism of aprotinin action has been proposed to involve inhibition of proteases which process pro-TGFb to the mature active form. TGFb has been shown to be up-regulated in various fibrotic lesions and has long thought to be a potential target for anti-fibrotic therapies. In a rat model of pulmonary fibrosis for example, TGF-b concentrations paralleled the extent of bleomycin-induced inflammation. Furthermore, plasmin levels in the alveolar macrophage coincided with mature TGF-b levels, and the addition of the plasmin inhibitor a-2-antiplasmin abrogated the post translational activation of pro-TGFb by the macrophage (Khal et al., (1996), Am. J. Respir. Cell Mol. Biol. 15: 252–259.) The data suggest that plasmin contributes to the formation of active TGFb by alveolar macrophage, and that this process plays a pathologic role in the bleomycin-induced lung inflammation.

In light of these observations, placental bikunin and fragments thereof are contemplated as therapeutics for various fibrotic disorders, including pulmonary, hepatic, renal and dermal (scleroderma) fibrosis.

Aerosilized aprotinin was shown to protect >50% of mice infected with lethal doses of either influenza virus or paramyxovirus (Ovcharenko and Zhirnov, Antiviral Research, (1994), 23: 107–118). A suppression of the development of fatal hemorrhagic bronchopneumonia and a normalization of body weight gain were also noted with aerosilized aprotinin treatment. In light of these observations, placental bikunin and fragments thereof are contemplated as therapeutics for various respiratory related influenza-like diseases.

The human placental bikunin, isolated domains, and other variants of the invention are contemplated for use in the medical/therapeutic applications suggested for native aprotinin or aprotinin analogues with other inhibitory profiles, in particular those which necessitate usage of large doses. These would include diseases for which use of the human protein is indicated by virtue of its ability to inhibit human serine proteases such as trypsin, plasmin, kallikrein, elastase, cathepsin G and proteinase-3, which include and are not limited to: acute pancreatitis (pancreatic elastase and trypsin), inflammation, thrombocytopenia, preservation of platelet function, organ preservation, wound healing, various forms of shock, including shock lung, endotoxin shock and post operative complications; disturbances of blood coagulation such as hyperfibrinolytic hemorrhage; acute and chronic inflammatory reactions, in particular for the therapy and prophylaxis of organ lesions, such as for example pancreatitis and radiation induced enteritis, complex-mediated inflammatory reactions such as immunovasculitis, glomerulonephritis and types of arthritis; collagenoses in particular rheumatoid arthritis; types of arthritis caused by metabolism-related deposits (for example gout); degeneration of the elastic constituents of the connective tissue parts of organs, such as in atherosclerosis (serum elastase) or pulmonary emphysema (neutrophil elastase); adult respiratory distress syndrome, inflammatory bowel disease, and psoriasis.

A major unexpected finding was that the synthetic peptides encoding bikunin (7–64), and bikunin (102–159), could properly fold into the correct three-dimensional conformation having active protease inhibitor bioactivity (Examples 2 and 1, respectively). Upon folding, each of these fragments of Bikunin underwent a reduction in mass of 6 mass units, consistent with the formation in each case, of three intrachain disulfide bonds between six cysteine residues of each fragment. Another surprising finding is that the synthetic peptides encoding bikunin (7–64), bikunin (102–159), and bikunin (1–170) are highly inhibitory of plasmin and both tissue and plasma kallikrein (Example 4, 3, and 10 respectively). Inhibition of plasmin and kallikrein by Trasylol® is thought to be involved in the mechanism by which Trasylol® reduces blood loss during open heart surgery. Our unexpected findings of the specificity of the Kunitz domains of the present invention make them suitable therapeutic agents for blood sparing during surgery or trauma where there is significant blood loss, or for any other condition where inhibition of plasmin and/or kallikrein would be beneficial.

Furthermore, we showed in this disclosure (Example 10) that placental bikunin (1–170) is a potent inhibitor of factor XIa and a moderate inhibitor of factor Xa. Factor XIa plays an essential role in the intrinsic pathway of coagulation, serving to interconvert inactive factor IX into active factor IXa. Thus, Placental Bikunin inhibits two key enzymes of the intrinsic pathway, kallikrein and factor XIa. Consistent with these observations, we also showed that placental bikunin (1–170) is a potent inhibitor of the activated partial thromboplastin time, which is a measure of the speed of coagulation driven by the intrinsic pathway. On the other hand, we showed that Placental bikunin (1–170) is an extremely weak inhibitor of the tissue factor VIIa complex, suggesting that it is not important in the regulation of the extrinsic coagulation cascade. Based on these unexpected findings, placental bikunin is contemplated as a medicament for diseases in which activation of the intrinsic pathway of coagulation contributes significantly to the disease mechanism. Examples of such diseases would include post-traumatic shock and disseminated intravascular coagulation.

A significant advantage of the Kunitz domains of the present invention is that they are human proteins, and also less positively charged than Trasylol® (Example 1), thereby reducing the risk of kidney damage on administration of large doses of the proteins. Being of human origin, the protein of the instant invention can thus be administered to human patients with significantly reduced risk of undesired immunological reactions as compared to administration of similar doses of Trasylol®. Furthermore, it was found that bikunin (102–159), bikunin (7–64), and bikunin (1–170) are significantly more potent inhibitors of plasma kallikrein than Trasylol® in vitro (Example 3, 4 and 10). Thus bikunin and fragments thereof are expected to be more effective in vivo at lowering blood loss in patients.

The amount of serine protease inhibitor administered should be sufficient to provide a supra normal plasma level. For the prophylactic reduction of bleeding during and following coronary aortic by-pass surgery (CABG), the proteins of the instant invention may be used in place of Trasylol® while taking into account the differences in potency. The use of Trasylol® is outlined in the Physicians Desk Reference, (1995), listing for Trasylol® supplement A. Briefly, with the patient in a supine position, the loading dose of placental bikunin, isolated domain or other variant is given slowly over about 20 to 30 minutes, after induction of anesthesia but prior to sternotomy. In general, a total dose of between about $2 \times 10^6$ KIU (kallikrein inhibitory, units) and $8 \times 10^6$ KIU will be used, depending on such factors as patient weight and the length of the surgery. Preferred loading doses are those that contain a total of 1 to 2 million kallikrein inhibitory units (KIU). When the loading dose is complete, it is followed by the constant infusion dose, which is continued until surgery is complete and the patient leaves the operating room. Preferred constant infusion doses are in the range of about 250,000 to 500,000 KIU per hour. The pump prime dose is added to the priming fluid of the cardiopulmonary bypass circuit, by replacement of an aliquot of the priming fluid prior to the institution of the cardiopulmonary bypass. Preferred pump prime doses are those that contain a total of about one to two million KIU.

The proteins of the instant invention are employed in pharmaceutical compositions formulated in the manner known to the art. Such compositions contain active ingredient(s) plus one or more pharmaceutically acceptable carriers, diluents, fillers, binders, and other excipients, depending on the administration mode and dosage form contemplated. Examples of therapeutically inert inorganic or organic carriers known to those skilled in the art include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like can also be added, as required to assist in the stabilization of the formulation or to assist in increasing bioavailability of the active ingredient(s) or to yield a formulation of acceptable flavor or odor in the case of oral dosing. The inhibitor employed in such compositions may be in the form of the original compound itself, or optionally, in the form of a pharmaceutically acceptable salt. The proteins of the instant invention can be adminstered alone, or in various combinations, and in combination with other therapeutic compositions. The compositions so formulated are selected as needed for administration of the inhibitor by any suitable mode known to those skilled in the art.

Parenteral administration modes include intravenous (i.v.), subcutaneous (s.c.), intraperitoneal (i.p.), and intramuscular (i.m.) routes. Intravenous administration can be used to obtain acute regulation of peak plasma concentrations of the drug as might be needed. Alternatively, the drug can be administered at a desired rate continuously by i.v. catheter. Suitable vehicles include sterile, non-pyrogenic aqueous diluents, such as sterile water for injection, sterile-buffered solutions or sterile saline. The resulting composition is administered to the patient prior to and/or during surgery by intravenous injection or infusion.

Improved half-life and targeting of the drug to phagosomes such as neutrophils and macrophage involved in inflammation may be aided by entrapment of the drug in liposomes. It should be possible to improve the selectivity of liposomal targeting by incorporating into the outside of the liposomes ligands that bind to macromolecules specific to target organs/tissues such as the GI tract and lungs. Alternatively, i.m. or s.c. deposit injection with or without encapsulation of the drug into degradable microspheres (e.g., comprising poly-DL-lactide-co-glycolide) or protective formulations containing collagen can be used to obtain prolonged sustained drug release. For improved convenience of the dosage form it is possible to use an i.p. implanted reservoir and septum such as the percuseal system. Improved convenience and patient compliance may also be achieved by use of either injector pens (e.g., the Novo Pin or Q-pen) or needle-free jet injectors (e.g., from Bioject, Mediject or Becton Dickinson). Precisely controlled release can also be achieved using implantable pumps with delivery to the desired site via a cannula. Examples include the subcutaneously implanted osmotic pumps available from ALZA such as the ALZET osmotic pump.

Nasal delivery may be achieved by incorporating the drug into bioadhesive particulate carriers (<200 mm) such as those comprising cellulose, polyacrylate or polycarbophil, in conjunction with suitable absorption enhancers such as phospholipids or acylcarnitines. Commercially available systems include those developed by Dan Biosys and Scios Nova.

Pulmonary delivery represents a nonparenteral mode of administration of the drug to the circulation. The lower airway epithelia are highly permeable to a wide range of proteins of molecular sizes up to about 20 kDa. Micron-sized dry powders containing the medicament in a suitable carrier such as mannitol, sucrose or lactose may be delivered to the distal alveolar surface using dry powder inhalers such as those of Inhale™, Dura™, Fisons (Spinhaler™), and Glaxo (Rotahaler™), or Astra (Turbohaler™) propellant based metered dose inhalers. Solution formulations with or without liposomes may be delivered using ultrasonic nebulizers.

Oral delivery may be achieved by incorporating the drug into tablets, coated tablets, dragees, hard and soft gelatin capsules, solutions, emulsions, suspensions or enteric coated capsules designed to release the drug into the colon where digestive protease activity is low. Examples of the latter include the OROS-CT/Osmet™ system of ALZA, and the PULSINCAP™ system of Scherer Drug Delivery Systems. Other systems use azo-crosslinked polymers that are degraded by colon-specific bacterial azoreductases, or pH sensitive polyacrylate polymers that are activated by the rise in pH in the colon. The above systems may be used in conjunction with a wide range of available absorption enhancers. Rectal delivery may be achieved by incorporating the drug into suppositories.

In its preferred medicinal application, for reduction of perioperative blood loss, the preferred mode of administration of the placental bikunin variants of the present invention is parenterally, preferably by i.v. route through a central line.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target protease such as plasmin or kallikrein which must be inhibited in order to treat the condition. As the active materials contemplated in this invention are deemed to be nontoxic, treatment preferably involves administration of an excess of the optimally required amount of active agent.

Additionally, placental bikunin, isolated domains or other variants may be used to isolate natural substances such as its cognate proteases from human material using affinity based separation methods, as well as to elicit antibodies to the protease that can be further used to explore the tissue distribution and useful functions of Placental bikunin.

Searching Human Sequence Data

The existence of a distinct human protein homologous in function to aprotinin, was deduced following a unique analysis of sequence entries to the expressed-sequence-tag data-base (hereafter termed dbEST) at the NCBI (National Center for Biological Information, Maryland). Using the TBlastN algorithm (BLAST, or Basic Local Alignment Search Tool uses the method of Altschul et a., (1990) J. Mol Biol 215: 403–410, to search for similarities between a query sequence and all the sequences in a data-base, protein or nucleic acid in any combination), the data-base was examined for nucleotide sequences bearing homology to the sequence of bovine pre-pro-aprotinin, Trasylol®. This search of numerous clones was selectively narrowed to two particular clones which could possibly encode for a deduced amino acid sequence that would correspond to a human protein homologous in function to aprotinin. The selected nucleic acid sequences were R35464 (SEQ ID NO: 12) and R74593 (SEQ ID NO: 14) that were generated from a human placental nucleic acid library. The translated protein sequence in the longest open reading frame for R35464 (SEQ ID NO: 13) was missing one of the 6 cysteines that are critical for formation of the Kunitz-domain covalent structure, meaning that the nucleic acid sequence of R35464 could not yield a functional inhibitor. Similarly, the longest translated open reading frame from clone R74593 (SEQ ID NO: 15) contained a stop codon 5' to the region encoding the Kunitz like sequence, meaning that this sequence, could not be translated to yield a functional secreted Kunitz domain. The significance of these sequences alone was unclear. It was possible that they represented a) the products of pseudogenes, b) regions of untranslated mRNA, or c) the products of viable mRNA which had been sequenced incorrectly.

Discovery of Human Bikunin

To specifically isolate and determine the actual human sequence, cDNA primers were designed to be capable of hybridizing to sequences located 5' and 3' to the segment of cDNA encoding our proposed Kunitz like sequences found within R35464 and R74593. The primers used to amplify a fragment encoding the Kunitz like sequence of R74593 were:

CGAAGCTTCATCTCCGAAGCTCCAGACG (the 3' primer with a HindIII site, SEQ ID NO:33) and AGGATCTAGACAATAATTACCTGACCAAGGA (the 5' primer with an XbaI site; SEQ ID NO:34).

These primers were used to amplify by PCR (30 cycles) a 500 base pair product from a human placental cDNA library from Clontech (MATCHMAKER, Cat #HL4003AB, Clontech Laboratories, Palo Alto, Calif.), which was subcloned into Bluescript-SK+ and sequenced with the T3 primer with a Sequenase™ kit version 2.0. Surprisingly, the sequence of the fragment obtained using our primers was different from the sequence listed in the dbEST data base for clone R74593. In particular, our new sequence contained an additional guanosine base inserted 3' to the putative stop codon, but 5' to the segment encoding the Kunitz-like sequence (FIGS. 3A–1 and 3A–2). The insertion of an additional G shifted the stop codon out of the reading frame for the Kunitz-like domain (G at base pair 114 of the corrected sequence for R74593; FIG. 3A–1).

Subsequent query of the dbEST for sequences homologous to the Kunitz-like peptide sequence of R74593 yielded H94519 derived from human retina library and N39798. These sequences contained a Kunitz-like sequence that was almost identical to the Kunitz-like domain encoded in R35464 except that it contained all six of the characteristic cysteines. Overlay of each of the nucleotide sequences with that of R74593 (corrected by the insertion of G at bp 114) and R68797 was used to obtain a consensus nucleotide sequence for a partial human placental bikunin (SEQ ID NO: 9; FIGS. 3A–1 and 3A–2). The translated consensus sequence yielded an open reading frame extending from residue −18 to +179 (FIGS. 3A–1 and 3A–2; full translation SEQ ID NO: 10) that contained two complete Kunitz-like domain sequences, within the region of amino acid residues 17–64 and 102–159 respectively.

Further efforts attempted to obtain additional 5' sequence by querying dbEST with the sequence of R35464. Possible matches from such searches, that possessed additional 5' sequence were then in turn used to re-query the dbEST. In such an iterative fashion, a series of overlapping 5' sequences were identified which included clones H16866, T66058, R34808, R87894, N40851 and N39876 (FIG. 4A). Alignment of some of these sequences suggested the presence of a 5' ATG. which might serve as a start site for synthesis of the consensus translated protein sequence. From this selected information, it was now possible to selectively screen for, and determine the nucleic acid and polypeptide sequences of a human protein with homologous function to aprotinin.

Figure 4B:
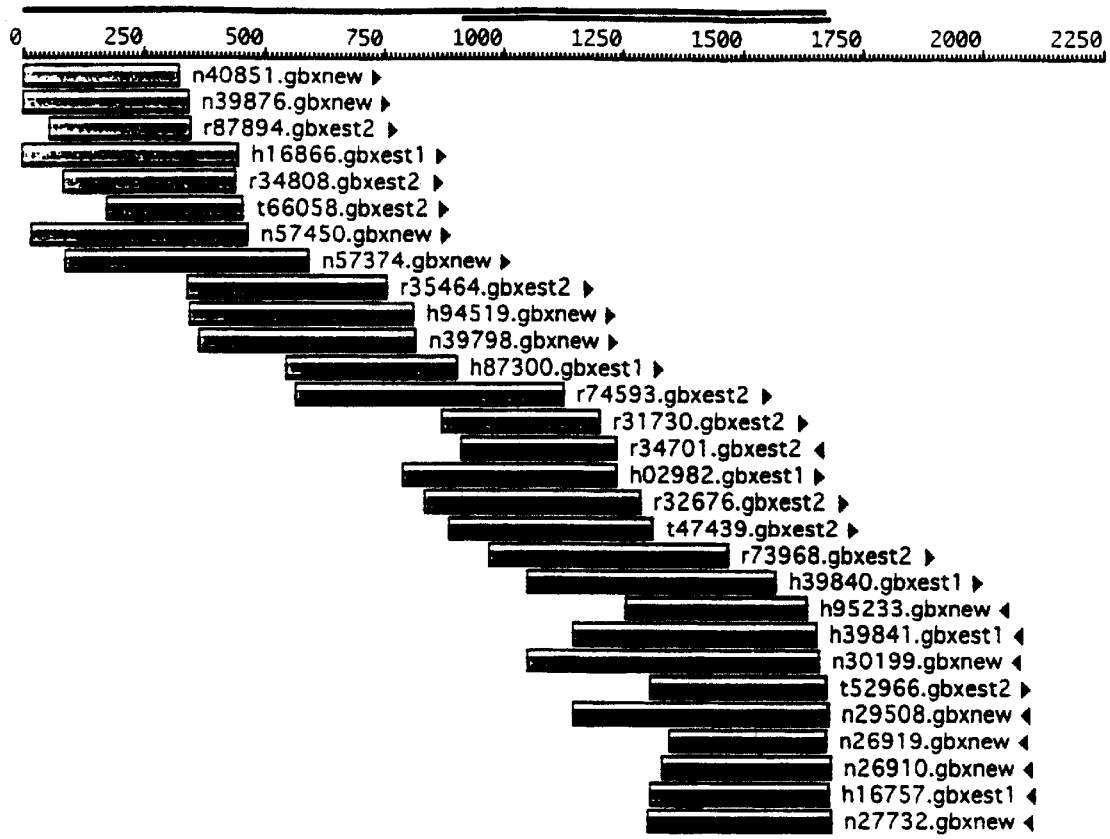
FIG. 4B depicts a subsequent more comprehensive EST overlay incorporating additional ESTs. Numbers on the upper X-axis refer to length in base pairs, starting at the first base from the most 5' EST sequence. The length of each bar is in proportion to the length in base pairs of the individual ESTs including gaps. The EST accession numbers are indicated to the right of their respective EST bars.
Figure 5:
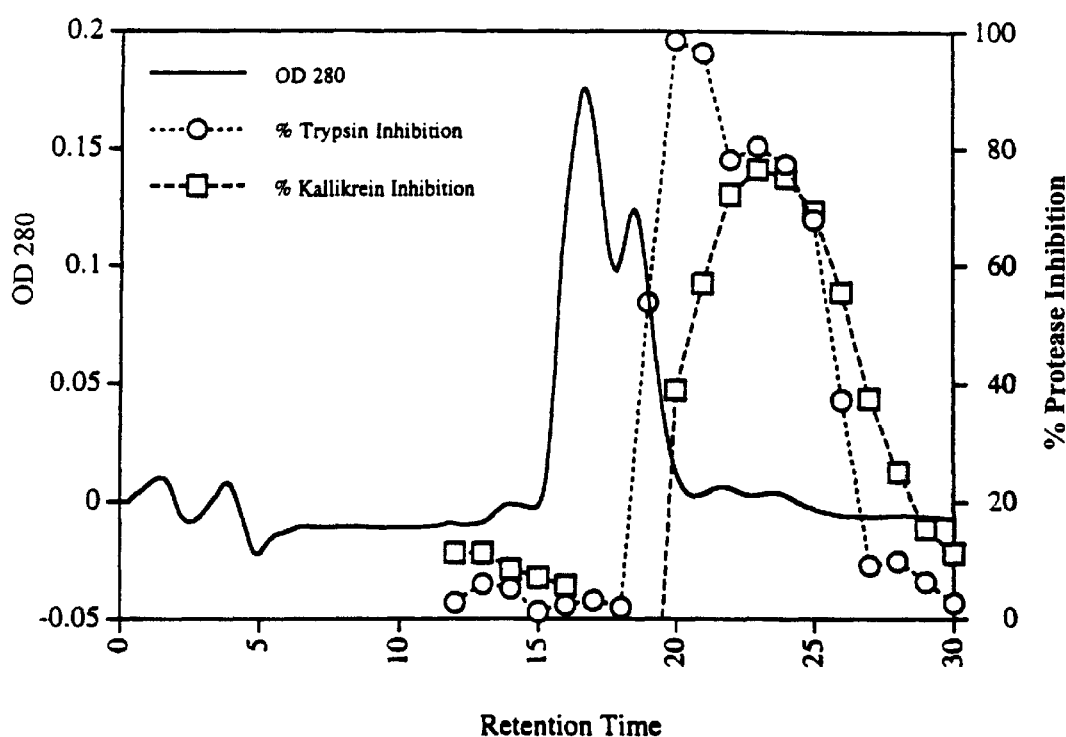

Re-interrogation of the dbEST revealed a number of new EST entries shown schematically in FIG. 4B. Overlap with these additional ESTs allowed us to construct a much longer consensus oligonucleotide sequence (FIGS. 4C–1—4C–20) that extended both 5' and 3' beyond the original oligonucleotide sequence depicted in FIGS. 3A–1—3A–2. In fact, the new sequence of total length 1.6 kilobases extended all the way to the 3' poly-A tail. The increased number of overlapping ESTs at each base-pair position along the sequence improved the level of confidence in certain regions such as the sequence overlapping with the 3' end of EST R74593 (FIGS. 3A–3B). Several overlapping ESTs in this region corroborated two critical base deletions relative to R74593 (located as bold underlined in FIGS. 4C–1—4C–20, map positions 994 and 1005). Translation of the new consensus sequence (FIG. 4D) in the bikunin encoding frame yielded a form of placental bikunin that was larger (248 amino acids) than the mature sequence (179 amino acids) encoded from the original consensus (SEQ ID NO: 1), and was terminated by an in-frame stop codon within the oligonucleotide consensus. The size increase was due to a frame shift in the 3' coding region resulting from removal of the two base insertions unique to EST R74593. The frame shift moved the stop codon of the original consensus (FIGS. 3A–3B) out of frame enabling read through into a new frame encoding the additional amino acid sequence. The new translation product (FIG. 4D) was identical to the original protein consensus sequence (SEQ ID NO: 1) between residues +1 to +175 (encoding the Kunitz domains), but contained a new C-terminal extension exhibiting a putative 24 residue long transmembrane domain (underlined in FIG. 4D) followed by a short 31 residue cytoplasmic domain. The precise sequence around the initiator methionine and signal peptide was somewhat tentative due to considerable heterogeneity amongst the overlapping ESTs in this region.

Analysis of the protein sequence by Geneworks™, highlighted asparagine residues at positions 30 and 67 as consensus sites for putative N-linked glycosylation. Asparagine 30 was not observed during N-terminal sequencing of the full length protein isolated from human placenta, consistent with it being glycosylated.

Cloning of Human Bikunin

The existence of a human mRNA corresponding to the putative human bikunin nucleotide sequence inferred from the analysis of FIGS. 3A–1—3A–2, was confirmed as follows. The nucleic acid primer hybridizing 5' to the Kunitz-encoding cDNA sequence of R35464 (b.p. 3–27 of consensus nucleotide sequence in FIG. 3A–1):
G G T C T A G A G G C C G G G T C G T T T C T C G C - CTGGCTGGGA
(a 5' primer derived from R35464 sequence with an XbaI site; SEQ ID NO: 35), and the nucleic acid primer hybridizing 3' to the Kunitz encoding sequence of R74593 (b.p. 680–700 of consensus nucleotide sequence in FIG. 3), was used to PCR amplify, from a Clontech human placental library, a fragment of the size (ca. 670 b.p) expected from a cDNA consensus nucleotide sequence encoding the placental bikunin sequence of FIGS. 3A–1—3A–2 (Shown schematically in FIG. 4A).

Using a 5' primer hybridizing to a sequence in R87894 that is 126 b.p 5' to the putative ATG start site discussed above, (shown schematically in FIG. 4A at b.p. 110) plus the same 3' primer to R74593 as used above, it was possible to amplify a fragment from a Clontech human placental library of the expected size (approximately 872 b.p) predicted by EST overlay (Shown schematically in FIG. 4).

Sequencing of the 872 b.p. fragment showed it to contain nucleotide segment corresponding to b.p. 110 to 218 of EST R87894 at its 5' end and b.p. 310 to 542 of the consensus sequence for placental bikunin inferred from the EST overlay analysis (of FIG. 3), at its 3' end. This 3' nucleotide sequence contained all of the Kunitz-like domain encoded by placental bikunin (102–159).

To obtain a cDNA encoding the entire extracellular region of the protein, the following 5' PCR primer:
CACCTGATCGCGAGACCCC (SEQ ID NO: 36)
designed to hybridize to a sequence within EST R34808 was used with the same 3' primer to EST 74593 to amplify (30 cycles) an approximately 780 base-pair cDNA product from the human placental cDNA library. This product was gel purified, and cloned into the TA vector (Invitrogen) for DNA sequencing by the dideoxy method (Sanger F., et al., (1977) Proc. Natl. Acad. Sci (USA), 74: 5463–5467) with the following primers:

```
Vector Specific:   GATTTAGGTGACACTATAG (SP6)(SEQ ID NO: 37)
                   TAATACGACTCACTATAGGG (T7)(SEQ ID NO: 38)

Gene Specific:     TTACCTGACCAAGGAGGAGTGC   (SEQ ID NO: 39)
                   AATCCGCTGCATTCCTGCTGGTG  (SEQ ID NO: 40)
                   CAGTCACTGGGCCTTGCCGT     (SEQ ID NO: 41)
```

The resulting cDNA sequence is depicted in FIG. 4E together with its translation product. At the nucleotide level, the sequence exhibited only minor differences from the consensus EST sequence (FIG. 4D). Translation of the sequence yielded a coding sequence containing an in-frame initiator ATG site, signal peptide and mature placental bikunin sequence and transmembrane domain. The translated sequence of the PCR product was missing the last 12 amino acid residues from the cytoplasmic domain as a consequence of the choice of selection of the 3' primer for PCR amplification. This choice of 3' PCR primer (designed based on the sequence of R74593) was also responsible for the introduction of an artifactual S to F mutation at amino acid position 211 of the translated PCR-derived sequence.

The signal peptide deduced from translation of the PCR fragment was somewhat different to that of the EST consensus.

To obtain a full length placental bikunin cDNA, the PCR derived product (FIG. 4E) was gel purified and used to isolate a non-PCR based full length clone representing the bikunin sequence. The PCR derived cDNA sequence was labeled with $^{32}$P-CTP by High Prime (Boehringer Mannheim) and used to probe a placental cDNA Library (Stratagene, Unizap™ λ library) using colony hybridization techniques. Approximately 2×10$^6$ phage plaques underwent 3 rounds of screening and plaque purification. Two clones were deemed full length (~1.5 kilobases) as determined by restriction enzyme analysis and based on comparison with the size of the EST consensus sequence (see above). Sequencing of one of these clone by the dideoxy method yielded the oligonucleotide sequence depicted in FIG. 4F. The translation product from this sequence yielded a protein with inframe initiator methionine, signal peptide and mature placental bikunin sequence. The mature placental bikunin sequence was identical to the sequence of the mature protein derived by translation of the EST consensus although the signal peptide sequence lengths and sequences differed. Unlike the PCR derived product, the cDNA derived by colony hybridization contained the entire ectodomain, transmembrane domain, cytoplasmic domain and in-frame stop codon. In fact, the clone extended all the way to the poly-A tail. The initiator methionine was followed by a hydrophobic signal peptide which was identical to the signal peptide encoded in the PCR derived clone. Subsequently we expressed and purified a soluble fragment of placental bikunin, bikunin (1–170), from Sf9 cells (Example 9), and found it to be a functional protease inhibitor (Example 10). Furthermore, we isolated from human placenta a soluble fragment of placental bikunin which was also an active protease inhibitor (Example 7). Both the natural protein and the form of the protein expressed in Sf9 cells are probably glycosylated at the asparagine residue at position 30 based on the recoveries of PTH-amino acids during N-terminal sequencing (Examples 7 and 9).

Based on the above observations, it seems that full length placental bikunin has the capacity to exist as a transmembrane protein on the surface of cells as well as a soluble protein. Other transmembrane proteins that contain Kunitz domains are known to undergo proteolytic processing to yield mixtures of soluble and membrane associated forms. These include two forms of the Amyloid Precursor Protein termed APP751 (Esch F., et al., (1990) Science, 248: 1122–1124) and APP 770 (Wang R., et al., (1991), J. Biol Chem, 266: 16960–16964).

Contact activation is a process which is activated by exposure of damaged vascular surfaces to components of the coagulation cascade. Angiogenesis is a process that involves local activation of plasmin at endothelial surfaces. The specificity of placental bikunin and its putative capacity to anchor to cell surfaces, suggest that the physiologic functions of transmembranous placental bikunin may include regulation of contact activation and angiogenesis.

The amino acid sequences for placental bikunin (7–64), bikunin (102–159), and full length placental bikunin (FIGS. 4F-1 and 4F-2) were searched against the PIR (Vers. 46.0) and PatchX (Vers. 46.0) protein databases as well as the GeneSeq (Vers. 20.0) protein database of patented sequences using the Genetics Computer Group program FastA. Using the Genetics Computer Group program TFastA (Pearson and Lipman, 1988, Proc. Natl. Acad. Sci. USA 85: 2444–2448), these same protein sequences were searched versus the six-frame translations of the GenBank (Vers. 92.0 with updates to Jan. 26, 1996) and EMBL (modified Vers. 45.0) nucleotide databases as well as the GeneSeq (Vers. 20.0) nucleotide database of patented sequences. The EST and STS subsets of GenBank and EMBL were not included in this set of searches. The best matches resulting from these searches contained sequences which were only about 50% identical over their full length to the 58-amino acid protein sequence derived from our analysis of clones R74593 and R35464.

Isolation of Human Bikunin

As mentioned above, synthetic peptides corresponding to bikunin (7–64) and bikunin (102–159) as determined from the translated consensus sequence for bikunin (FIGS. 3A-1 and 3A-2), could be refolded (Examples 2 and 1, respectively) to yield active kallikrein inhibitor protein (Example 4 and 3, respectively). We exploited this unexpected property to devise a purification scheme to isolate native placental bikunin from human tissue.

Using a purification scheme which employed kallikrein-sepharose affinity chromatography as a first step, highly purified native potent kallikrein inhibitor was isolated. The isolated native human bikunin had an identical N-terminus (sequenced for 50 amino acid residues) as the sequence predicted by the translation of the consensus nucleic acid sequence (FIGS. 3A-1 and 3A-2) amino acid residues +1 to +50 (Example 7). This confirmed for the first time the existence of a novel native kallikrein inhibitor isolated from human placenta.

Known Kunitz-like domains are listed below. Residues believed to be making contact with target proteases are highlighted as of special interest (bold/underlined). These particular residues are named positions Xaa$^{1-16}$ for specific reference as shown by label Xaa below:

```
Xaa                            1 1  111    1              1
  1         2   3 456789       0 1  234    5              6

1) IHDFCLVSKVV GRCRASMPRW WYNVTDGSCQ LFVYGGCDGN SNNYLTKEEC
LKKCATV

2) YEEYCTANAVT GPCRASFPRW YFDVERNSCN NFIYGGCRGM KNSYRSEEAC MLRC-
FRQ

3) -HSFCAFKADD GPCKAIMKRF FFNIFTRQCE EFIYGGCEGN QNRFESLEEC KKMC-
TRD

4) -PDFCFLEEDP GICRGYITRY FYNNQTKQCE RFKYGGCLGN MNNFETLEEC
KNICEDG
```

-continued

```
 5) -PSWCLTPADR GLCRANENRF YYNSVIGKCR PFKYSGCGGN ENNFTSKQEC
    LRACKKG

6) -AEICLLPLDY GPCRALLLRY YYRYRTQSCR QFLYGGCEGN ANNFYTWEAC
    DDACWRI

7) -PSFCYSPKDE GLCSANVTRY YFNPRYRTCD AFTYTGCGGN DNNFVSREDC KRA-
    CAKA

8) -KAVCSQEAMT GPCRAVMPRT TFDLSKGKCV RFITGGCOGN RNNFESEDYC
    MAVCKAM

9) RPDFCLEPPYT GPCKARIIRY FYNAKAGLCQ TFVYGGCRAK RNNFKSAEDC
    MRTCGGA

10) ----CQLGYSA GPCMGMTSRY FYNGTSMACE TFQYGGCMGN GNNFVTEKEC LQTC

11) VAACNLPIVR GPCRAFIQLW AFDAVKGKCV LFPYGGCQGN GNKFYSEKEC REY-
    CGVP

12) -EVCCSEQAET GPCRAMZSRW YFDVTEGKCA PFFYGGCGGN RNNFDTEEYC
    MAVCGSA

13) ----CKLPKDE GTCRDFILKW YYDPNTKSCA RFWYGGCGGN ENKFGSQKEC EKVC

14) -PNVCAFPMEK GPCQTYMTRW FFNFETGECE LFAYGGCGGN SNNFLRKEKC
    EKFCKFT
```

Where sequence number 1) is Bikunin (7–64) (SEQ ID NO: 4); sequence 2) is Bikunin (102–159) (SEQ ID NO: 6); sequence 3) is Tissue factor pathway inhibitor precursor 1 (SEQ ID NO: 18); sequence 4) is Tissue factor pathway inhibitor precursor 1 (SEQ ID NO: 19); sequence 5) is Tissue factor pathway inhibitor precursor (SEQ ID NO: 20); sequence 6) is Tissue factor pathway inhibitor precursor 2 (SEQ ID NO: 21); sequence 7) is Tissue factor pathway inhibitor precursor 2 (SEQ ID NO: 22); sequence 8) is Amyloid precursor protein homologue (SEQ ID NO: 23); sequence 9) is Aprotinin (SEQ ID NO: 24); sequence 10) is Inter-α-trypsin inhibitor precursor (SEQ ID NOs: 25); sequence 11) is Inter-α-trypsin inhibitor precursor (SEQ ID NOs: 26); sequence 12) is Amyloid precursor protein (SEQ ID NO: 27); sequence 13) is Collagen α-3(VI) precursor (SEQ ID NO: 28); and squence 14) is HKI-B9 (SEQ ID NO: 29).

It can be seen that Placental Bikunin (7–64) and (102–159) each have the same number (six) and spacing of cysteine residues as is found in members of the Kunitz class of serine protease inhibitors. The precise bonding of cysteine residues to form the three intrachain disulfide bonds is known and invarient for all previously known Kunitz family members (Laskowski, M et al., 1980, Ann. Rev. Biochem. 49:593–626). Based on this known bonding pattern and the fact that the folding of Placental Bikunin (7–64) and (102–159) into active protease inhibitors is accompanied by a mass reduction consistent with the formation of three intrachain disulfide bonds (Examples 2 and 1), it is highly probable that the disulfide bonding within the Kunitz domains of Placental Bikunin occur between cysteine residues: C11 and C61; C20 and C44; C36 and C57; C106 and C156; C115 and C139; C131 and C152. Furthermore, this pattern of disulfide bonding is highly probable in larger forms of Placental Bikunin containing both Kunitz domains since such forms of the protein are also active serine protease inhibitors and because N-terminal sequencing (Example 7) of native Placental Bikunin for 50 cycles yielded a sequence that was silent at positions where the cysteine residues were expected.

The placental bikunin, isolated domains or other variants of the present invention may be produced by standard solid phase peptide synthesis using either t-Boc chemistry as described by Merrifield R. B. and Barany G., in: The peptides, Analysis, Synthesis, Biology, 2, Gross E. et al., Eds. Academic Press (1980) Chapter 1; or using F-moc chemistry as described by Carpino L. A., and Han G. Y., (1970) J. Amer Chem Soc., 92, 5748–5749, and illustrated in Example 2. Alternatively, expression of a DNA encoding the placental bikunin variant may be used to produce recombinant placental bikunin variants.

The invention also relates to DNA constructs that encode the Placental bikunin protein variants of the present invention. These constructs may be prepared by synthetic methods such as those described in Beaucage S. L. and Caruthers M. H., (1981) Tetrahedron Lett, 22, pp1859–1862; Matteucci M. D and Caruthers M. H., (1981), J. Am. Chem. Soc. 103, p 3185; or from genomic or cDNA which may have been obtained by screening genomic or cDNA libraries with cDNA probes designed to hybridize with placental bikunin encoding DNA sequence. Genomic or cDNA sequence can be modified at one or more sites to obtain cDNA encoding any of the amino acid substitutions or deletions described in this disclosure.

The instant invention also relates to expression vectors containing the DNA constructs encoding the placental bikunin, isolated domains or other variants of the present invention that can be used for the production of recombinant placental bikunin variants. The cDNA should be connected to a suitable promoter sequence which shows transcriptional activity in the host cell of choice, possess a suitable terminator and a poly-adenylation signal. The cDNA encoding the placental bikunin variant can be fused to a 5' signal peptide that will result in the protein encoded by the cDNA to undergo secretion. The signal peptide can be one that is recognized by the host organism. In the case of a mammalian host cell, the signal peptide can also be the natural signal peptide present in full length placental bikunin. The procedures used to prepare such vectors for expression of placental bikunin variants are well known in the art and are for example described in Sambrook et al., Molecular Cloning: A laboratory Manual, Cold Spring Harbor, N.Y., (1989).

The instant invention also relates to transformed cells containing the DNA constructs encoding the placental bikunin, isolated domains or other variants of the present invention that can be used for the production of recombinant placental bikunin variants. A variety of combinations of expression vector and host organism exist which can be used for the production of the placental bikunin variants. Suitable host cells include baculovirus infected Sf9 insect cells, mammalian cells such as BHK, CHO, Hela and C-127, bacteria such as *E. coli,* and yeasts such as *Saccharomyces cervisiae.* Methods for the use of mammalian, insect and microbial expressions systems needed to achieve expression of placental bikunin are well known in the art and are described, for example, in Ausubel F. M et al., Current Protocols in Molecular Biology, John Wiley & Sons (1995), Chapter 16. For fragments of placental bikunin containing a single Kunitz inhibitor domain such as bikunin (7–64) and (102–159), yeast and *E. coli* expression systems are preferable, with yeast systems being most preferred. Typically, yeast expression would be carried out as described in U.S. Pat. No. 5,164,482 for aprotinin variants and adapted in Example 5 of the present specification for placental bikunin (102–159). *E.coli* expression could be carried out using the methods described in U.S. Pat. No. 5,032,573. Use of mammalian and yeast systems are most preferred for the expression of larger placental bikunin variants containing both inhibitor domains such as the variant bikunin (7–159).

DNA encoding variants of placental bikunin that possess amino acid substitution of the natural amino sequence can be prepared for expression of recombinant protein using the methods of Kunkel T. A., (1985) Proc. Natl. Acad. Sci USA 82: 488–492. Briefly, the DNA to be mutagenized is cloned into a single stranded bacteriophage vector such as M13. An oligonucleotide spanning the region to be changed and encoding the substitution is hybridized to the single stranded DNA and made double stranded by standard molecular biology techniques. This DNA is then transformed into an appropriate bacterial host and verified by dideoxynucleotide sequencing. The correct DNA is then cloned into the expression plasmid. Alternatively, the target DNA may be mutagenized by standard PCR techniques, sequenced, and inserted into the appropriate expression plasmid.

The following particular examples are offered by way of illustration, and not limitation, of certain aspects and preferred embodiments of the instant invention.

EXAMPLE 1

Preparation of Synthetic Placental Bikunin (102–159)

Materials and methods/Reagents used. The fluorogenic substrate Tos-Gly-Pro-Lys-AMC was purchased from Bachem BioScience Inc (King of Prussia, Pa.). PNGB, Pro-Phe-Arg-AMC, Ala-Ala-Pro-Met-AMC, bovine trypsin (type III), human plasma kallikrein, and human plasmin were from Sigma (St. Louis, Mo.).

Recombinant aprotinin (Trasylol®) was from Bayer AG (Wuppertal, Germany). Pre-loaded Gln Wang resin was from Novabiochem (La Jolla, Calif.). Thioanisole, ethanedithiol and t-butyl methyl ether was from Aldrich (Milwaukee, Wis.).

Quantification of Functional Placental Bikunin (7–64) and (102–159)

The amount of trypsin inhibitory activity present in the refolded sample at various stages of purification was measured using GPK-AMC as a substrate. Bovine trypsin (200 pmoles) was incubated for 5 min at 37% C with bikunin (7–64) or (102–159), from various stages of purification, in buffer A (50 mM Hepes, pH 7.5, 0.1 M NaCl, 2 mM $CaCl_2$ and 0.01% TRITON X-100®). GPK-AMC was added (20 $\mu$M final) and the amount of coumarin produced was determined by measuring the fluorescence (ex=370 nm, em=432 nm) on a Perkin-Elmer LS-50B fluorimeter over a 2 min. period. For samples being tested the % inhibition for each was calculated according to equation 1; where $R_0$ is the rate or fluorescence increase in the presence of inhibitor and $R_1$ is the rate determined in the absence of added sample. One unit of activity for the inhibitor is defined as the amount needed to achieve 50% inhibition in the assay using the conditions as described.

$$\% \text{ inhibition}=100\times[1-R_0/R_1] \qquad (1)$$

Synthesis. Placental bikunin (102–159) was synthesized on an Applied Biosystems model 420A peptide synthesizer using NMP-HBTU Fmoc chemistry. The peptide was synthesized on pre loaded Gln resin with an 8-fold excess of amino acid for each coupling. Cleavage and deprotection was performed in 84.6% trifluoroacetic acid (TFA), 4.4% thioanisole, 2.2% ethanedithiol, 4.4% liquified phenol, and 4.4% $H_2O$ for 2 hours at room temperature. The crude peptide was precipitated, centrifuged and washed twice in t-butyl methyl ether. The peptide was purified on a Dynamax 60A C18 reverse-phase HPLC column using a TFA/acetonitrile gradient. The final preparation (61.0 mg) yielded the correct amino acid composition and molecular mass by Electrospray mass spectroscopy (MH+=6836.1; calcd= 6835.5) for the predicted sequence:

YEEYCTANAV TGPCRASFPR WYFDVERNSC NNFIYGGCRG NKNSYRSEEA CMLRCFRQ (SEQ ID NO: 6)

Purification. Refolding of placental bikunin (102–159) was performed according to the method of Tam et al., (J. Am. Chem. Soc. 1991, 113: 6657–6). A portion of the purified peptide (15.2 mg) was dissolved in 4.0 ml of 0.1 M Tris, pH 6.0, and 8 M urea. Oxidation of the disulfides was accomplished by dropwise addition of a solution containing 23% DMSO, and 0.1 M Tris, pH 6.0 to obtain a final concentration of 0.5 mg/ml peptide in 20% DMSO, 0.1 M Tris, pH 6.0, and 1 M urea. The solution was allowed to stir for 24 hr at 25° C. after which it was diluted 1:10 in buffer containing 50 mM Tris, pH 8.0, and 0.1 M NaCl. The material was purified using a kallikrein affinity column made by covalently attaching 30 mg of bovine pancreatic kallikrein (Bayer AG) to 3.5 mls of CNBr activated Sepharose (Pharmacia) according to the manufacturers instructions. The refolded material was loaded onto the affinity column at a flow rate of 1 ml/min and washed with 50 mM Tris, pH 8.0, and 0.1 M NaCl until absorbance at 280 nm of the wash could no longer be detected. The column was eluted with 3 volumes each of 0.2 M acetic acid, pH 4.0 and 1.7. Active fractions were pooled (see below) and the pH of the solution adjusted to 2.5. The material was directly applied to a Vydac C18 reverse-phase column (5 micron, 0.46×25 cm) which had been equilibrated in 22.5% acetonitrile in 0.1% TFA. Separation was achieved using a linear gradient of 22.5 to 40% acetonitrile in 0.1% TFA at 1.0 ml/min over 40 min. Active fractions were pooled, lyophilized, redissolved in 0.1% TFA, and stored at −20° C. until needed.

Results. Synthetic placental bikunin (102–159) was refolded using 20% DMSO as the oxidizing agent as described above, and purified by a 2-step purification protocol as shown below, to yield an active trypsin inhibitor (Table 1 below).

TABLE 1

Purification table for the isolation of synthetic placental bikunin (102–159)

| Purification Step | Vol (ml) | mg/ml | mg | Units[c] (U) | SpA (U/mg) | Yield |
|---|---|---|---|---|---|---|
| 8.0 M Urea | 4.0 | 3.75[a] | 15.0 | 0 | 0 | — |
| 20% DMSO | 32.0 | 0.47[a] | 15.0 | 16,162 | 1,078 | 100 |
| Kallikrein affinity | 9.8 | 0.009[b] | 0.09 | 15,700 | 170,000 | 97 |
| C18 | 3.0 | 0.013[ab] | 0.04 | 11,964 | 300,000 | 74 |

[a]Protein determined by AAA.
[b]Protein determined by OD280 nm using the extinction coefficient determined for the purified protein ($1.7 \times 10^4$ Lmol$^{-1}$ cm$^{-1}$).
[c]One Unit is defined as the amount of material required to inhibit 50% of trypsin activity in a standard assay.

Chromatography of the crude refolded material over an immobilized bovine pancreatic kallikrein column selectively isolated 6.0% of the protein and 97% of the trypsin inhibitory activity present. Subsequent chromatography using C18 reverse-phase yielded a further purification of 2-fold, with an overall recovery of 74%o. On RPHPLC, the reduced and refolded placental bikunin (102–159), exhibited elution times of 26.3 and 20.1 minutes, respectively. Mass spectroscopy analysis of the purified material revealed a molecular mass of 6829.8; a loss of 6 mass units from the starting material. This demonstrates the complete formation of the 3 disulfides predicted from the peptide sequence.

The isoelectric points of the purified, refolded synthetic placental bikunin (102–159) was determined using a Multiphor II Electrophoresis System (Pharmacia) run according to the manufacturers suggestions, together with pI standards, using a precast Ampholine® PAGplate (pH 3.5 to 9.5) and focused for 1.5 hrs. After staining, the migration distance from the cathodic edge of the gel to the different protein bands was measured. The pI of each unknown was determined by using a standard curve generated by a plot of the migration distance of standards versus the corresponding pI's. With this technique, the pI of placental bikunin (102–159) was determined to be 8.3, in agreement with the value predicted from the amino acid sequence. This is lower than the value of 10.5 established for the pI of aprotinin. (Tenstad et al., 1994, Acta Physiol. Scand. 152: 33–50).

EXAMPLE 2

Preparation of Synthetic Placental Bikunin (7–64)

Placental bikunin (7–64) was synthesized, refolded and purified essentially as described for placental bikunin (102–159) but with the following modifications: during refolding, the synthetic peptide was stirred for 30 hr as a solution in 20% DMSO at 25° C.; purification by C18 RP-HPLC was achieved with a linear gradient of 25 to 45% acetonitrile in 0.1% TFA over 40 min (1 ml/min). Active fractions from the first C18 run were reapplied to the column and fractionated with a linear gradient (60 min, 1 ml/min) of 20 to 40% acetonitrile in 0.1% TFA.

Results. The final purified reduced peptide exhibited an MH+=6563, consistent with the sequence:
IHDFCLVSKV VGRCRASMPP WWYNVTDGSC QLFVYGGCDG NSNNYLTKEE CLKKCATV (SEQ ID NO: 4)

The refolding and purification yielded a functional Kunitz domain that was active as an inhibitor of trypsin (Table 2 below).

TABLE 2A

Purification table for the isolation of synthetic placental bikunin (7–64)

| Purification Step | Vol (ml) | mg/ml | mg | Units (U) | SpA (U/mg) | Yield |
|---|---|---|---|---|---|---|
| 8.0 M Urea | 8.0 | 2.5 | 20.0 | 0 | 0 | — |
| 20% DMSO | 64.0 | 0.31 | 20.0 | 68,699 | 3,435 | 100 |
| Kall affinity pH 4.0 | 11.7 | 0.10 | 1.16 | 43,333 | 36,110 | 62 |
| Kall affinity pH 1.7 | 9.0 | 0.64 | 5.8 | 4971 | 857 | 7.2 |
| C18-1 | 4.6 | 0.14 | 0.06 | 21,905 | 350,143 | 31.9 |
| C18-2 | 1.0 | 0.08 | 0.02 | 7,937 | 466,882 | 11.5 |

The purified refolded protein exhibited an MH+=6558, i.e. 5±1 mass units less than for the reduced peptide. This demonstrates that refolding caused the formation of at least one appropriate disulfide bond.

The pI of placental bikunin (7–64) was determined using the methods employed to determine the pI of placental bikunin (102–159). Placental bikunin (7–64) exhibited a pI that was much higher than the predicted value (pI=7.9). Refolded placental bikunin (7–64) migrated to the cathodic edge of the gel (pH 9.5) and an accurate pI could not be determined under these conditions.

Continued Preparation of Synthetic Placental Bikunin (7–64)

Because the synthetic placental bikunin (7–64) may not have undergone complete deprotection prior to purification and refolding, refolding was repeated using protein which was certain to be completely deprotected. Placental bikunin (7–64) was synthesized, refolded and purified essentially as described for placental bikunin (102–159) but with the following modifications: during refolding, the synthetic peptide (0.27 mg/ml) was stirred for 30 hr as a solution in 20% DMSO at 25 C; purification by C18 RP-HPLC was achieved with a linear gradient of 22.5 to 50% acetonitrile in 0.1% TFA over 40 min (1 ml/min).

Results. The final purified reduced peptide exhibited an MH+=6567.5, consistent with the sequence:
IHDFCLVSKV VGRCRASMPRW WYNVTDGSC QLFVYGGCDG NSNNYLTKEE CLKKCATV (SEQ ID NO: 4)

The refolding and purification yielded a functional Kunitz domain that was as active as an inhibitor of trypsin (Table 2B below).

TABLE 2B

Purification table for the isolation of synthetic placental bikunin (7–64)

| Purification Step | Vol (ml) | mg/ml | mg | Units (U) | SpA (U/mg) | Yield |
|---|---|---|---|---|---|---|
| 8.0 M Urea | 4.9 | 2.1 | 10.5 | 0 | 0 | — |
| 20% DMSO | 39.0 | 0.27 | 10.5 | 236,000 | 22,500 | 100 |
| Kallikrein Affinity (pH 2) | 14.5 | 0.3 | 0.43 | 120,000 | 279,070 | 50.9 |
| CIS Reverse-Phase | 0.2 | 1.2 | 0.24 | 70,676 | 294,483 | 30.0 |

The purified refolded protein exhibited an MH+=6561.2, i.e. 6.3 mass units less than for the reduced peptide. This demonstrates that refolding caused the formation of the expected three disulfide bonds.

The pI of refolded placental bikunin (7–64) was determined using the methods employed to determine the pI of placental bikunin (102–159). Refolded placental bikunin (7–64) exhibited a pI of 8.85, slightly higher than the predicted value (pI=7.9).

EXAMPLE 3
In Vitro Specificity of Functional Placental Bikunin Fragment (102–159)

Proteases. Bovine trypsin, human plasmin, and bovine pancreatic kallikrein quantitation was carried out by active site titration using p-nitrophenyl p'-guanidinobenzoate HCl as previously described (Chase,T., and Shaw, E., (1970) Methods Enzmol., 19: 20–27). Human kallikrein was quantitated by active site titration using bovine aprotinin as a standard and PFR-AMC as a substrate assuming a 1:1 complex formation. The $K_m$ for GPK-AMC with trypsin and plasmin under the conditions used for each enzyme was 29 $\mu$M and 726 $\mu$M, respectively; the $K_m$ for PFR-AMC with human plasma kallikrein and bovine pancreatic kallikrein was 457 $\mu$M and 81.5 $\mu$M, respectively; the $K_m$ for AAPR-AMC with elastase was 1600 $\mu$M. Human tissue kallikrein (Bayer, Germany) quantification was carried out by active site titration using p'nitrophenyl p'-guanidinobenzoate HCl as previously described (Chase, T., and Shaw, E., (1970) Methods Enzmol. 19: 20–27).

Inhibition Kinetics: The inhibition of trypsin by placental bikunin (102–159) or aprotinin was measured by the incubation of 50 pM trypsin with placental bikunin (102–159) (0–2 nM) or aprotinin (0–3 nM) in buffer A in a total volume of 1.0 ml. After 5 min. at 37° C., 15 $\mu$l of 2 mM GPK-AMC was added and the change in fluorescence (as above) was monitored. The inhibition of human plasmin by placental bikunin (102–159) and aprotinin was determined with plasmin (50 pM) and placental bikunin (102–159) (0–10 nM) or aprotinin (0–4 nM) in buffer containing 50 mM Tris-HCl (pH 7.5), 0.1 M NaCl, and 0.02% TRITON X-100®. After 5 min. incubation at 37° C., 25 $\mu$l of 20 mM GPK-AMC was added and the change in fluorescence monitored. The inhibition of human plasma kallikrein by placental bikunin (102–159) or aprotinin was determined using kallikrein (2.5 nM) and placental bikunin (102–159) (0–3 nM) or aprotinin (0–45 nM) in 50 mM Tris-HCl (pH 8.0), 50 mM NaCl, and 0.02% TRITON X-100®. After 5 min. at 37° C. 15 $\mu$l of 20 mM PFR-AMC was added and the change in fluorescence monitored. The inhibition of bovine pancreatic kallikrein by placental bikunin (102–159) and aprotinin was determined in a similar manner with kallikrein (92 pM), placental bikunin (102–159) (0–1.6 nM) and aprotinin (0–14 pM) and a final substrate concentration of 100 $\mu$M. The apparent inhibition constant $K_i^*$ was determined using the nonlinear regression data analysis program Enzfitter software (Biosoft, Cambridge, UK): The kinetic data from each experiment were analyzed in terms of the equation for a tight binding inhibitor:

$$V_i/V_o = 1 - (E_o + I_o + K_i^* - [(E_o + I_o + K_i^*)^2 - 4E_o I_o]^{1/2})/2E_o \quad (2)$$

where $V_i/V_o$ is the fractional enzyme activity (inhibited vs. uninhibited rate), and $E_o$ and $I_o$ are the total concentrations of enzyme and inhibitor, respectively. Ki values were obtained by correcting for the effect of substrate according to the equation:

$$K_i = K_i^*/(1 + [S_o]/K_m) \quad (3)$$

(Boudier, C., and Bieth, J. G., (1989) Biochim Biophys Acta., 995: 36–41)

For the inhibition of human neutrophil elastase by placental bikunin (102–159) and aprotinin, elastase (19 nM) was incubated with placental bikunin (102–159) (150 nM) or aprotinin (0–7.5 $\mu$M) in buffer containing 0.1 M Tris-HCl (pH 8.0), and 0.05% TRITON X-100®. After 5 min at 37% C, AAPM-AMC (500 $\mu$M or 1000 $\mu$M) was added and the fluorescence measured over a two-minute period. Ki values were determined from Dixon plots of the form 1/V versus [I] performed at two different substrate concentrations (Dixon et al., 1979).

The inhibition of human tissue kallikrein by aprotinin, placental bikunin fragment (7–64) or placental bikunin fragment (102–159) was measured by the incubation of 0.35 nM human tissue kallikrein with placental bikunin (7–64) (0–40 nM) or placental bikunin (102–159) (0–2.5 nM), or aprotinin (0–0.5 nM) in a 1 ml reaction volume containing 50 mM Tris-HCl buffer pH 9.0, 50 mM NaCl, and 0.1% TRITON X-100®. After 5 min. at 37° C., 5 ul of 2 mM PFR-AMC was added achieving 10 uM final and the change in fluorescence monitored. The Km for PFR-AMC with human tissue kallikrein under the conditions employed was 5.7 uM. The inhibition of human factor Xa (American Diagnostica, Inc, Greenwich, Conn.) by synthetic placental bikunin (102–159), recombinant placental bikunin, and aprotinin was measured by the incubation of 0.87 nM human factor Xa with increasing amounts of inhibitor in buffer containing 20 mM Tris (pH 7.5), 0.1 M NaCl, and 0.1% BSA. After 5 min. at 37° C., 30 ul of 20 mM LGR-AMC (Sigma) was added and the change in fluorescence monitored. The inhibition of human urokinase (Sigma) by Kunitz inhibitors was measured by the incubation of urokinase (2.7 ng) with inhibitor in a total volume of 1 ml buffer containing 50 mM Tris-HCl (pH 8.0), 50 mM NaCl, and 0.1% Triton X-100®. After 5 min. at 37° C., 35 ul of 20 mM GGR-AMC (Sigma) was added and the change in fluorescence monitored. The inhibition of Factor XIa (from Enzyme Research Labs, Southbend, Ind.) was measured by incubating FXIa (0.1 nM) with either 0 to 800 nM placental bikunin (7–64), 0 to 140 nM placental bikunin (102–159) or 0 to 40 uM aprotinin in buffer containing 50 mM Hepes pH 7.5, 100 mM NaCl, 2 mM CaCl2, 0.01% TRITON X-100®, and 1% BSA in a total volume of 1 ml. After 5 min at 37 C., 10 ul of 40 mM Boc-Glu(OBzl)-Ala-Arg-AMC (Bachem Biosciences, King of Prussia, Pa.) was added and the change in fluorescence monitored.

Results: A direct comparison of the inhibition profiles of placental bikunin (102–159) and aprotinin was made by measuring their inhibition constants with various proteases under identical conditions. The $K_i$ values are listed in Table 3 below.

TABLE 3

Ki values for the inhibition of various proteases by bikunin (102–159)

| Protease (concentration) | bikunin (102–159) Ki (nM) | Aprotinin Ki (nM) | Substrate (concentration) | Km (mM) |
|---|---|---|---|---|
| Trypsin (48.5 pM) | 0.4 | 0.8 | GPK-AMC (0.03 mM) | 0.022 |
| Chymotrypsin (5 nM) | 0.24 | 0.86 | AAPF-pNA (0.08 mM) | 0.027 |
| Bovine Pancreatic Kallikrein (92.0 pM) | 0.4 | 0.02 | PFR-AMC (0.1 mM) | 0.08 |
| Human Plasma Kallikrein (2.5 nM) | 0.3 | 19.0 | PFR-AMC (0.3 mM) | 0.46 |
| Human Plasmin (50 pM) | 1.8 | 1.3 | GPK-AMC (0.5 mM) | 0.73 |
| Human Neutrophil Elastase (19 nM) | 323.0 | 8500.0 | AAPM-AMC (1.0 $\mu$M) | 1.6 |
| Factor XIIa | >300.0 | 12,000.0 | PFR-AMC (0.2 $\mu$M) | 0.35 |

TABLE 3-continued

Ki values for the inhibition of various proteases by bikunin (102–159)

| Protease (concentration) | bikunin (102–159) Ki (nM) | Aprotinin Ki (nM) | Substrate (concentration) | Km (mM) |
|---|---|---|---|---|
| Human Tissue Kallikrein (0.35 nM) | 0.13 | 0.004 | PFR-AMC (10 μM) | 0.0057 |
| factor Xa (0.87 nM) | 274 | N.I. at 3 μM | LGR-AMC (0.6 mM) | N.D. |
| urokinase | 11000 | 4500 | GGR-AMC (0.7 mM) | N.D. |
| factor XIa (0.1 nM) | 15 | 288 | E(OBz)AR-AMC (0.4 mM) | 0.46 |

Placental bikunin (102–159) and aprotinin inhibit bovine trypsin and human plasmin to a comparable extent under the conditions employed. Aprotinin inhibited elastase with a Ki of 8.5 μM. Placental bikunin (102–159) inhibited elastase with a Ki of 323 nM. The $K_i$ value for the placental bikunin (102–159) inhibition of bovine pancreatic kallikrein was 20-fold higher than that of aprotinin inhibition. In contrast, placental bikunin (102–159) is a more potent inhibitor of human plasma kallikrein than aprotinin and binds with a 56-fold higher affinity.

Because placental bikunin (102–159) is greater than 50 times more potent than Trasylol® as an inhibitor of kallikrein, smaller amounts of human placental bikunin, or fragments thereof (i.e. placental bikunin (102–159)) are needed than Trasylol® in order to maintain the effective patient doses of inhibitor in KIU. This reduces the cost per dose of the drug and reduces the likelihood of adverse nephrotoxic effects upon re-exposure of the medicament to patients. Furthermore, the protein is human derived, and thus much less immunogenic in man than aprotinin which is derived from cows. This results in significant reductions in the risk of incurring adverse immunologic events upon re-exposure of the medicament to patients.

EXAMPLE 4

In vitro Specificity of Functional Placental Bikunin Fragment (7–64)

In vitro specificity of functional human placental bikunin (7–64) was determined using the materials and methods as described in the Examples above.

Results: The table below shows the efficacy of placental bikunin (7–64) as an inhibitor of various serine proteases in vitro. Data is shown compared against data obtained for screening inhibition using either placental bikunin (102–159), or aprotihin (Trasylol®).

TABLE 4 A

Ki values for the inhibition of various proteases by bikunin(7–64)

| Protease (concentration) | bikunin(7–64) Ki (nM) | Aprotinin Ki (nM) | bikunin (102–159) Ki (nM) |
|---|---|---|---|
| Trypsin (48.5 pM) | 0.17 | 0.8 | 0.4 |
| Bovine Pancreatic Kallikrein (92.0 pM) | 0.4 | 0.02 | 0.4 |
| Human Plasma Kallikrein (2.5 nM) | 2.4 | 19.0 | 0.3 |
| Human Plasmin (50 pM) | 3.1 | 13 | 1.8 |

TABLE 4 A-continued

Ki values for the inhibition of various proteases by bikunin(7–64)

| Protease (concentration) | bikunin(7–64) Ki (nM) | Aprotinin Ki (nM) | bikunin (102–159) Ki (nM) |
|---|---|---|---|
| Bovine chymotrypsin (5 nM) | 0.6 | 0.9 | 0.2 |
| Factor XIIa | >300 | 12000 | >300 |
| elastase | >100 | 8500 | 323 |

The results show that the amino acid sequence encoding placental bikunin (7–64) can be refolded to obtain an active serine protease inhibitor that is effective against at least four trypsin-like serine proteases.

Table 4B below also shows the efficacy of refolded placental bikunin (7–64) as an inhibitor of various serine proteases in vitro. Refolded placental bikunin (7–64) was prepared from protein that was certain to be completely deprotected prior to purification and refolding. Data is shown compared against data obtained for screening inhibition using either placental bikunin (102–159), or aprotinin (Trasylol®).

TABLE 4B

Ki values for the inhibition of various proteases by refolded bikunin (7–64)

| Protease (concentration) | bikunin (7–64) Ki (nM) | Aprotinin Ki (nM) | bikunin (102–159) Ki (nM) |
|---|---|---|---|
| Trypsin (50 pM) | 0.2 | 0.8 | 0.3 |
| Human Plasma Kallikrein (0.2 nM) | 0.7 | 19.0 | 0.7 |
| Human Plasma (50 pM) | 3.7 | 1.3 | 1.8 |
| Factor XIIa | not done | 12,000 | 4,500 |
| Factor XIa (0.1 nM) | 200 | 288 | 15 |
| Human Tissue Kallikrein | 2.3 | 0.004 | 0.13 |

Suprisingly, placental bikunin (7–64) was more potent than aprotinin at inhibiting human plasma kallikrein, and at least similar in efficacy as a plasmin inhibitor. These data show that placental bikunin (7–64) is at least as effective as aprotinin, using in vitro assays, and that one would expect better or similar potency in vivo.

EXAMPLE 5

Expression of Placental Bikunin Variant (102–159) in Yeast

The DNA sequence encoding placental bikunin 102–159 (SEQ ID NO: 6) was generated using synthetic oligonucleotides. The final DNA product consisted (5' to 3') of 15 nucleotides from the yeast α-mating factor propeptide sequence fused to the in-frame cDNA sequence encoding placental bikunin (102–159), followed by an in-frame stop codon. Upon cloning into a yeast expression vector pS604, the cDNA would direct the expression of a fusion protein comprising an N-terminal yeast α-mating factor propeptide fused to the 58 amino acid sequence of placental bikunin (102–159). Processing of this fusion protein at a KEX-2 cleavage site at the junction between the α-mating factor and Kunitz domain was designed to liberate the Kunitz domain at its native N-terminus.

A 5' sense oligonucleotide of the following sequence and containing a HindIII site for cloning was synthesized:

(SEQ ID NO: 42)
GAA GGG GTA AGC TTG GAT AAA AGA TAT GAA GAA TAC

TGC ACC GCC AAC GCA GTC ACT GGG CCT TGC CGT GCA

TCC TTC CCA CGC TGG TAC TTT GAC GTG GAG AGG

A 3' antisense oligonucleotide of the following sequence and containing both a BamHI site for cloning and a stop codon was synthesized:

(SEQ ID NO: 43)
CGC GGA TCC CTA CTG GCG GAA GCA GCG GAG CAT GCA

GGC CTC CTC AGA GCG GTA GCT GTT CTT ATT GCC CCG

GCA GCC TCC ATA GAT GAA GTT ATT GCA GGA GTT CCT

CTC CAC GTC AAA GTA CCA GCG

The oligonucleotides were dissolved in 10 mM Tris buffer pH 8.0 containing 1 mM EDTA, and 12 ug of each oligo were added combined and brought to 0.25M NaCl. To hybridize, the oligonucleotides were denatured by boiling for 5 minutes and allowed to cool from 65° C. to room temp over 2 hrs. Overlaps were extended using the Klenow fragment and digested with HindIII and BamHI. The resulting digested double stranded fragment was cloned into pUC19 and sequence confirmed. A clone containing the fragment of the correct sequence was digested with BamHI/HindIII to liberate the bikunin containing fragment with the following + strand sequence:

(SEQ ID NO: 44)
GAA GGG GTA AGC TTG GAT AAA AGA TAT GAA GAA TAC

TGC ACC GCC AAC GCA GTC ACT GGG CCT TGC CGT GCA

TCC TTC CCA CGC TGG TAC TTT GAC GTG QAG AGG AAC

TCC TGC AAT AAC TTC ATC TAT GGA GGC TGC CGG GGC

AAT AAG AAC AGC TAC CGC TCT GAG GAG GCC TGC ATG

CTC CGC TGC TTC CGC CAG TAG GGA TCC which was then gel purified and ligated into BamHI/HindIII cut pS604. The ligation mixture was extracted into phenol/chloroform and purified over a S-200 minispin column. The ligation product was directed transformed into yeast strains SC101 and WHL341 and plated on ura selection plates. Twelve colonies from each strain were re-streaked on ura drop out plates. A single colony was inoculated into 2 ml of ura DO media and grown over night at 30° C. Cells were pelleted for 2 minutes at 14000×g and the supernatants evaluated for their content of placental bikunin (102–159). Detection of Expression of Placental Bikunin (102–159) in Transformed Yeast Firstly, the supernatants (50 ul per assay) were evaluated for their capacity to inhibit the in vitro activity of trypsin using the assay methods as described in Example 1 (1 ml assay volume). An un-used media only sample as well as a yeast clone expressing an inactive variant of aprotinin served as negative controls. A yeast clone expressing natural aprotinin served as a positive control and is shown for comparison.

The second method to quantify placental bikunin (102–159) expression exploited use of polyclonal antibodies (pAbs) against the synthetic peptide to monitor the accumulation of the recombinant peptide using Western blots. These studies were performed only with recombinants derived from strain SC101, since these produced greater inhibitory activity than recombinants derived from strain WHL341.

To produce the pAb, two 6–8 week old New Zealand White female rabbits (Hazelton Research Labs, Denver, Pa.) were immunized on day zero with 250 ug of purified reduced synthetic placental bikunin (102–159), in Complete Freund's adjuvant, followed by boosts on days 14, 35 and 56 and 77 each with 125 ug of the same antigen in Incomplete Freund's adjuvant. Antiserum used in the present studies was collected after the third boost by established procedures. Polyclonal antibodies were purified from the antiserum over protein A.

Colonies 2.4 and 2.5 from transformation of yeast SC101 (FIG. 8) as well as an aprotinin control were grown overnight in 50 ml of ura DO media at 30° C. Cells were pelleted and the supernatant concentrated 100-fold using a Centriprep 3 (Amicon, Beverly, Mass.) concentrator. Samples of each (30 μl) were subjected to SDS-PAGE on 10–20% tricine buffered gels (Novex, San Diego, Calif.) using the manufacturers procedures. Duplicate gels were either developed with a silver stain kit (Integrated Separation Systems, Nantick, Mass.) or transferred to nitrocellulose and developed with the purified polyclonal antibody elicited to synthetic bikunin (102–159). Alkaline-phosphatase conjugated goat anti-rabbit antibody was used as the secondary antibody according to the manufacturer's directions (Kirkegaard and Perry, Gaithersburg, Md.).

Purification of Placental Bikunin (102–159) from a Transformed Strain of SC101

Fermentation broth from a 1 L culture of SC101 strain 2.4 was harvested by centrifugation (4,000 g×30 min.) then applied to a 1.0 ml column of anhydrochymotrypsin-sepharose (Takara Biochemical Inc., CA), that was previously equilibrated with 50 mM Hepes buffer pH 7.5 containing 0.1M NaCl, 2 mM $CaCl_2$ and 0.01% (v/v) TRITON X-100®. The column was washed with the same buffer but containing 1.0 M NaCl until the A280nm declined to zero, whereupon the column was eluted with 0.1M formic acid pH 2.5. Eluted fractions were pooled and applied to a C18 column (Vydac, 5um, 4.6×250 mm) previously equilibrated with 0.1% TFA, and eluted with a 50 min. linear gradient of 20 to 80% acetonitrile in 0.1% TFA. Fractions containing placental bikunin (102–159) were pooled and re-chromatographed on C18 employing elution with a linear 22.5 to 50% acetonitrile gradient in 0.1% TFA.

Figure 8A:
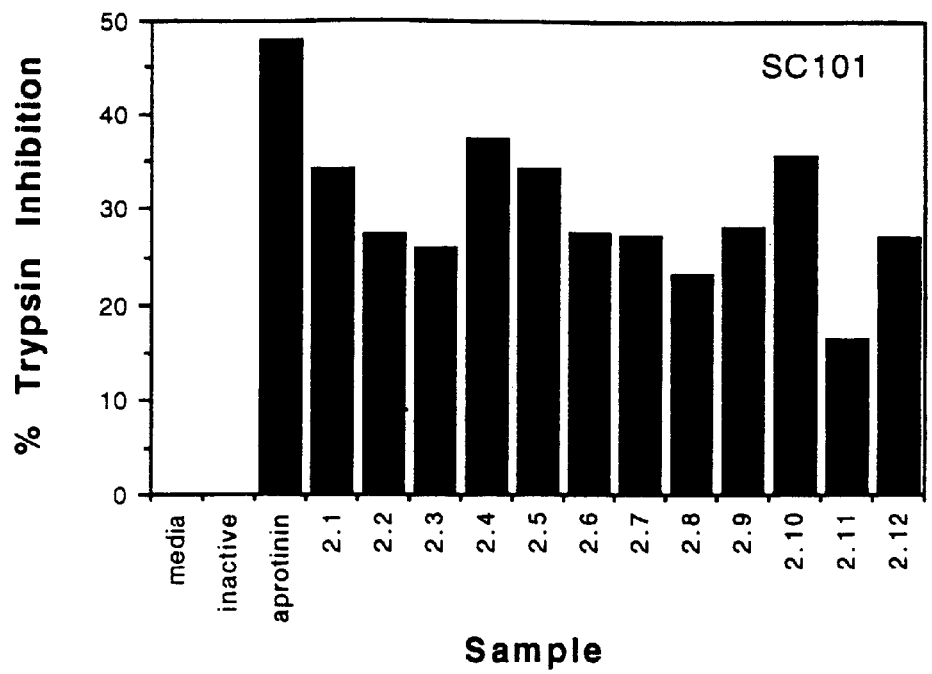
FIGS. 8A and 8B show the amount of trypsin inhibitory activity present in the cell-free fermentation broth from the growth of yeast strains SC101 (panel 8A) or WHL341 (panel 8B) that were stably transformed with a plasmid (pS604) that directs the expression of placental bikunin (102–159).
Figure 8B:
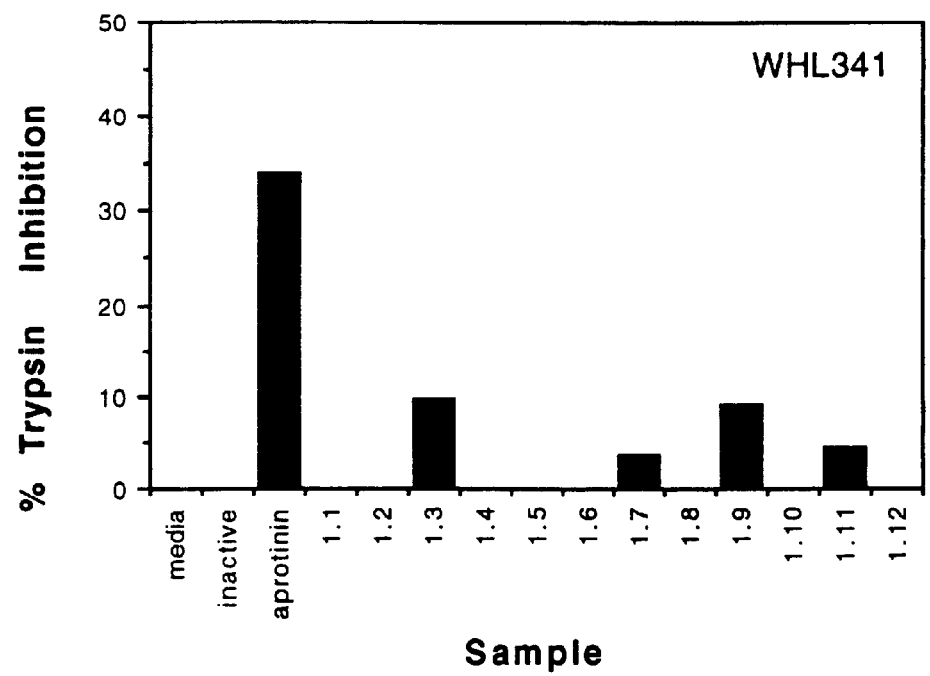
Figure 9:
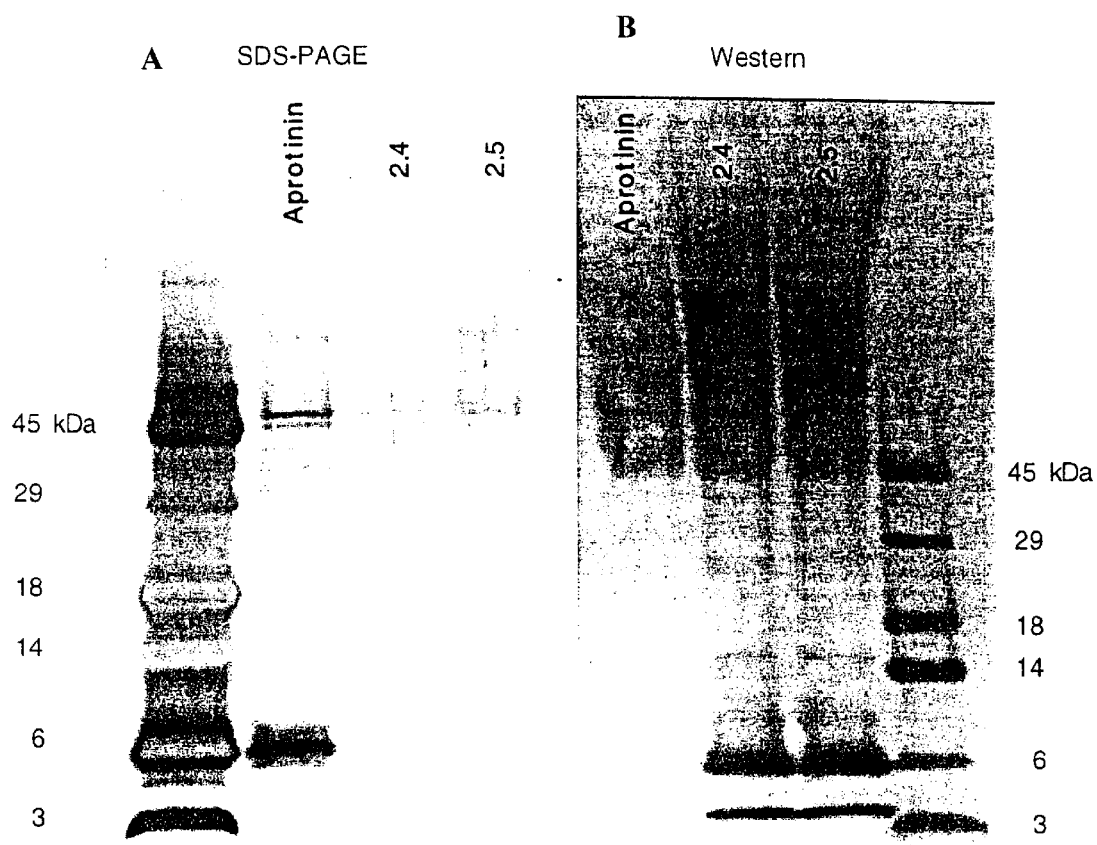

Results. FIG. 8 shows the percent trypsin activity inhibited by twelve colonies derived from the transformation of each of strains SC101 and WHL341. The results show that all twelve colonies of yeast strain SC101 transformed with the trypsin inhibitor placental bikunin (102–159) had the ability to produce a substantial amount of trypsin inhibitory activity compared to the negative controls both of which showed no ability to inhibit trypsin. The activity is therefore related to the expression of a specific inhibitor in the placental bikunin variant (102–159) transformed cells. The yeast WHL341 samples contained minimal trypsin inhibitory activity. This may be correlated to the slow growth observed with this strain under the conditions employed.

FIGS. 9A and 9B show the SDS-PAGE and western analysis of the yeast SC101 supernatants. Silver stained SDS-PAGE of supernatants derived from recombinant yeasts 2.4 and 2.5 expressing placental bikunin (102–159) as well as from the yeast expressing aprotinin yielded a protein band running at approximated 6 kDa, corresponding to the size expected for each recombinant Kunitz inhibitor domain. Western analysis showed that the 6 kDa bands expressed by stains 2.4. and 2.5 reacted with the pAb elicited to placental bikunin (102–159). The same 6 kDa band in the aprotinin control did not react with the same antibody, demonstrating the specificity of the antibody for the placental bikunin variant (102–159).

Figure 10:
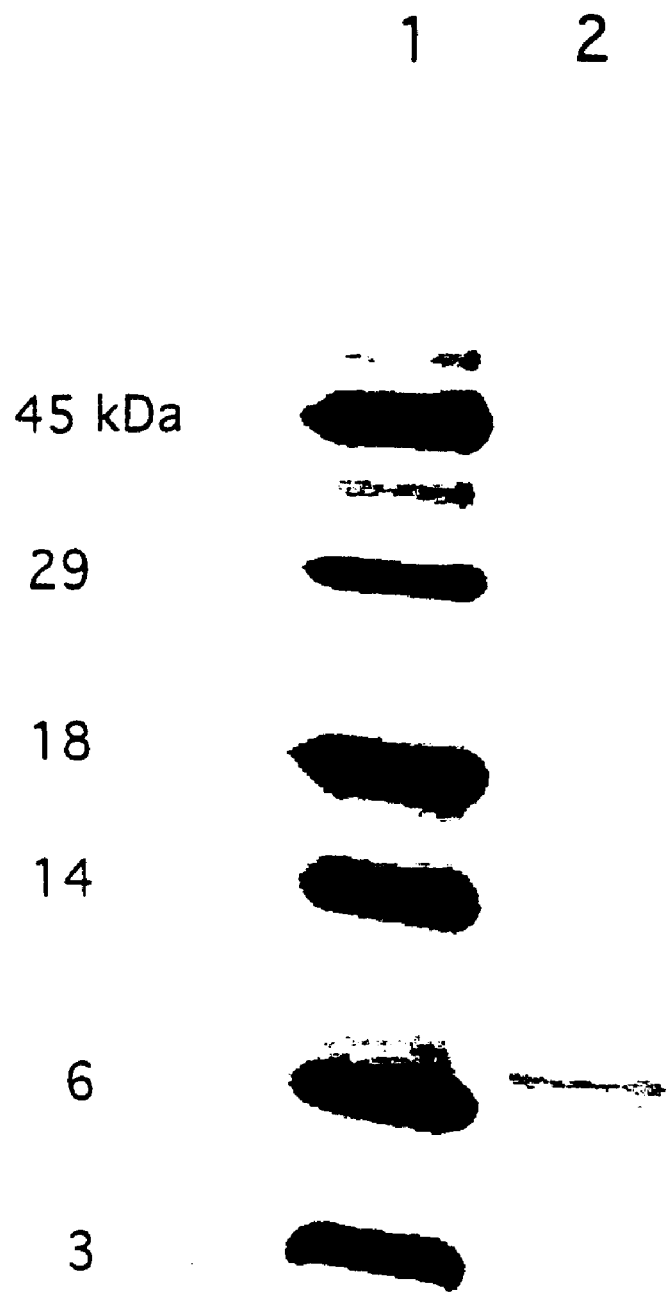
Figure 11:
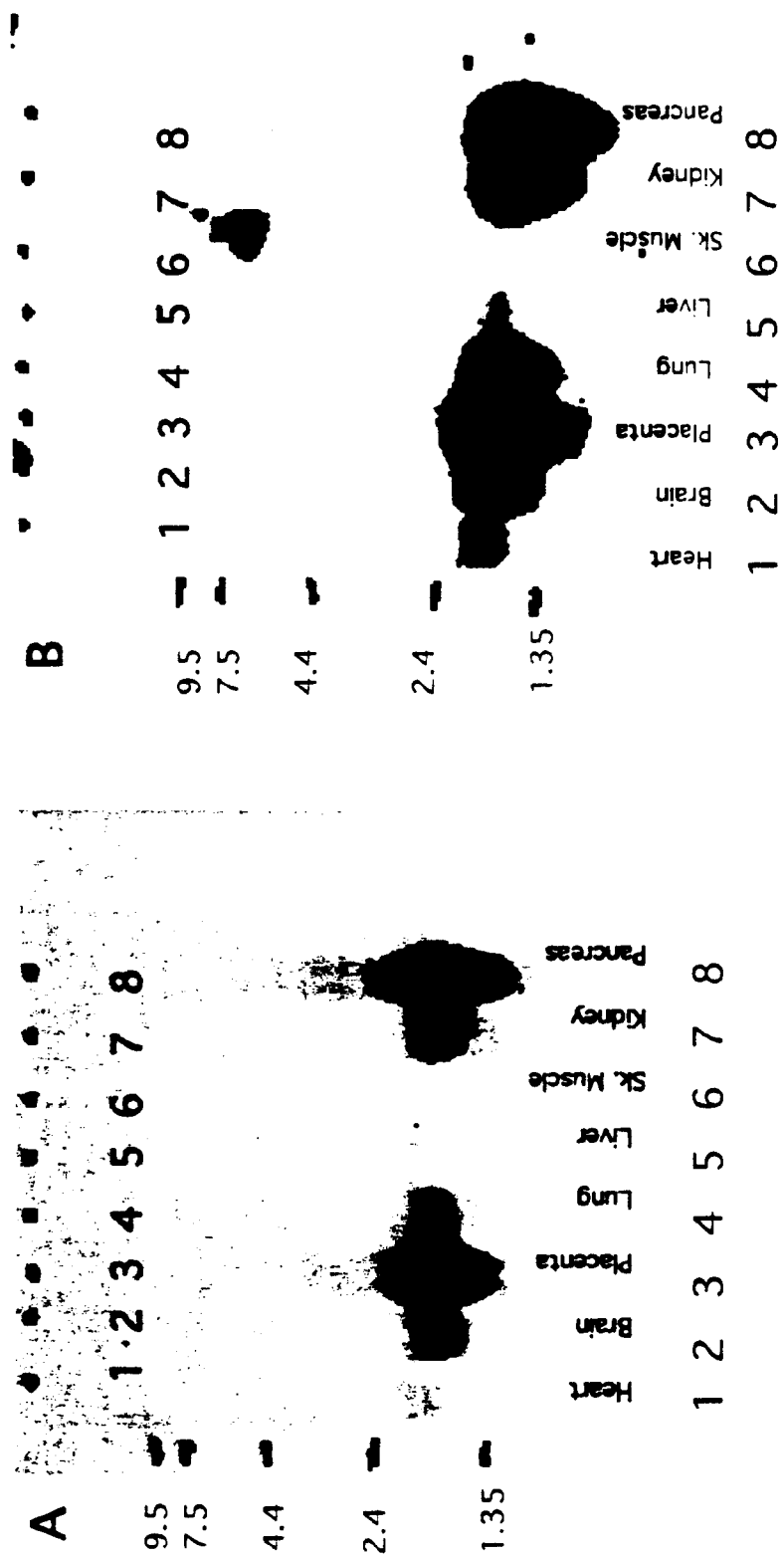
Figure 12:
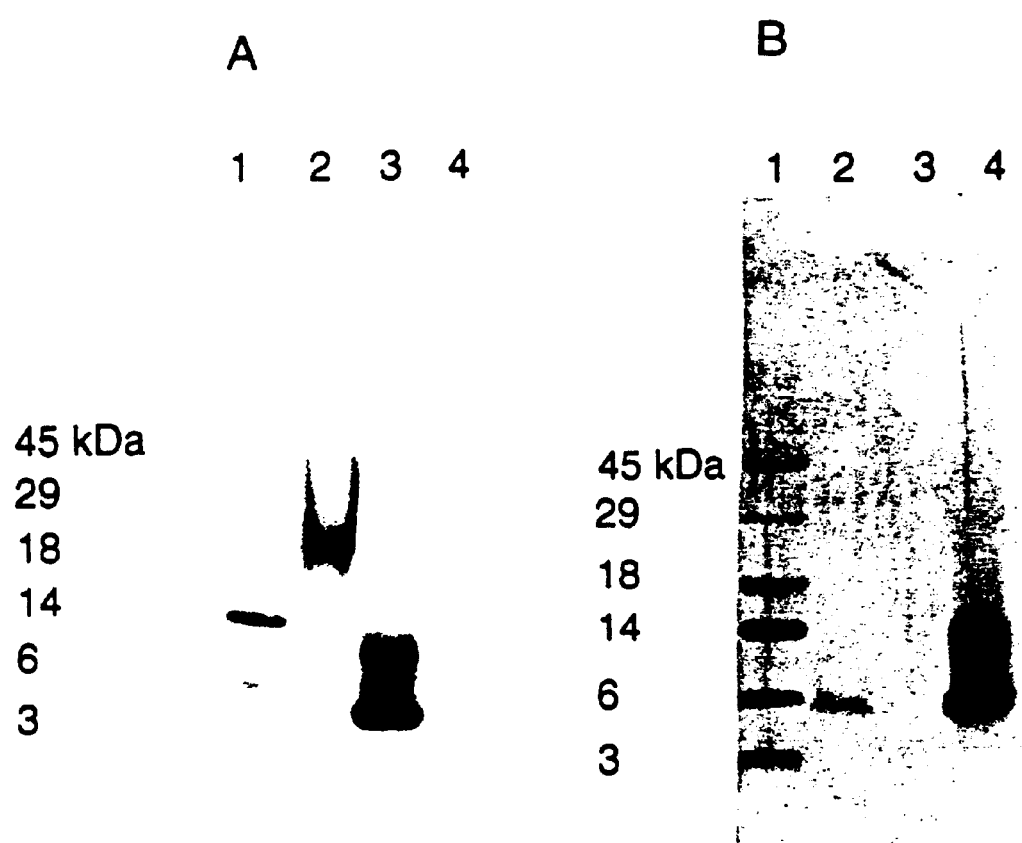
Figure 13:
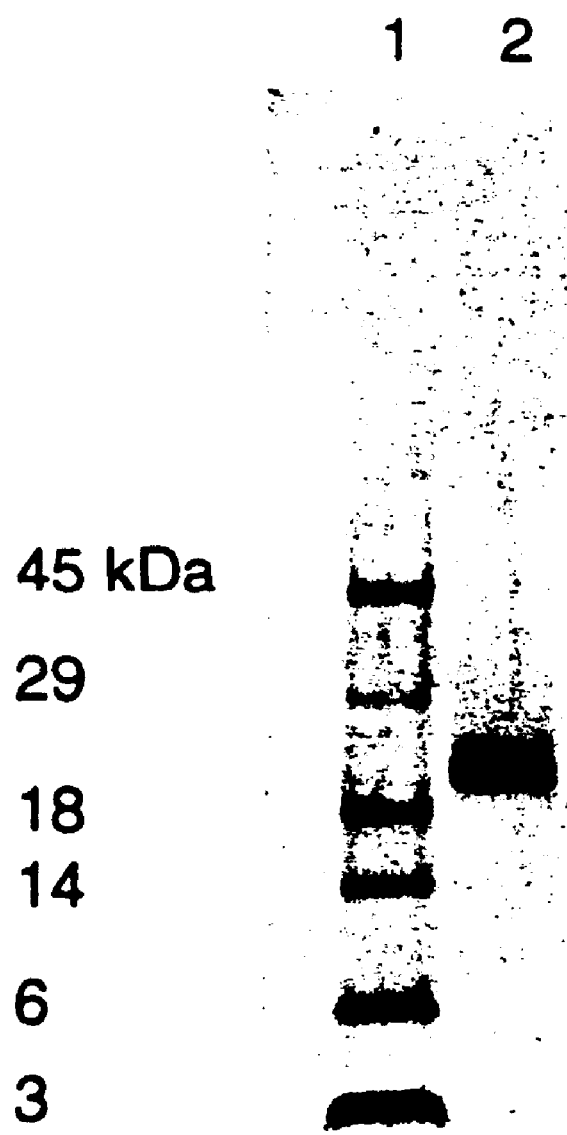
Figure 14:
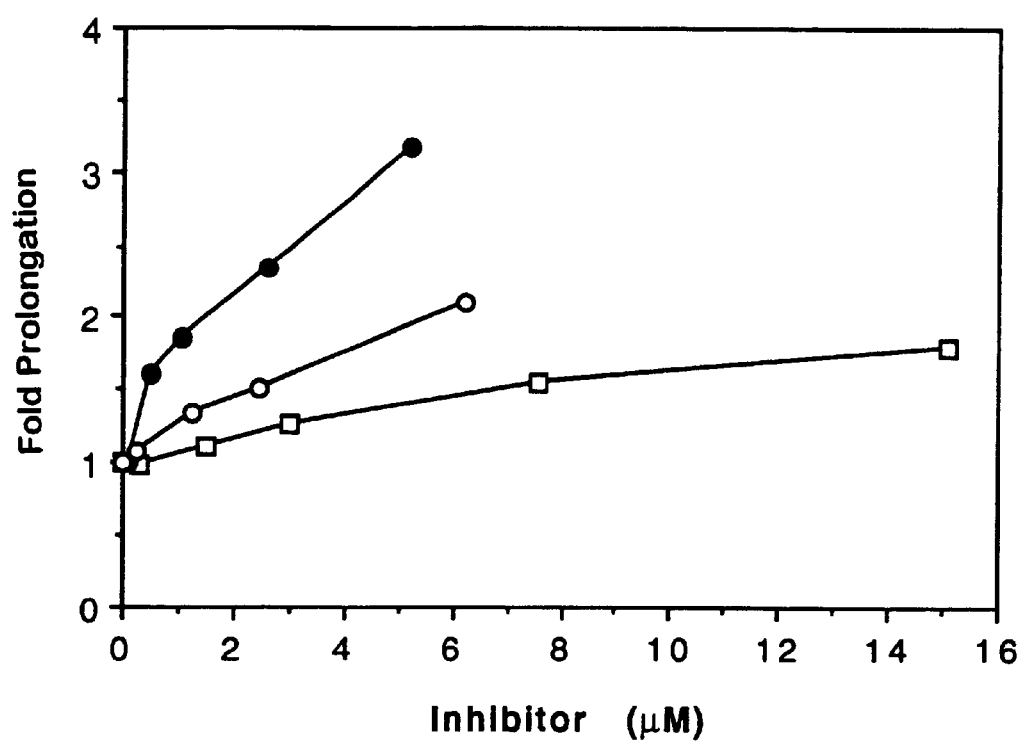

The final preparation of placental bikunin C-terminal domain was highly pure by silver-stained SDS-PAGE (FIG. 10). The overall recovery of broth-derived trypsin inhibitory activity in the final preparation was 31%. N-terminal sequencing of the purified inhibitor indicated that 40% of the protein is correctly processed to yield the correct N-terminus for placental bikunin (102–159) while about 60% of the material contained a portion of the yeast α-mating factor. The purified material comprised an active serine protease inhibitor exhibiting an apparent Ki of 0.35 nM for the in vitro inhibition of plasma kallikrein.

In conclusion, the accumulation both of a protease inhibitor activity and a protein immunochemically related to synthetic bikunin (102–159) in fermentation broth as well as the isolation of placental bikunin (102–159) from one of the transformed lines provided proof of expression of placental bikunin in the recombinant yeast strains described herein, showing for the first time the utility of yeasts for the production of placental bikunin fragments.

Additional constructs were prepared in an effort to augment the expression level of the Kunitz domain contained within placental bikunin 102–159, as well as to increase the yield of protein with the correct N-terminus. We hypothesized that the N-terminal residues of placental bikunin 102–159 (YEEY--) may have presented a cleavage site that is only poorly recognized by the yeast KEX-2 protease that enzymically removes the yeast a-factor pro-region. Therefore, we prepared yeast expression constructs for the production of placental bikunin 103–159 (N-terminus of EEY . . . ), 101–159 (N-terminus of NYEEY . . . ) and 98–159 (DMFNYEEY . . . ) in order to modify the P' subsites surrounding the KEX-2 cleavage site. To attempt to augment the levels of recombinant protein expression, we also used the yeast preferred codons rather than mammalian preferred codons in preparing some of the constructs described below. The constructs were essentially prepared as described above for placental bikunin 102–159 (defined as construct #1) but with the following modifications:
Construct #2 Placental Bikunin 103–159, Yeast Codon Usage
  A 5' sense oligonucleotide

GAAGGGGTAA GCTTGGATAA AAGAGAAGAA TACTGTACTG    (SEQ

CTAATGCTGT TACTGGTCCA TGTAGAGCTT CTTTTCCAAC    ID NO:

ATGCTACTTT CATGTTGAAA GA                       55)

and 3' antisense oligonucleotide

ACTGGATCCT CATTGGCGAA AACATCTCAA CATACAGGCT    (SEQ

TCTTCAGATC TGTAAGAATT TTTATTACCT CTACAACCAC    ID NO:

CGTAAATAAA ATTATTACAA GAATTTCTTT CAACATCAAA    56)

GTACCATCT were manipulated as described for the production of an expression construct (construct #1 above) for the expression of placental bikunin 102–159

Construct #3 Placental Bikunin 101–159, Yeast Codon Usage
  A 5' sense oligonucleotide

GAAGGGGTAA GCTTGGATAA AAGAAATTAC GAAGAATACT    (SEQ

GTACTGCTAA TGCTGTTACT GGTCCATGTA GAGCTTCTTT    ID NO:

TCCAAGATGG TACTTTGATG TTGAAAGA                 57)

and the same 3' antisense oligonucleotide as used for construct #2, were manipulated as described for the production of an expression construct (construct #1 above) for the expression of placental bikunin 102–159.
Construct #4 Placental Bikunin 98–159, Yeast Codon Usage
  A 5' sense oligonucleotide

GAAGGGGTAA GCTTGGATAA AAGAGATATG TTTAATTACG    (SEQ

AAGAATACTG TACTCCTAAT GCTGTTACTG GTCCATGTAG    ID NO:

AGCTTCTITT CCAAGATGGT ACTTTGATGT TGAAAGA       58)

and the same 3' antisense oligonucleotide as used for construct #2, were manipulated as described for the production of an expression construct (construct #1 above).

Yeast strain SC101 (MATα, ura 3–52, suc 2) was transformed with the plasmids containing each of the above cDNAs, and proteins were expressed using the methods that were described above for the production of placental bikunin 102–159 with human codon usage. Approximately 250 ml of each yeast culture was harvested, and the supernatant from centrifugation (15 min×3000 RPM) separately subjected to purification over 1 ml columns of kallikrein-sepharose as described above. The relative amount of trypsin inhibitory activity in the applysate, the amount of purified protein recovered and the N-terminal sequence of the purified protein were determined and are listed below in Table 7.

TABLE 7

Relative production levels of different proteins containing the C-terminal Kunitz domain of placental bikunin

| Construct | | Relative conc. of inhibitor in applysate | N-terminal sequencing: | | Comments |
|---|---|---|---|---|---|
| | | | amount (pmol) | sequence | |
| #2 | 103–159 | none detected | none | none | no expression |
| #3 | 101–159 | 25% inhibition | none | none | low expression |
| #4 | 98–159 | 93% inhibition | 910 | DMFNYE- | expression correct product good |
| #1 | 102–159 | 82% inibition | 480 | AKEEGV- | expression of active incorrectly processed protein |

The results show that placental bikunin fragments of different lengths that contain the C-terminal Kunitz domain show wide variation in capacity to express functional secreted protein. Constructs expressing fragments 101–159 and 103–159 yielded little or low enzymic activity in the supernatants prior to purification, and N-terminal sequencing of 0.05 ml aliquots of each purified fraction yielded undetectable amounts of inhibitor. On the other hand expression either of placental bikunin 102–159 or 98–159 yielded significant amounts of protease activity prior to purification.

N-terminal sequencing however showed that the purified protein recovered from expression of 102–159 was once again largely incorrectly processed, exhibiting an N-terminus consistent with processing of the majority of the pre-protein at a site within the yeast α-mating factor pro-sequence. The purified protein recovered from expression of placental bikunin 198–159 however was processed entirely at the correct site to yield the correct N-terminus. Furthermore, nearly twice as much protein was recovered as compared to the recovery of placental bikunin 102–159. Placental bikunin 198–159 thus represents a preferred fragment length for the production of the C-terminal Kunitz domain of placental bikunin by the α-mating factor pre-pro sequence/KEX-2 processing system of *S. cerevisiae*.

EXAMPLE 6
Alternative Procedure for Yeast Expression

The 58 amino acid peptide derived from the R74593 translation product can also be PCR amplified from either the R87894-R74593 PCR product cloned into the TA vector™ (Invitrogen, San Diego, Calif.) after DNA sequencing or from human placental cDNA. The amplified DNA product will consist of 19 nucleotides from the yeast α-mating factor leader sequence mated to the R74593 sequence which codes for the YEEY--CFRQ (58 residues) so as to make the translation product in frame, constructing an α-mating factor/Kunitz domain fusion protein. The protein sequence also contains a kex 2 cleavage which will liberate the Kunitz domain at its native N-terminus.

The 5' sense oligonucleotide which contains a HindIII site for cloning will contain the following sequence:
GCCAAGCTTG GATAAAAGAT ATGAAGAAT ACTG-CACCGC CAACGCA (SEQ ID NO: 30)

The 3' antisense oligonucleotide contains a BamhI site for cloning as well as a stop codon and is of the following sequence:
GGGGATCCTC ACTGCTGGCG GAAGCAGCGG AGCAT (SEQ ID NO: 31)

The full 206 nucleotide cDNA sequence to be cloned into the yeast expression vector is of the following sequence:

```
CCAAGCTTGC ATAAAAGATA TGAAGAATAC TGCACCGCCA    (SEQ
ACGCAGTCAC TGGGCCTTGC CGTGCATCCT TCCCACGCTG    ID NO:
GTACTTTGAC GTGGACACGA ACTCCTGCAA TAACTTCATC    32)
TATGGAGGCT GCCGGGGCAA TAAGAACAGC TACCGCTCTG
AGGAGGCCTG CATGCTCCGC TGCTCCCGCC AGCAGTGAGG
ATCCCC
```

After PCR amplification, this DNA will be digested with HindIII, BamHI and cloned into the yeast expression vector pMT15 (see U.S. Pat. No. 5,164,482, incorporated by reference in the entirety) also digested with HindIII and BamHI. The resulting plasmid vector is used to transform yeast strain SC 106 using the methods described in U.S. Pat. No. 5,164,482. The URA 3+ yeast transformants are isolated and cultivated under inducing conditions. The yield of recombinant Placental bikunin variants is determined according to the amount of trypsin inhibitory activity that accumulated in the culture supernatants over time using the in vitro assay method described above. Fermentation broths are centrifuged at 9000 rpm for 30 minutes. The supernatant is then filtered through a 0.4 then a 0.2 µm filter, diluted to a conductivity of 7.5 ms, and adjusted to pH 3 with citric acid. The sample is then batch absorbed onto 200 ml of S-sepharose fast flow (Pharmacia) in 50 mM sodium citrate pH 3 and stirred for 60 min. The gel is subsequently washed sequentially with 2 L of each of: 50 mM sodium citrate pH 3.0; 50 mM Tris-HCL pH 9.0; 20 mM HEPES pH 6.0. The washed gel is transferred into a suitable column and eluted with a linear gradient of 0 to 1 M sodium chloride in 20 mM HEPES pH 6.0. Eluted fractions containing in vitro trypsin inhibitory activity are then pooled and further purified either by a) chromatography over a column of immobilized anhydrotrypsin (essentially as described in Example 2); b) by chromatography over a column of immobilized bovine kallikrein; or c) a combination of conventional chromatographic steps including gel filtration and/or anion-exchange chromatography.

EXAMPLE 7
Isolation and Characterization of Native Human Placental Bikunin from Placenta Bikunin protein was purified to apparent homogeniety from whole frozen placenta (Analytical Biological Services, Inc, Wilmington, Del.). The placenta (740 gm) was thawed to room temperature and cut into 0.5 to 1.0 cm pieces, placed on ice and washed with 600 ml PBS buffer. The wash was decanted and 240 ml of placenta pieces placed into a Waring blender. After adding 300 ml of buffer consisting of 0.1 M Tris (pH 8.0), and 0.1 M NaCl, the mixture was blended on high speed for 2 min, decanted into 750.0 ml centrifuge tubes, and placed on ice. This procedure was repeated until all material was processed. The combined slurry was centrifuged at 4500×g for 60 minutes at 4° C. The supernatant was filtered through cheese cloth and the placental bikunin purified using a kallikrein affinity column made by covalently attaching 70 mg of bovine pancreatic kallikrein (Bayer AG) to 5.0 mls of CNBr activated Sepharose (Pharmacia) according to manufacturers instruction. The material was loaded onto the affinity column at a flow rate of 2.0 ml/min and washed with 0.1 M Tris (pH 8.0), 0.1 M NaCl until absorbance at 280 nm of the wash could no longer be detected. The column was further washed with 0.1 M Tris (pH 8.0), 0.5 M NaCl and then eluted with 3 volumes of 0.2 M acetic acid, pH 4.0. Fractions containing kallikrein and trypsin inhibitory (see below) activity were pooled, frozen, and lyophilized. Placental bikunin was further purified by gel-filtration chromatography using a Superdex 75 10/30 (Pharmacia) column attached to a Beckman System Gold HPLC system. Briefly, the column was equilibrated in 0.1 M Tris, 0.15 M NaCl, and 0.1% TRITON X-100® at a flow rate of 0.5 ml/min. The lyophilized sample was reconstituted in 1.0 ml of 0.1 M Tris, pH 8.0 and injected onto the gel-filtration column in 200 µl aliquots. Fractions were collected (0.5 ml) and assayed for trypsin and kallikrein inhibitory activity. Active fractions were pooled, and the pH of the solution adjusted to 2.5 by addition of TFA. The material was directly applied to a Vydac C18 reverse-phase column (5 micron, 0.46×25 cm) which had been equilibrated in 20% acetonitrile in 0.1 % TFA. Separation was achieved using a linear gradient of 20 to 80% acetonitrile in 0.1% TFA at 1.0 ml/min over 50 minutes after an initial 20 minute wash at 20% acetonitrile in 0.1% TFA. Fractions (1 ml) were collected and assayed for trypsin and kallikrein inhibitory activity. Fractions containing inhibitory activity were concentrated using a speed-vac concentrator (Savant) and subjected to N-terminal sequence analysis.

Functional Assays for Placental Bikunin

Identification of functional placental bikunin was achieved by measuring its ability to inhibit bovine trypsin and human plasma kallikrein. Trypsin inhibitory activity was performed in assay buffer (50 mM Hepes, pH 7.5, 0.1

M NaCl, 2.0 mM CaCl2, 0.1% TRITON X-100®) at room temperature in a 96-well microtiter plate (Perkin Elmer) using Gly-Pro-Lys-Aminomethylcoumarin as a substrate. The amount of coumarin produced by trypsin was determined by measuring the fluorescence (ex=370 nm, em=432 nm) on a Perkin-Elmer LS-50B fluorimeter equipped with a plate reader. Trypsin (23 µg in 100 µl buffer) was mixed with 20 µl of the sample to be tested and incubated for 10 minutes at 25° C. The reaction was started by the addition of 50 µl of the substrate GPK-AMC (33 µM final) in assay buffer. The fluorescence intensity was measured and the % inhibition for each fraction was determined by:

% inhibition=100×[1−Fo/F1]

where Fo is the fluorescence of the unknown and F1 is the fluorescence of the trypsin only control. Kallikrein inhibitory activity of the fractions was similarly measured using 7.0 nM kallikrein in assay buffer (50 mM Tris, pH 8.0, 50 mM NaCl, 0.1% triton x-100) and 66.0 µM Pro-Phe-Arg-AMC as a substrate.

Determination of the in vitro Specificity of Placental Bikunin

The In vitro specificity of native human placental bikunin was determined using the materials and methods as described in the preceding examples above. Placental bikunin was quantified by active site titration against a known concentration of trypsin using GPK-AMC as a substrate to monitor the fraction of unbound trypsin.

Protein Sequencing

The 1 ml fraction (C18–29 Delaria) was reduced to 300 ml in volume, on a Speed Vac, to reduce the amount of organic solvent. The sample was then loaded onto a Hewlett-Packard miniature biphasic reaction column, and washed with 1 ml of 2% trifluoroacetic acid. The sample was sequenced on a Hewlett-Packard Model G1005A protein sequencing system using Edman degradation. Version 3.0 sequencing methods and all reagents were supplied by Hewlett-Packard. Sequence was confirmed for 50 cycles.

Results. Placental Bikunin was purified to apparent homogeniety by sequential kallikrein affinity, gel-filtration, and reverse-phase chromatography (see purification table below):

TABLE 5

Purification table for native Placental Bikunin (1–179)

| Step | Vol (ml) | OD 280 (/ml) | OD 280 | Units[a] (U) | Units/ OD 280 |
|---|---|---|---|---|---|
| Placenta Supernatant | 1800.0 | 41.7 | 75,060 | 3,000,000 | 40.0 |
| Kallikrein Affinity pH 4.0 | 20.0 | 0.17 | 3.36 | 16,000 | 4,880 |
| Kallikrein Affinity pH 1.7 | 10.2 | 0.45 | 4.56 | 12,000 | 2,630 |
| Superdex 75 | 15.0 | 0.0085 | 0.13 | 3,191 | 24,546 |

[a]One Unit is defined as that amount which inhibits 50% of trypsin activity in a standard assay.

The majority of the kallikrein and trypsin inhibitory activity eluted from the kallikrein affinity column in the pH 4.0 elution. Subsequent gel-filtration chromatography (FIG. 5) yielded a peak of kallikrein and trypsin inhibitory activity with a molecular weight range of 10 to 40 kDa as judged by a standard curve generated by running molecular weight standards under identical conditions. Reverse-phase C18 chromatography (FIG. 6) yielded 4 peaks of inhibitory activity with the most potent eluting at approximately 30% acetonitrile. The activity associated with the first peak to elute from C18 (fraction 29) exhibited an amino acid sequence starting with amino acid 1 of the predicted amino acid sequence of placental bikunin (ADRER . . . ; SEQ ID NO: 1), and was identical to the predicted sequence for 50 cycles of sequencing (underlined amino acids in FIGS. 3A-1 and 3A-2). Cysteine residues within this sequence stretch were silent as expected for sequencing of oxidized protein. The cysteine residues at amino acid positions 11 and 20 of mature placental bikunin were later identified from sequencing of the S-pyridylethylated protein whereupon PTH-pyridylethyl-cysteine was recovered at cycles 11 and 20.

Figure 6:
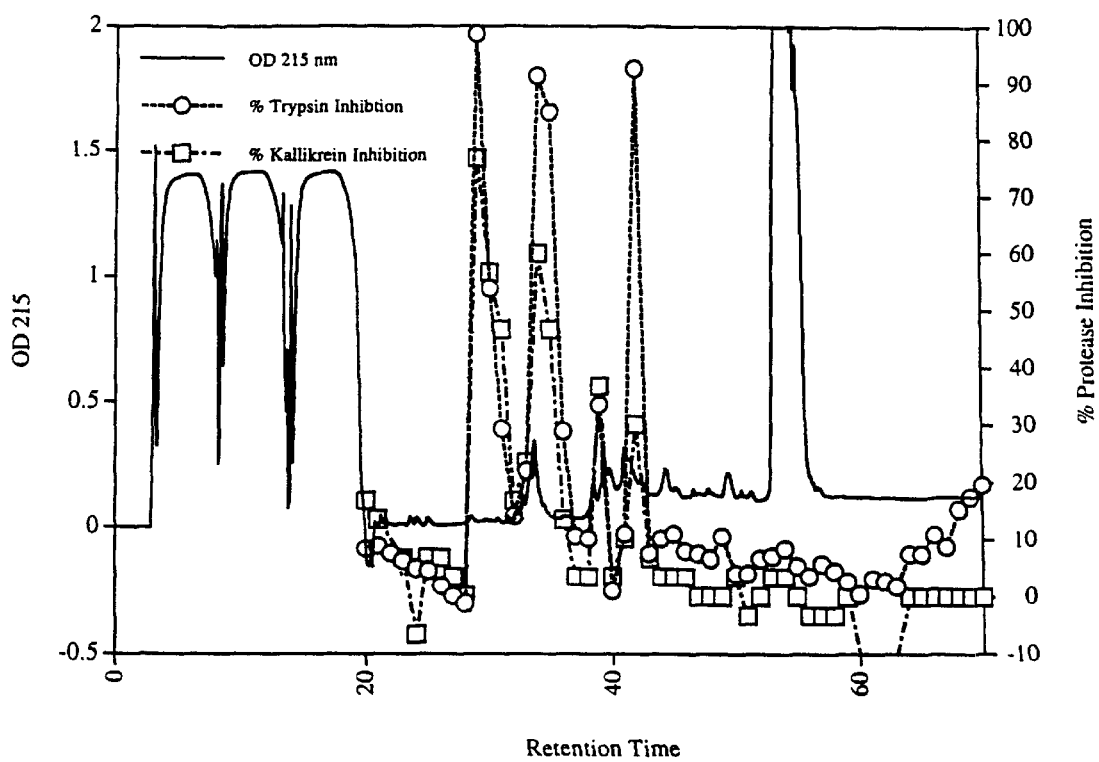

Interestingly, the asparagine at amino acid residue number 30 of the sequence (FIG. 3A-1) was silent showing that this site is likely to be glycosylated. Fraction 29 yielded one major sequence corresponding to that of placental bikunin starting at residue #1 (27 pmol at cycle 1) plus a minor sequence (2 pmol) also derived from placental bikunin starting at residue 6 (SIHD . . . ). This shows that the final preparation sequenced in fraction 29 is highly pure, and most likely responsible for the protease inhibitory activity associated with this fraction (FIG. 6).

Accordingly, the final preparation of placental bikunin from C18 chromatography was highly pure based on a silver-stained SDS-PAGE analysis (FIG. 7), where the protein migrated with an apparent Mr of 24 kDa on a 10 to 20% acrylamide tricine gel (Novex, San Diego, Calif.) calibrated with the following molecular weight markers: insulin (2.9 kDa); bovine trypsin inhibitor (5.8 kDa); lysozyme (14.7 kDa); β-lactaglobulin (18.4 kDa); carbonic anhydrase (29 kDa); and ovalbumin (43 kDa). The above size of placental bikunin on SDS-PAGE is consistent with that predicted from the full length coding sequence (FIG. 4F).

Figure 7:
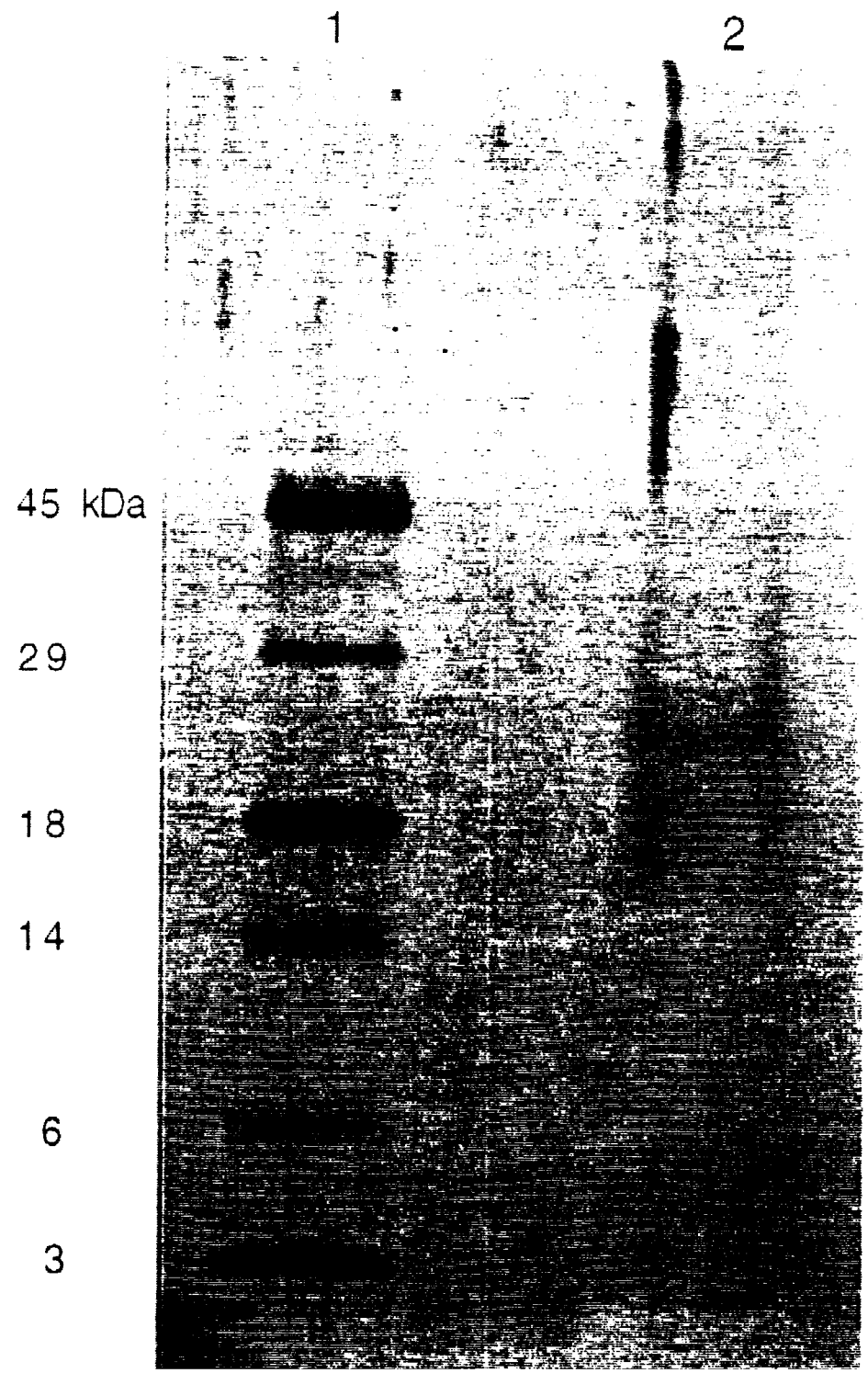

As expected based on the N-terminal sequencing results described above, the purified protein reacted with an antibody elicited to placental bikunin (7–64) to yield a band with the same Mr (FIG. 12A) as observed for the purified preparation detected on gels by silver stain (FIG. 7). However, when the same preparation was reacted with an antibody elicited to synthetic placental bikunin (102–159), a band corresponding to the full length protein was not observed. Rather, a fragment that co-migrated with synthetic bikunin (102–159) of approximately 6 kDa was observed. The simplest interpretation of these results is that the purified preparation had undergone degradation subsequent to purification to yield an N-terminal fragment comprising the N-terminal domain and a C-terminal fragment comprising the C-terminal domain. Assuming that the fragment reactive against antiserum to placental bikunin (7–64) is devoid of the C-terminal end of the full length protein, the size (24 kDa) would suggest a high state of glycosylation.

Table 6. below shows the potency of in vitro inhibition of various serine proteases by placental bikunin. Data are compared with that obtained with aprotinin (Trasylol®).

TABLE 6

Ki values for the inhibition of various proteases by placental bikunin

| Protease (concentration) | Placental Bikunin Ki (nM) | Aprotinin Ki (nM) |
|---|---|---|
| Trypsin (48.5 pM) | 0.13 | 0.8 |
| Human Plasmin (50 pM) | 1.9 | 1.3 |

The results show that placental bikunin isolated from a natural source (human placenta) is a potent inhibitor of trypsin-like serine proteases.

EXAMPLE 8
Expression Pattern of Placental Bikunin Amongst Different Human Organs and Tissues A multiple tissue northern was purchased from Clontech which contained 2 μg of polyA+ RNA from human heart, brain, placenta, lung, liver, skeletal muscle, kidney, and pancreas. Two different cDNA probes were used: 1) a gel purified cDNA encoding placental bikunin (102–159); 2) the 780 base pair PCR-derived cDNA (FIG. 4E) liberated from a TA clone by digestion with EcoRI and gel purified. Each probe was labeled using $^{32}$P-dCTP and a random priming labeling kit from Boehringer Mannheim Biochemicals (Indiana), then used to hybridize to the multiple tissue northern according to the manufacturers specifications. Autoradiographs were generated using Biomax film with an 18 hr exposure time, and developed using a Umax Scanner and scanned using Adobe Photoshop.

Results. The pattern of tissue expression observed using a placental bikunin (102–159) probe (FIG. 11A) or a larger probe containing both Kunitz domains of placental bikunin (FIG. 11B) was essentially the same as might be expected. The placental bikunin mRNA was most abundant in pancreas and placenta. Significant levels were also observed in lung, brain and kidney, while lower levels were observed in heart and liver, and the mRNA was undetectable in skeletal muscle. The transcript size was 1.95 kilobases in all cases, in close agreement with the predicted size of placental bikunin deduced both from EST overlay and cloning of full length cDNA described in preceding sections.

The broad tissue distribution of the mRNA shows that placental bikunin is broadly expressed. Since the protein also contains a leader sequence it would have ample exposure to the human immune system, requiring that it become recognized as a self protein. Additional evidence for a broad tissue distribution of placental bikunin MRNA expression was derived from the fact that some of the EST entries with homology to placental bikunin (FIG. 4B) were derived from human adult and infant brain, and human retina, breast, ovary, olfactory epithelium, and placenta. It is concluded therefore that administration of the native human protein to human patients would be unlikely to elicit an immune response.

Interestingly, the expression pattern of placental bikunin is somewhat reminiscent of that for bovine aprotinin which is found in high levels in bovine lung and pancreas. To further elucidate the expression pattern of placental bikunin, RT-PCR of total RNA from the following human cells was determined: un-stimulated human umbilical vein endothelial cells (HUVECs), HK-2 (line derived from kidney proximal tubule), TF-1 (erythroleukemia line) and phorbolester (PMA)-stimulated human peripheral blood leukocytes. The probes used:

CACCTGATCGCGAGACCCC (sense; SEQ ID NO: 59);
CTGGCGGAAGCAGCGGAGCATGC (antisense; SEQ ID NO: 60), were designed to amplify a 600 b.p placental bikunin encoding cDNA fragment. Comparisons were normalized by inclusion of actin primers to amplify an 800 b.p. actin fragment. Whereas the 800 b.p fragment identified on agarose gels with ethidium bromide was of equal intensity in all lanes, the 600 b.p. placental bikunin fragment was absent from the HUVECs but present in significant amounts in each of the other cell lines. We conclude that placental bikunin is not expressed in at least some endothelial cells but is expressed in some leukocyte populations.

EXAMPLE 9
Purification and Properties of Placental Bikunin (1–170) Highly Purified from a Baculovirus/Sf9 Expression System A large fragment of Placental bikunin containing both Kunitz domains (Placental Bikunin 1–170) was expressed in Sf9 cells as follows. Placental bikunin cDNA obtained by PCR (FIG. 4E) and contained within a TA vector (see previous Examples) was liberated by digestion with HindIII and XbaI yielding a fragment flanked by a 5' XbaI site and 3' HindIII site. This fragment was gel purified and then cloned into the M13mp19 vector (New England Biolabs, Beverly, Mass.). In vitro mutagenesis (Kunkel T. A., (1985) Proc. Natl. Acad. Sci. USA, 82: 488–492) was used to generate a Pst1 site 3' to the XbaI site at the 5' end, but 5' to the sequence encoding the ATG start site, natural placental bikunin signal peptide and mature placental bikunin coding sequence. The oligonucleotide used for the mutagenesis had the sequence:

5' CGC GTC TCG GCT GAC CTG GCC CTG CAG ATG GCG CAC GTG TGC GGG 3' (SEQ ID NO: 61)

A stop codon (TAG) and BglII/XmaI site was similarly engineered at the 3' end of the cDNA using the oligonucleotide:

5' CTG CCC CTT GGC TCA AAG TAG GAA GAT CTT CCC CCC GGG GGG GTG GTT CTG GCG GGG CTG 3' (SEQ ID NO: 62).

The stop codon was in frame with the sequence encoding placental bikunin and caused termination immediately following the Lysine at amino acid residue 170, thus encoding a truncated placental bikunin fragment devoid of the putative transmembrane domain. The product from digestion with Pst1 and BglII was isolated and cloned into the BacPac8 vector for expression of Placental bikunin fragment (1–170) which contains both Kunitz domains but which is truncated immediately N-terminal to the putative transmembrane segment.

The expression of Bikunin by Sf-9 insect cells was optimal at a multiplicity of infection of 1 to 1 when the medium was harvested at 72 h post infection. After harvesting, the baculovirus cell culture supernatant (2L) was adjusted to pH 8.0 by the addition of Tris-HCl. Bikunin was purified by chromatography using a 5 ml bovine pancreatic kallikrein affinity column as previously described in Example 7 for the purification of native placental bikunin from placenta. Eluted material was adjusted to pH 2.5 with TFA and subjected to chromatography on a C18 reverse-phase column (1.0×25 cm) equilibrated in 10% acetonitrile in 0.1% TFA at a flow rate of 1 ml/min. The bikunin was eluted with a linear gradient of 10 to 80% acetonitrile in 0.1% TFA over 40 min. Active fractions were pooled, lyophilized, redissolved in 50 mM Hepes (pH 7.5), 0.1 M NaCl, 2 mM CaCl2, and 0.1% triton x-100, and stored at −20° C. until needed. The concentration of recombinant bikunin was determined by amino acid analysis.

Results. Recombinant bikunin was purified from baculovirus cell culture supernatant using a 2-step purification protocol as shown below, to yield an active trypsin inhibitor (Table 8 below).

TABLE 8

Purification of recombinant bikunin from transformed culture supernatant

| Purification Step | Vol (ml) | OD 280/ml | OD 280 total | Units (U) | Specific activity (U/OD) |
|---|---|---|---|---|---|
| Supernatant | 2300.0 | 9.0 | 20,700 | 6,150,000 | 297 |
| Kallikrein affinity | 23.0 | 0.12 | 2.76 | 40,700 | 14,746 |
| C18 reverse-phase | 0.4 | 3.84 | 154 | 11,111 | 72,150 |

Chromatography of the crude material over an immobilized bovine pancreatic kallikrein affinity column selectively isolated 0.013% of the protein and 0.67% of the trypsin inhibitory activity present. The majority of the trypsin inhibitory activity present in the starting supernatant did not bind to the immobilized kallikrein and is not related to bikunin (results not shown). Subsequent chromatography using C18 reverse-phase yielded a further purification of 5-fold, with a recovery of 0.2%. The final preparation was highly pure by SDS-PAGE (FIG. 13), exhibiting an Mr of 21.3 kDa, and reacted on immunoblots to rabbit anti-placental bikunin 102–159 (not shown). N-terminal sequencing (26 cycles) yielded the expected sequence for mature placental bikunin (FIGS. 4F-1 and 4F-2) starting at residue +1(ADRER . . . ), showing that the signal peptide was correctly processed in Sf9 cells.

Purified placental bikunin from Sf9 cells (100 pmol) was pyridylethyl-alkylated, CNBr digested and then sequenced without resolution of the resulting fragments. Sequencing for 20 cycles yielded the following N-terminii:

| Sequence | Amount | Placental bikunin residue # |
|---|---|---|
| LRCFrQQENPP-PLG----- | 21 pmol | 154–168 (SEQ ID NO:63) |
| ADRERSIHDFCLVSKVVGRC | 20 pmol | 1–20 (SEQ ID NO:64) |
| FNYeEYCTANAVTGPCRASF | 16 pmol | 100–119 (SEQ ID NO:65) |
| Pr---Y-V-dGS-Q-F-Y-G | 6 pmol | 25–43 (SEQ ID NO.66) |

Thus N-terminii corresponding to each of the expected four fragments were recovered. This confirms that the Sf9 expressed protein contained the entire ectodomain sequence of placental bikunin (1–170). N-terminal sequencing (50 cycles) of an additional sample of undigested Placental Bikunin (1–170) resulted in an amino acid sequence which at cycle 30 was devoid of any PTH-amino acid (PTH-asparagine was expected). A similar result was obtained upon sequencing of the natural protein from human placenta (Example 7) and is consistent with this residue being glycosylated as predicted from the amino acid sequence surrounding this asparagine residue. Furthermore, the cysteine residues within this region were also silent consistent with their participation in disulfide bonding.

EXAMPLE 10
Inhibition Specificity of Purified Placental Bikunin Derived from Sf9 Cells The in vitro specificity of recombinant bikunin was determined using the materials and methods as described in Examples 3, 4 and 7. In addition, the inhibition of human tissue kallikrein by bikunin was measured by the incubation of 0.35 nM human tissue kallikrein recombinant bikunin in buffer containing 50 mM Tris (pH 9.0), 50 mM NaCl, and 0.01% TRITON X-100®. After 5 min. at 37° C., 5 μm of 2 mM PFR-AMC was added and the change in fluorescence monitored.

Inhibition of tissue plasminogen activator (tPA) was also determined as follows: tPA (single chain form from human melanoma cell culture from Sigma Chemical Co, St Louis, Mo.) was pre-incubated with inhibitor for 2 hr at room temperature in 20 mM Tris buffer pH 7.2 containing 150 mM NaCl, and 0.02% sodium azide. Reactions were subsequently initiated by transfer to a reaction system comprising the following initial component concentrations: tPA (7.5 nM), inhibitor 0 to 6.6 μM, DIle-Lpro-Larg-pNitroaniline (1 mM) in 28 mM Tris buffer pH 8.5 containing 0.004% (v/v) triton x-100 and 0.005% (v/v) sodium azide. Formation of p-Nitroaniline was determined from the A405nm measured 5 following incubation at 37 C. for 2 hr.

The table below show the efficacy of recombinant bikunin as an inhibitor of various serine proteases in vitro. Data is shown compared against data obtained for screening inhibition using either recombinant bikunin, or aprotinin.

TABLE 9

Comparisons of Ki values for the inhibition of various proteases by recombinant placental bikunin (1–170) or aprotinin

| Protease (concentration) | Recombinant Bikunin Ki (nM) | Aprotinin Ki (nM) |
|---|---|---|
| Trypsin (48.5 pM) | 0.064 | 0.8 |
| Human Plasma Kallikrein (2.5 nM) | 0.18 | 19.0 |

TABLE 9-continued

Comparisons of Ki values for the inhibition of various proteases by recombinant placental bikunin (1–170) or aprotinin

| Protease (concentration) | Recombinant Bikunin Ki (nM) | Aprotinin Ki (nM) |
|---|---|---|
| Human Tissue Kallikrein (0.35 nM) | 0.04 | 0.004 |
| Bovine Pancreatic Kallikrein (100 pM) | 0.12 | 0.02 |
| Human Plasmin (50 pM) | 0.23 | 1.3 |
| factor Xa (0.87 nM) | 180 | 5% Inhibition at 31 μM |
| factor XIa (0.1 nM) | 3.0 | 288 |
| tissue plasminogen activator (7.5 nM | <60 | no inhibition at 6.6 μM |
| Tissue Factor VIIa | 800 | no inhibition at 1 μM |

The results show that recombinant bikunin can be expressed in insect cells to yield an active protease inhibitor that is effective against at least five different serine protease inhibitors. Recombinant bikunin was more potent than aprotinin against human plasma kallikrein, trypsin and plasmin. Surprisingly, the recombinant bikunin was more potent that the synthetically derived bikunin fragments (7–64) and (102–159) against all enzymes tested. These data show that recombinant bikunin is more effective than aprotinin, using in vitro assays, and that one would expect better in vivo potency.

Besides measuring the potencies against specific proteases, the capacity of placental bikunin (1–170) to prolong the activated partial thromboplastin time (APTT) was evaluated and compared with the activity associated with aprotinin. Inhibitor was diluted in 20 mM Tris buffer pH2 containing 150 mM NaCl and 0.02% sodium azide and added (0.1 ml) to a cuvette contained within an MLA Electra® 800 Automatic Coagulation Timer coagulometer (Medical Laboratory Automation, Inc., Pleasantville, N.Y.). The instrument was set to APTT mode with a 300 sec. activation time and the duplicate mode. Following addition of 0.1 ml of plasma (Specialty Assayed Reference Plasma lot 1-6-5185, Helena Laboratories, Beaumont, Tex.), the APTT reagent (Automated APTT-lot 102345, from Organon Teknika Corp., Durhan, N.C.) and 25 mM CaCl2 were automatically dispensed to initiate clotting, and the clotting time was monitored automatically. The results (FIG. 14) showed that a doubling of the clotting time required approximately 2 µM final aprotinin, but only 0.3 µM Sf9 derived placental bikunin. These data show that placental bikunin is an effective anticoagulant, and useful as a medicament for diseases involving pathologic activation of the intrinsic pathway of coagulation.

Although certain embodiments of the invention have been described in detail for the purpose of illustration, it will be readily apparent to those skilled in the art that the methods and formulations described herein may be modified without departing from the spirit and scope of the invention. Accordingly, the invention is not limited except as by the appended claims.

We claim:

1. A substantially purified protein, having serine protease inhibitory activity, selected from the group of proteins consisting of materials each of which comprises one of the following amino acid sequences, the amino acids of said sequences being numbered in accordance with the amino acid sequence of native human placental bikunin shown in FIG. 4F in which the N-terminal residue generated by removal of signal peptide is designated as residue 1:

```
                              AGSFLAWL GSLLLSGVLA  -1

ADRERSIHDF CLVSKVVGRC
            RASMPRWWYN VTDGSCQLFV YGGCDGNSNN  50

YLTKEECLKK CATVTENATG
            DLATSRNAAD SSVPSAPRRQ DSEDHSSDMF  100

NYEEYCTANA VTGPCRASFP
            RWYFDVERNS CNNFIYGGCR GNKNSYRSEE  150

ACMLRCFRQQ ENPPLPLGSK VVVLAGAVS              179
(SEQ ID NO: 2);

MLR AEADGVSRLL GSLLLSGVLA  -1

ADRERSIHDF CLVSKVVGRC
            RASMPRWWYN VTDGSCQLFV YGGCDGNSNN  50

YLTKEECLKK CATVTENATG
            DLATSRNAAD SSVPSAPRRQ DSEDHSSDMF  100

NYEEYCTANA VTGPCRASFP
            RWYFDVERNS CNNFIYGGCR GNKNSYRSEE  150

ACMLRCFRQQ ENPPLPLGSK
            VVVLAGLFVM VLILFLGASM VYLIRVARRN  200

QERALRTVWS SGDDKEQLVK NTYVL                  225
(SEQ ID NO: 45);

MAQLCGL RRSRAFLALL GSLLLSGVLA  -1

ADRERSIHDF CLVSKVVGRC
            RASMPRWWYN VTDGSCQLFV YGGCDGNSNN  50

YLTKEECLKK CATVTENATG
            DLATSRNAAD SSVPSAPRRQ DSEDHSSDMF  100

NYEEYCTANA VTGPCRASFP
            RWYFDVERNS CNNFIYGGCR GNKNSYRSEE  150

ACMLRCFRQQ ENPPLPLGSK
            VVVLAGLFVM VLILFLGASM VYLIRVARRN  200

QERALRTVWS FGD                               213
(SEQ ID NO: 47); and

ADRERSIHDF CLVSKVVGRC
            RASMPRWWYN VTDGSCQLFV YGGCDGNSNN  25

YLTKEECLKK CATVTENATG
            DLATSRNAAD SSVPSAPRRQ DSEDHSSDMF  75

NYEEYCTANA VTGPCRASFP
            RWYFDVERNS CNNFIYGGCR GNKNSYRSEE  125

ACMLRCFRQQ ENPPLPLGSK VVVLAGAVS              179
(SEQ ID NO.: 1);.
```

2. A substantially purified serine protease inhibitor protein containing at least one Kunitz-like domain comprising an amino acid sequence:

ADRERSIHDF CLVSKVVGRC RASMPRWWYN VTDGSCQLFV YGGCDGNSNN 50

YLTKEECLKK CATVTENATG DLATSRNAAD SSVPSAPRRQ DS 92

(SEQ ID NO.: 8) with the proviso that the protein does not have the amino acid sequence of SEQ ID NOS.:49 and b 71.

3. A substantially purified protein, having serine protease inhibitory activity, selected from the group of proteins consisting of materials each of which consists one of the following amino acid sequences, the amino acids of said sequences being numbered in accordance with the amino acid sequence of native human placental bikunin shown in FIG. 4F in which the N-terminal residue generated by removal of the signal peptide is designated as residue 1:

```
ADRERSIHDF CLVSKVVGRC RASMPRWWYN VTDGSCQLFV YGGCDGNSNN        50
YLTKEECLKK CATVTENATG DLATSRNAAD SSVPSAPRRQ DSESHSSDMF       100
NYEEYCTANA VTGPCRASFP RWYFDVERNS CNNFIYGGCR GNKNSYRSEE       150
ACMLRCFRQQ ENPPLPLGSK                                        170
(SEQ ID NO:52);

AGSFLAWL GSLLLSGVLA             -1
ADRERSIHDF CLVSKVVGRC RASMPRWWYN VTDGSCQLFV YGGCDGNSNN        50
YLTKEECLKK CATVTENATG DLATSRNAAD SSVPSAPRRQ DSEDHSSDMF       100
NYEEYCTANA VTGPCRASFP RWYFDVERNS CNNFIYGGCR GNKNSYRSEE       150
ACMLRCFRQQ ENPPLPLGSK VVVLAGVS                               179
(SEQ ID NO:2);

MLR AEADGVSRLL GSLLLSGVLA                  -1
ADRERSIHDF CLVSKVVGRC RASMPRWWYN VTDGSCQLFV YGGCDGNSNN        50
YLTKEECLKK CATVTFNATG.DLATSRNAAD SSVPSAPRRQ DSEDHSSDMF       100
NYEEYCTANA VTGPCRASFP RWYFDVERNS CNNFIYGGCR GNKNSYRSEE       150
ACMLRCFRQQ ENPPLPLGSK VVVLAGLFVM VLILFLGASM VYLIRVARRN       200
QERALRTVWS SGDDKEQLVK NTYVL                                  225
(SEQ ID NO:45);

MAQLCGL RRSRAFLALL GSLLLSGVLA                  -1
ADRERSIHDF CLVSKVVGRC RASMPRWWYN VTDGSCQLFV YGGCDGNSNN        50
YLTKEECLKK CATVTENATG DLATSRNAAD SSVPSAPRRQ DSEDHSSDMF       100
NYEEYCTANA VTGPCRASFP RWYFDVERNS CNNFIYGGCR GNKNSYRSEE       150
ACMLRCFRQQ ENPPLPLGSK VVVLAGLFVM VLILFLGASM VYLIRVARRN       200
QERALRTVWS FGD                                               213
(SEQ ID NO:47);

ADRERSIHDF CLVSKVVGRC RASMPRWWYN VTDGSCQLFV YGGCDGNSNN        50
YLTKEECLKK CATVTENATG DLATSRNAAD SSVPSAPRRQ DSEDHSSDMF       100
NYEEYCTANA VTGPCRASFP RWYFDVERNS QNNFIYGGCR GNKNSYRSEE       150
ACMLRCFRQQ ENPPLPLGSK VJVLAGLFVM VLILFLGASM VYLIRVARRN       200
QERALRTVWS FGD                                               213
(SEQ ID NO:70);

IHDF CLVSKVVGRC RASMPRWWYN VTDGSCQLEV YGGCDGNSNN        50
YLTKEECLKK CATV                                               64
(SEQ ID NO:4);

CLVSKVVGRC RASMPRWWYN VTDGSCQLFV YGGCDGNSNN        50
YLTKEECLKK C                                                  61
(SEQ ID NO.:5);

YEEYCTANA VTGPCPASFP RWYFDVERNS QNNFIYGGCR GNKNSYRSEE        150
ACMLRC FRQ                                                   159
(SEQ ID NO:6);

CTANA VTGPCRASFP RWYFDVERNS CNNFIYGGCR GNKNSYRSEE        150
ACMLRC                                                       156
(SEQ ID NO:7);

IHDF CLVSKVVGRC RASMPRWWYN VTDGSCQLFV YGGCDGNSNN        50
YLTKEECLKK CATVTENATG DLATSRNAAD SSVPSAPRRQ DSEDHSSDMF       100
NYEEYCTANA VTGPCRASFP RWYFDVERNS CNNFIYGGCR GNKNSYRSEE       150
ACMLRCFRQ                                                    159
(SEQ ID NO:3);

CLVSKVVGRC RASMPRWWYN VTDGSCQLFV YGGCDGNSNN        50
YLTKEECLKK CATVTENATG DLATSRNAAD SSVPSAPRRQ DSEDHSSDMF       100
NYEEYCTANA VTGPCRASFP RWYFDVERNS CNNFIYGGCR GNKNSYRSEE       150
ACMLRC                                                       156
(SEQ ID NO:50);

ADRERSIHDF CLVSKVVGRC RASMPRWWYN VTDGSCQLFV YGGCDGNSNN        50
YLTKEECLKK CATVTENATG DLATSRNSAD SSVPSAPRRQ DSEDHSSDMF       100
NYEEYCTANA YTGPCPASFP RWYFDVERNS CNNFIYGGCR GNKNSYRSEE       150
ACMLRCFRQQ ENPPLPLGSK VVVLAGAVS                              179
(SEQ ID NO:1); and ADRERSIHDF CLVSKVVGRC RASMPRWWYN VTDGSCQLFV YGGCDGNSNN        50
YLTKEECLKK CATVTENATG DLATSRNAAD SSVPSAPRRQ DS                92
(SEQ ID NO:8).
```

4. A protein as in claims 1, 2 or 3 wherein said protein is glycosylated, or contains at least one intra-chain cysteine-cysteine disulfide bond, or is both glycosylated and contains at least one intra-chain cysteine-cysteine disulfide bond.

5. A pharmaceutical composition for inhibiting serine protease activity, comprising a protein of claims 1, 2, 4, or 3 plus a pharmaceutically acceptable carrier.

6. A method for inhibiting serine protease activity comprising contacting serine protease with an effective amount of at least one protein of claims 1, 2, 4, or 3.

7. A method for treating a condition of brain edema, spinal cord edema, multiple sclerosis, ischemia, postoperative blood loss, sepsis, septic shock, fibrosis, disease associated with pathologic blood coagulation or clotting, polytrauma, stroke, cerebral or subarachnoid hemorrhage, inflammation of the brain, inflammation of the spinal cord, cerebral infection, cerebral granulomatosis, spinal infection, spinal granulomatosis, open heart surgery, gastric cancer, cervical cancer, or prevention of metastasis comprising administering to a subject having such a condition an effective amount of the protein of claims 1, 2, 4 or 3.

8. The method of claim 7 wherein said condition is brain edema, spinal cord edema, multiple sclerosis, ischemia, perioperative blood loss, sepsis, septic shock, fibrosis, disease associated with pathologic blood coagulation or clotting, stroke, cerebral or subarachnoid hemorrhage, inflammation of the brain, inflammation of the spinal cord, cerebral infection, cerebral granulomatosis, spinal infection, spinal granulomatosis, or open heart surgery.

9. The method of claim 7 wherein said condition is gastric cancer, cervical cancer, or prevention of metastasis.

* * * * *

UNITED STATES PATENT AND TRADEMARK OFFICE
CERTIFICATE OF CORRECTION

PATENT NO. : 6,583,108 B1
DATED : June 24, 2003
INVENTOR(S) : Paul P. Tamburini et al.

It is certified that error appears in the above-identified patent and that said Letters Patent is hereby corrected as shown below:

Column 104,
Line 33, delete "25" at the right margin, and replace with -- 50 --.
Line 36, delete "75" at the right margin, and replace with -- 100 --.
Line 39, delete "125" at the right margin, and replace with -- 150 --.
Line 57, delete "b 71" at the end of the claim, and replace with -- 71 --.
Line 61, delete "consists one" and replace with -- consists of one --.

Column 105,
Line 2, (SEQ ID NO:52), delete "S" at position 94 of the sequence, and replace with -- D --.
Line 10, (SEQ ID NO:2), insert -- A -- between "G" at position 176 and "V" at postion 177 of the sequence.
Line 14, (SEQ ID NO:45), delete "F" at position 66 of the sequence, and replace with -- E --.
Line 14, (SEQ ID NO:45), delete "." between G at position 70 and D at position 71 of the sequence.
Line 28, (SEQ ID NO:70), delete "Q" at position 131 of the sequence, and replace with -- C --.
Line 29, (SEQ ID NO:70), delete "J" at position 172 of the sequence, and replace with -- V --.
Line 32, (SEQ ID NO:4), delete "E" at position 39 of the sequence, and replace with -- F --.
Line 38, (SEQ ID NO:6), delete "P" at position 116 of the sequence, and replace with -- R --.
Line 38, (SEQ ID NO:6), delete "Q" at position 131 of the sequence, and replace with -- C --.
Line 55, (SEQ ID NO:1), delete "S" at position 78 of the sequence, and replace with -- A --.
Line 56, (SEQ ID NO:1), delete "Y" at position 111 of the sequence, and replace with -- V --.
Line 56, (SEQ ID NO:1), delete "P" at position 116 of the sequence, and replace with -- R --.

UNITED STATES PATENT AND TRADEMARK OFFICE
CERTIFICATE OF CORRECTION

PATENT NO.    : 6,583,108 B1
DATED         : June 24, 2003
INVENTOR(S)   : Paul P. Tamburini et al.

It is certified that error appears in the above-identified patent and that said Letters Patent is hereby corrected as shown below:

<u>Column 107,</u>
Lines 6-7, delete "4, or 3", and replace with -- 3, or 4 --.
Line 10, delete "4, or 3", and replace with -- 3, or 4 --.

<u>Column 108,</u>
Line 4, delete "4, or 3", and replace with -- 3, or 4 --.

Signed and Sealed this

Eighteenth Day of November, 2003

JAMES E. ROGAN
*Director of the United States Patent and Trademark Office*